(12) United States Patent
Gellert et al.

(10) Patent No.: US 12,115,174 B2
(45) Date of Patent: *Oct. 15, 2024

(54) DENDRIMER FORMULATIONS

(71) Applicant: AstraZeneca AB, Sodertalje (SE)

(72) Inventors: Paul Gellert, Macclesfield (GB); Kathryn Hill, Macclesfield (GB); Richard Storey, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 716 days.

This patent is subject to a terminal disclaimer.

(21) Appl. No.: 17/268,632

(22) PCT Filed: Aug. 15, 2019

(86) PCT No.: PCT/IB2019/056924
§ 371 (c)(1),
(2) Date: Feb. 16, 2021

(87) PCT Pub. No.: WO2020/035815
PCT Pub. Date: Feb. 20, 2020

(65) Prior Publication Data
US 2022/0273677 A1    Sep. 1, 2022

Related U.S. Application Data

(60) Provisional application No. 62/719,319, filed on Aug. 17, 2018.

(51) Int. Cl.
| | | |
|---|---|---|
| *A61K 31/635* | (2006.01) | |
| *A61K 9/19* | (2006.01) | |
| *A61K 47/59* | (2017.01) | |
| *A61P 35/00* | (2006.01) | |

(52) U.S. Cl.
CPC ........... *A61K 31/635* (2013.01); *A61K 9/19* (2013.01); *A61K 47/595* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 9,018,381 B2 | 4/2015 | Diebold | |
| 2009/0324535 A1* | 12/2009 | Boyd | A61K 47/595 424/78.17 |
| 2022/0273807 A1* | 9/2022 | Ashford | A61K 47/60 |

FOREIGN PATENT DOCUMENTS

| | | |
|---|---|---|
| WO | 2012167309 A1 | 12/2012 |
| WO | 2015035446 A1 | 3/2015 |
| WO | 2018154004 A1 | 8/2018 |

OTHER PUBLICATIONS

Sunil Kumar Parajapati et al: "Potential Application of Dendrimers in Drug Delivery: A Concise Review and Update", Journal of Drug Delivery and Therapeutics, vol. 6, No. 2, Mar. 15, 2016.
Amir Mohammed Alsharabasy: "Concise Review: Considerations for the Formulation, Delivery and Administration Routes of Biopharmaceuticals", Archives of Biotechnology and Biomedicine, vol. 1, No. 1, Apr. 1, 2017.
Fox M.E., et al., "Synthesis and In Vivo Antitumor Efficacy of PEGylated Poly(l-lysine) Dendrimer-Camptothecin Conjugates," Molecular Pharmaceutics, (Oct. 5, 2009), vol. 6, No. 5, 2009, pp. 1562-1572, XP055159694, DOI: 10.1021/mp9001206, ISSN 1543-8384.
Kaminskas L.M., et al., "Doxorubicin-Conjugated PEGylated Dendrimers Show Similar Tumoricidal Activity But Lower Systemic Toxicity When Compared to PEGylated Liposome and Solution Formulations in Mouse and Rat Tumor Models," Molecular Pharmaceutics, Mar. 5, 2012, vol. 9, No. 3, pp. 422-432, doi: 10.1021/mp200522d, ISSN 1543-8384, XP055159704.
Kaminskas L.M., et al., "Methotrexate-Conjugated PEGylated Dendrimers Show Differential Patterns of Deposition and Activity in Tumor-Burdened Lymph Nodes after Intravenous and Subcutaneous Administration in Rats," Molecular Pharmaceutics, Dec. 8, 2014, vol. 12, No. 2, pp. 432-443, https://doi.org/10.1021/mp500531e.
Kaminskas L.M., et al., "PEGylation of Polylysine Dendrimers Improves Absorption and Lymphatic Targeting Following SC Administration in Rats," Journal of Controlled Release, vol. 140, 2009, pp. 108-116, doi:10.1016/j.jconrel.2009.08.005.

* cited by examiner

*Primary Examiner* — Samantha L Shterengarts
*Assistant Examiner* — Jed A Kucharczk

(57) ABSTRACT

Disclosed are pharmaceutical compositions comprising a lyophilized compound of formula (I): (I) or a pharmaceutically acceptable salt thereof, and methods of using the same for treating cancer.

27 Claims, 10 Drawing Sheets

DENDRIMER FORMULATIONS

RELATED APPLICATIONS

This application is a U.S. National Stage application of International Application No. PCT/IB2019/056924, filed on Aug. 15, 2019, said International Application No. PCT/IB2019/056924 claims benefit under 35 U.S.C. 119(e) to U.S. Provisional Patent Application No. 62/719,319 filed on Aug. 17, 2018, the contents of which are hereby incorporated by reference in their entirety

BACKGROUND

Bcl-2 and Bcl-XL are important anti-apoptotic members of the BCL-2 family of proteins and master regulators of cell survival (Chipuk J E et al., The BCL-2 family reunion, *Mol. Cell* 2010 Feb. 12; 37(3):299-310). Gene translocation, amplification and/or protein over-expression of these critical survival factors has been observed in multiple cancer types and is widely implicated in cancer development and progression (Yip et al., Bcl-2 family proteins and cancer, *Oncogene* 2008 27, 6398-6406; and Beroukhim R. et al., The landscape of somatic copy-number alteration across human cancers, *Nature* 2010 Feb. 18; 463 (7283):899-905). In many malignancies, BCL-2 and/or BCL-XL have also been shown to mediate drug resistance and relapse and are strongly associated with a poor prognosis (Robertson L E et al. Bcl-2 expression in chronic lymphocytic leukemia and its correlation with the induction of apoptosis and clinical outcome, Leukemia 1996 March; 10(3):456-459; and Ilievska Poposka B. et al., Bcl-2 as a prognostic factor for survival in small-cell lung cancer, *Makedonska Akademija na Naukite i Umetnostite Oddelenie Za Bioloshki i Meditsinski Nauki Prilozi* 2008 December; 29(2):281-293).

Anti-apoptotic BCL2 family proteins promote cancer cell survival by binding to pro-apoptotic proteins like BIM, PUMA, BAK, and BAX and neutralizing their cell death-inducing activities (Chipuk J E et al., infra; and Yip et al, infra). Therefore, therapeutically targeting BCL-2 and BCL-XL alone or in combination with other therapies that influence the BCL-2 family axis of proteins, such as cytotoxic chemotherapeutics, proteasome inhibitors, or kinase inhibitors is an attractive strategy that may treat cancer and may overcome drug resistance in many human cancers (Delbridge, A R D et al., The BCL-2 protein family, BH3-mimetics and cancer therapy, *Cell Death & Differentiation* 2015 22, 1071-1080).

In addition to cell potency, in order to develop a candidate compound into a suitably acceptable drug product, the compound needs to possess and exhibit a host of additional properties. These include suitable physico-chemical properties to allow formulation into a suitable dosage form (e.g., solubility, stability, manufacturability), suitable biopharmaceutical properties (e.g., permeability, solubility, absorption, bioavailability, stability under biological conditions, pharmacokinetic and pharmacodynamic behavior) and a suitable safety profile to provide an acceptable therapeutic index. Identification of compounds, e.g., inhibitors of Bcl-2 and/or Bcl-XL that exhibit some or all of such properties is challenging.

Particular N-acylsulfonamide based inhibitors of Bcl-2 and/or Bcl-XL and methods for making the same are disclosed in U.S. Pat. No. 9,018,381. The activity and specificity of the compounds that bind to and inhibit Bcl-2 function in a cell has also been disclosed in U.S. Pat. No. 9,018,381 by way of in vitro binding and cellular assays. However, delivery of these N-acylsulfonamide based inhibitors of Bcl-2 and/or Bcl-XL have proved difficult due to for example, low solubility and target related side effects. Applicants have developed dendrimers linked to a certain Bcl-2/XL inhibitor (Compound A, the synthesis of which is described in U.S. Pat. No. 9,018,381) that may overcome the delivery challenges faced by the unconjugated Bcl inhibitors:

(Compound A)

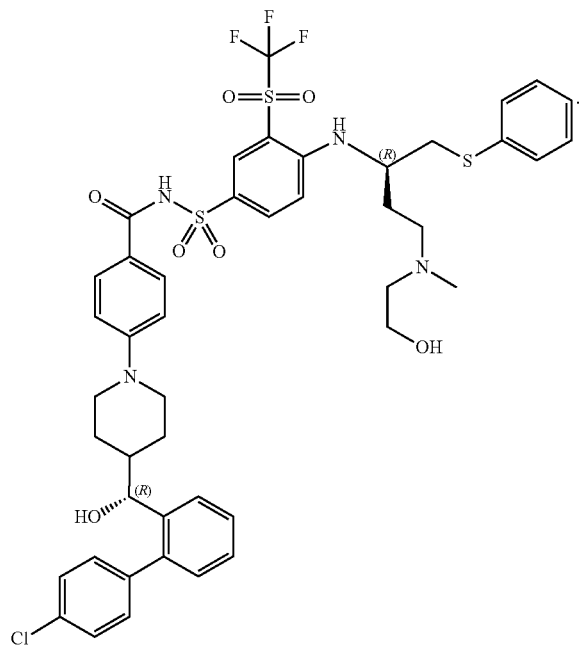

Applicants have found that formulating such dendrimers comprising Compound A has been challenging due to stability issues, such as cleavage of Compound A from the dendrimer during formulation and storage. Applicants have therefore developed pharmaceutical compositions and methods of making such pharmaceutical compositions that minimize impurities, including the amount of cleaved (free) Compound A.

SUMMARY

Disclosed herein are pharmaceutical compositions comprising lyophilized dendrimers covalently attached (e.g., conjugated, or linked) to a Bcl inhibitor. The conjugated dendrimers exhibit high solubility compared to the unconjugated Bcl inhibitor, and preclinical data suggests that the dendrimers conjugated with the Bcl inhibitor have the potential to improve tolerability in vivo, which may improve therapeutic index and reduce side effects. The disclosed pharmaceutical compositions exhibit good solubility in a pharmaceutically acceptable diluent or solvent, as well as minimal impurities generated during formulation and storage.

In some embodiments, disclosed are pharmaceutical compositions comprising a lyophilized dendrimer of formula (I)

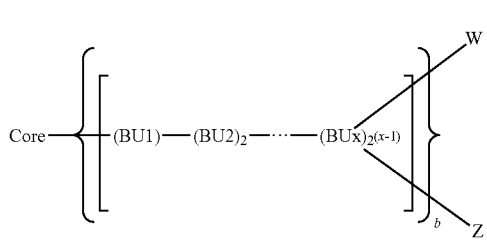
(I)

or a pharmaceutically acceptable salt thereof, wherein:
Core is

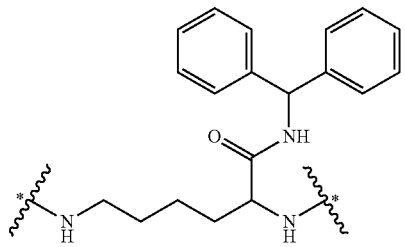 [SMILES: *NCCCCC(N*)C(=O)NC(c1ccccc1)c1ccccc1]

* indicates covalent attachment to a carbonyl moiety of (BU1);
b is 2;
BU are building units;
$BU_x$ are building units of generation x, wherein the total number of building units in generation x of the dendrimer of formula (I) is equal to $2^{(x)}$ and the total number of BU in the dendrimer of formula (I) is equal to $(2^x-1)b$; wherein BU has the following structure:

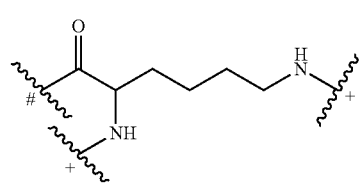 [SMILES: *NCCCCC(N*)C(*)=O]

\# indicates covalent attachment to an amine moiety of Core or an amino moiety of BU;
+ indicates a covalent attachment to a carbonyl moiety of BU or a covalent attachment to W or Z;
W is independently $(PM)_c$ or $(H)_e$;
Z is independently $(L-AA)_d$ or $(H)_e$;
PM is $PEG_{1800-2400}$;
L-AA is a linker covalently attached to an active agent; wherein L-AA is of the formula:

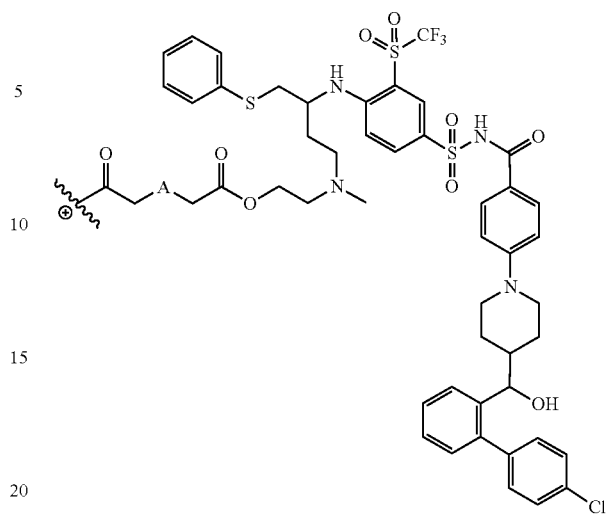

wherein
A is —N(CH$_3$) or —S—;
⊕ is the attachment point to an amine moiety of BUx;
provided that $(c+d) \leq (2^x)b$ and d is $\leq 1$; and
provided that if $(c+d)<(2^x)b$, then any remaining W and Z groups are $(H)_e$, wherein e is $[(2^x)b]-(c+d)$.

In some embodiments, disclosed are pharmaceutical compositions comprising a lyophilized dendrimer of formula (II):

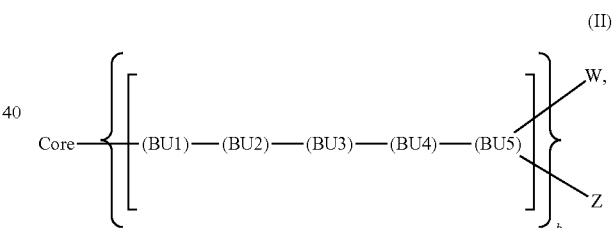
(II)

or a pharmaceutically acceptable salt thereof, wherein
b is 2;
Core is

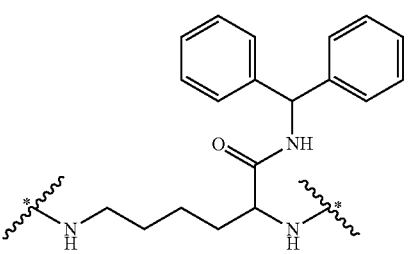 [SMILES: *NCCCCC(N*)C(=O)NC(c1ccccc1)c1ccccc1]

* indicates covalent attachment to a carbonyl moiety of (BU1);
BU are building units and the number of BU is equal to 62; wherein BU has the following structure:

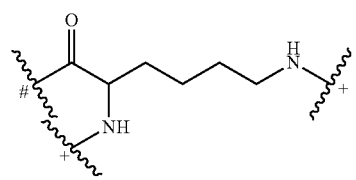 [SMILES: *NCCCCC(N*)C(*)=O]

# indicates covalent attachment to an amine moiety of Core or an amino moiety of BU, and + indicates a covalent attachment to a carbonyl moiety of BU or a covalent attachment to W or Z;

W is independently $(PM)_c$ or $(H)_e$;
Z is independently $(L-AA)_d$ or $(H)_e$;

Core is

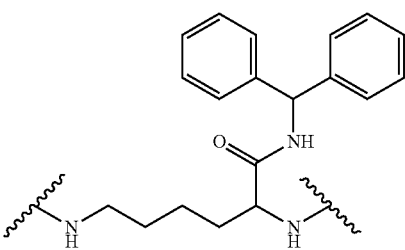 [SMILES: *NCCCCC(N*)C(=O)NC(c1ccccc1)c1ccccc1]

D is

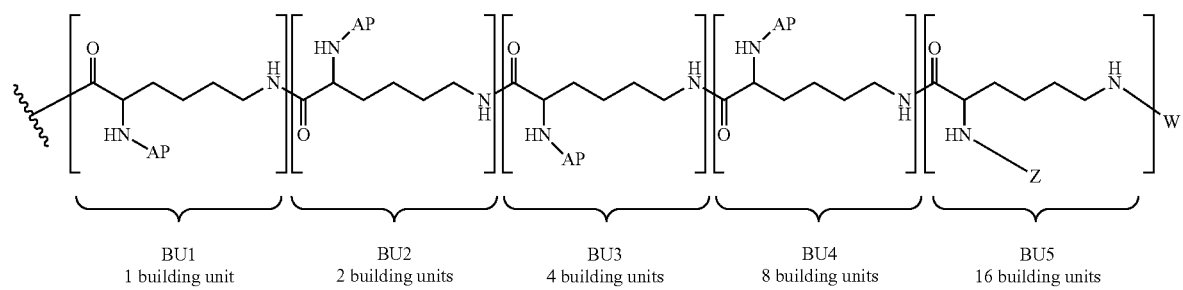

| BU1 | BU2 | BU3 | BU4 | BU5 |
|---|---|---|---|---|
| 1 building unit | 2 building units | 4 building units | 8 building units | 16 building units |

PM is $PEG_{1800-2400}$;
L-AA is a linker covalently attached to an active agent; wherein L-AA is of the formula:

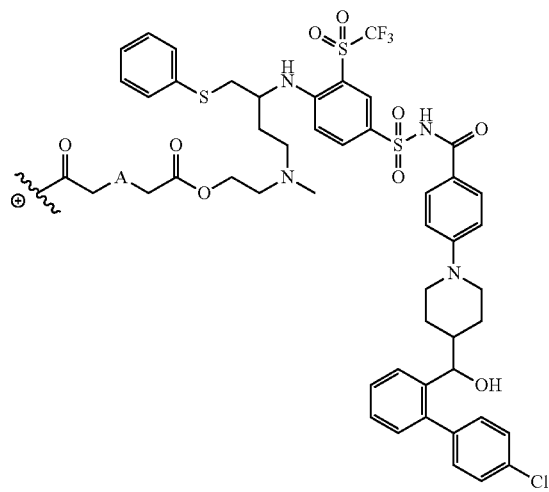

wherein
A is —N(CH$_3$) or —S—;
⊕ indicates covalent attachment to an amine moiety of BU5;
provided that (c+d) is ≤64 and d is 1; and
provided that if (c+d)<64, then any remaining W and Z groups are $(H)_e$, wherein e is 64-(c+d).

In some embodiments, disclosed are pharmaceutical compositions comprising a lyophilized dendrimer of formula (III):

D-Core-D     (III)

or a pharmaceutically acceptable salt thereof, wherein

AP is an attachment point to another building unit;
W is independently $(PM)_c$ or $(H)_e$;
Z is independently $(L-AA)_d$ or $(H)_e$;
PM is $PEG_{1800-2400}$;
L-AA is a linker covalently attached to an active agent; wherein L-AA is of the formula:

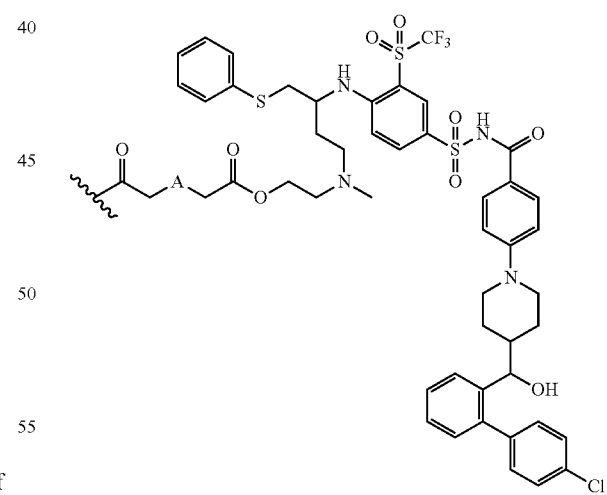

wherein
A is —N(CH$_3$), —O—, —S— or —CH$_2$—;
provided that if (c+d)<64, then any remaining W and Z groups are $(H)_e$, wherein e is 64-(c+d); and d is ≥1.

In some embodiments, disclosed are pharmaceutical compositions comprising a lyophilized dendrimer of formula (IV):

(IV)
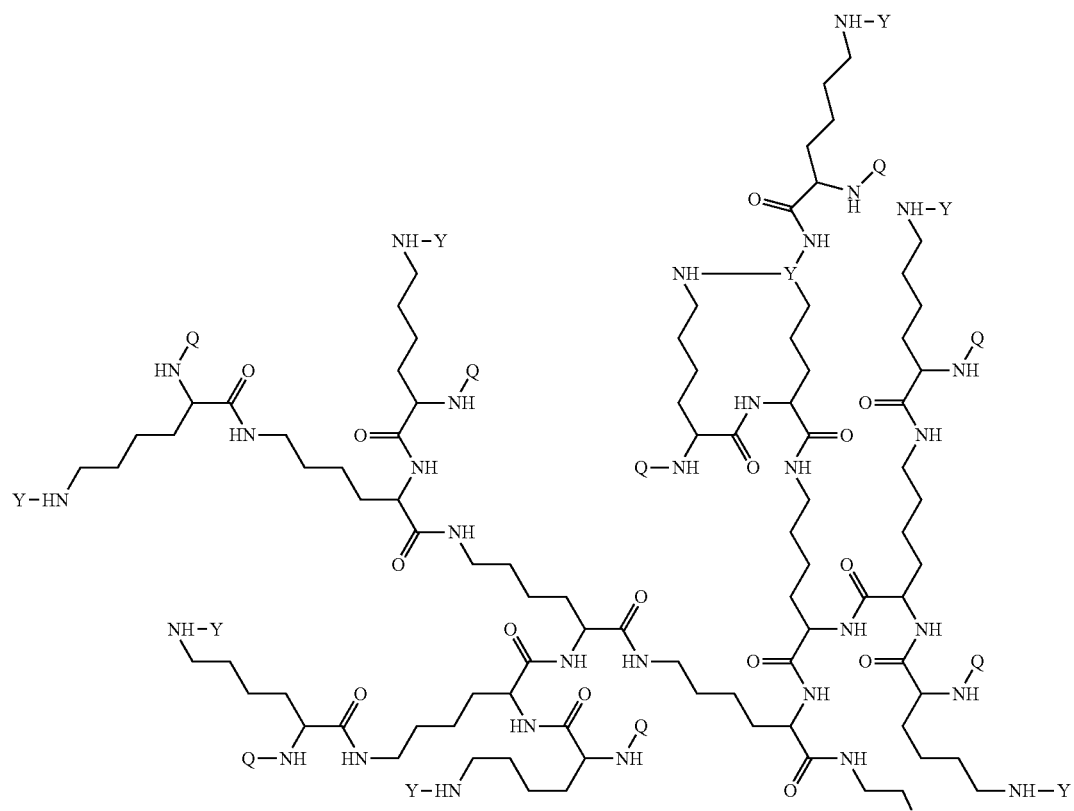
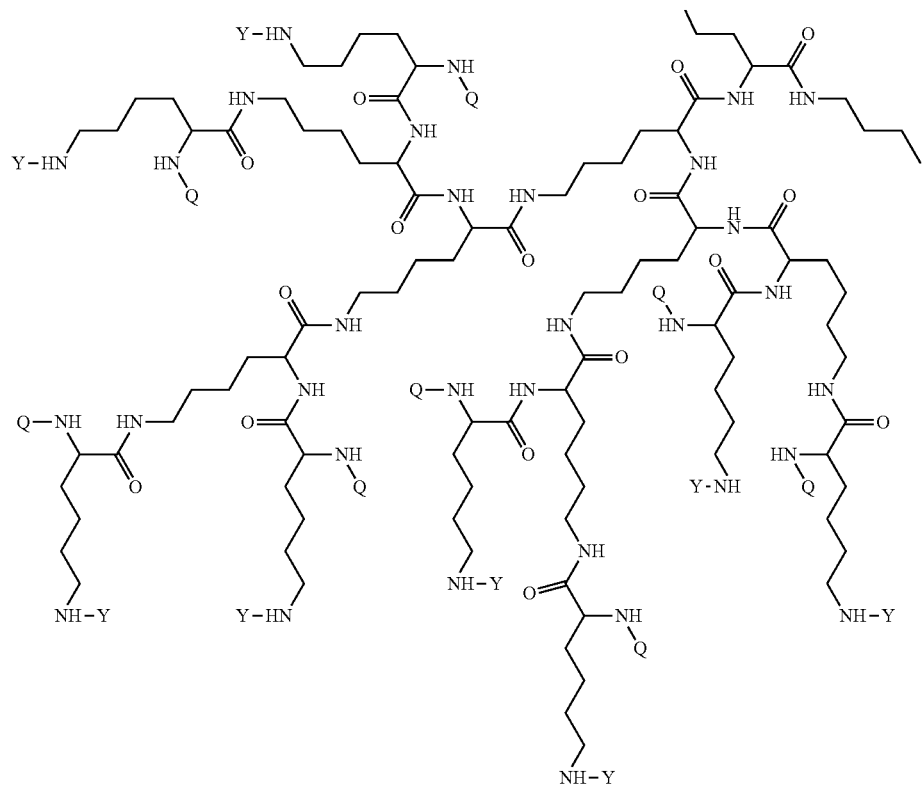

-continued
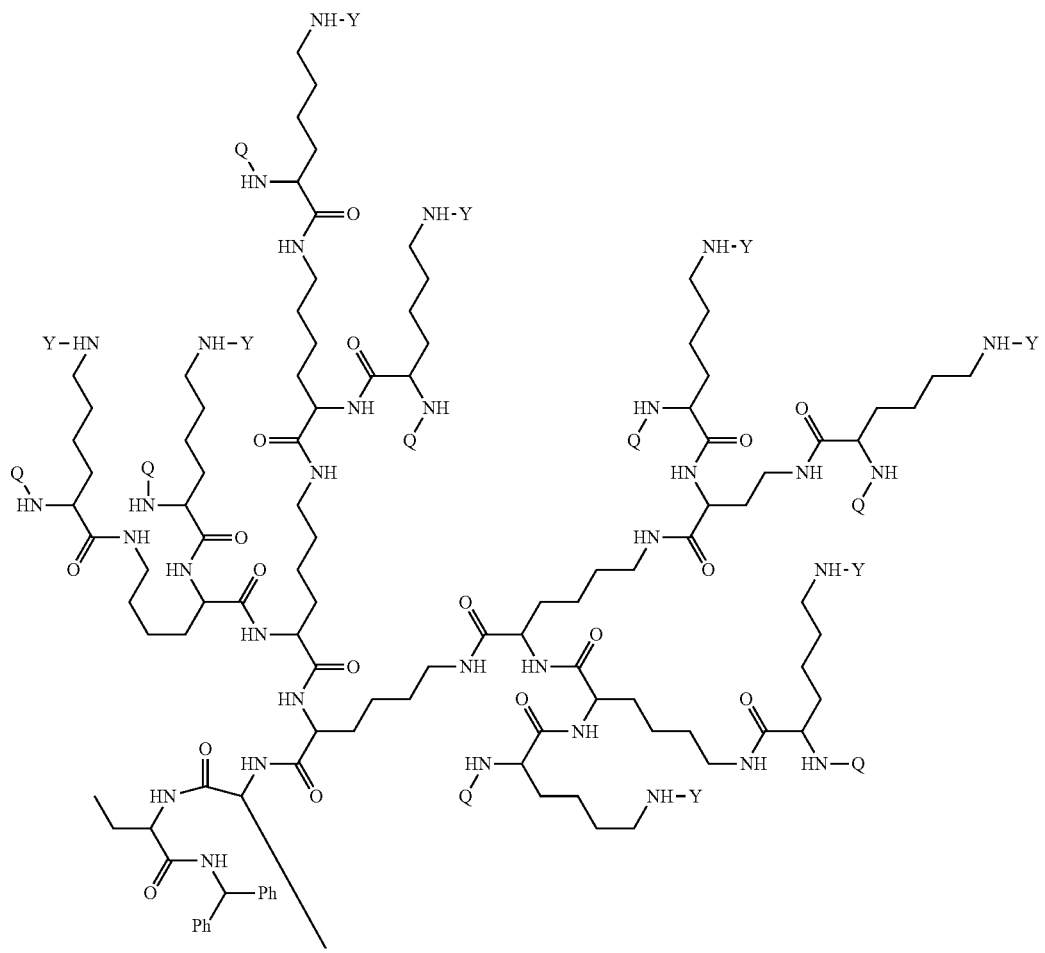

-continued
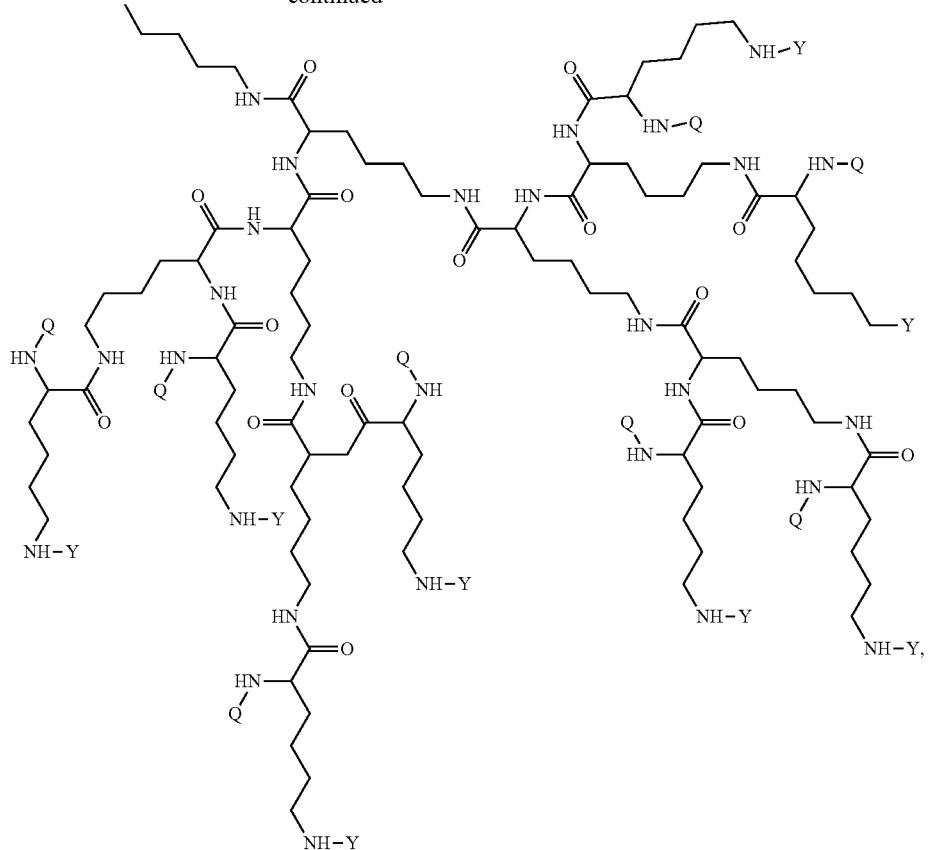
35
or a pharmaceutically acceptable salt thereof, wherein Y is $PEG_{1800-2400}$ or H; Q is H or L-AA, in which L-AA has the structure:
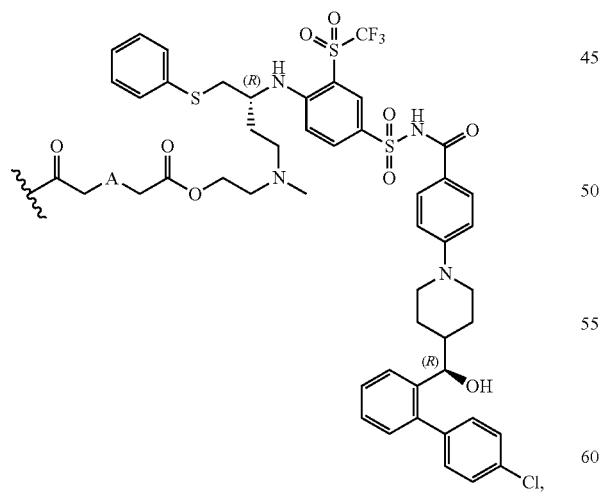
A is —S— or —N(CH₃), provided that if the sum of $PEG_{1800-2400}$ and L-AA is less than 64, the remaining Q and Y moieties are H, and provided that at least one Q is L-AA.

In some embodiments, disclosed are pharmaceutical compositions comprising a lyophilized dendrimer of formula (V):
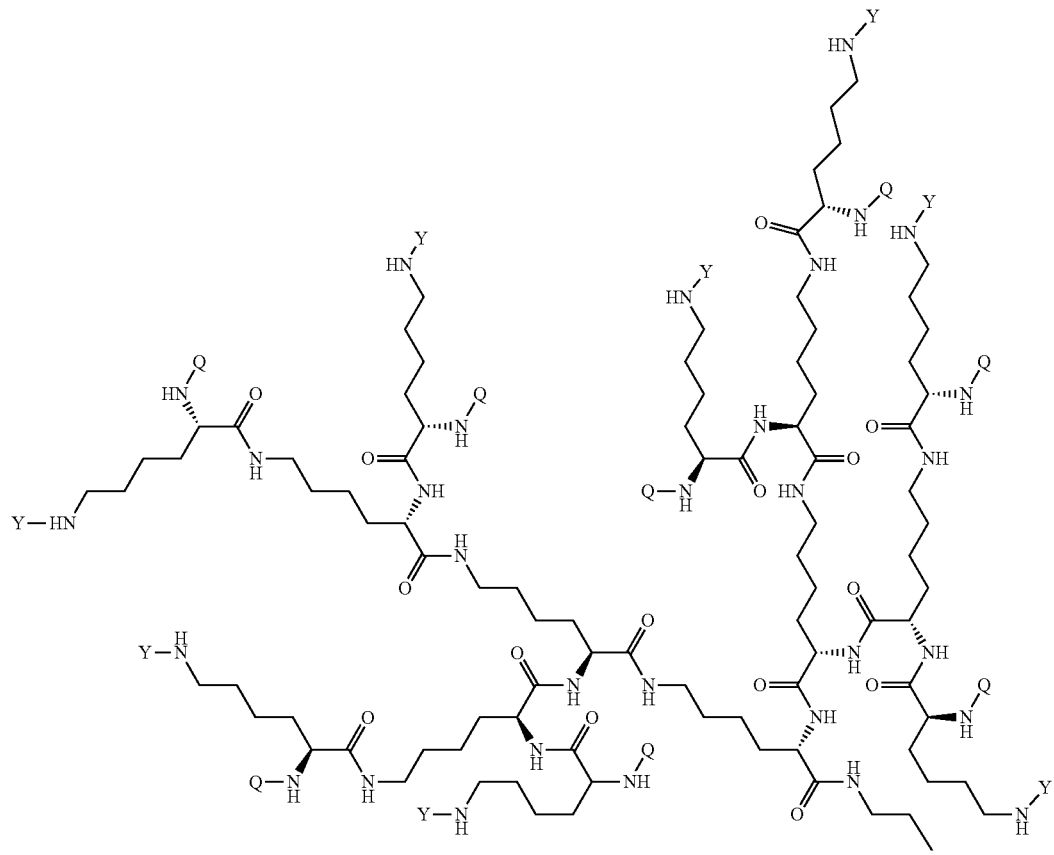

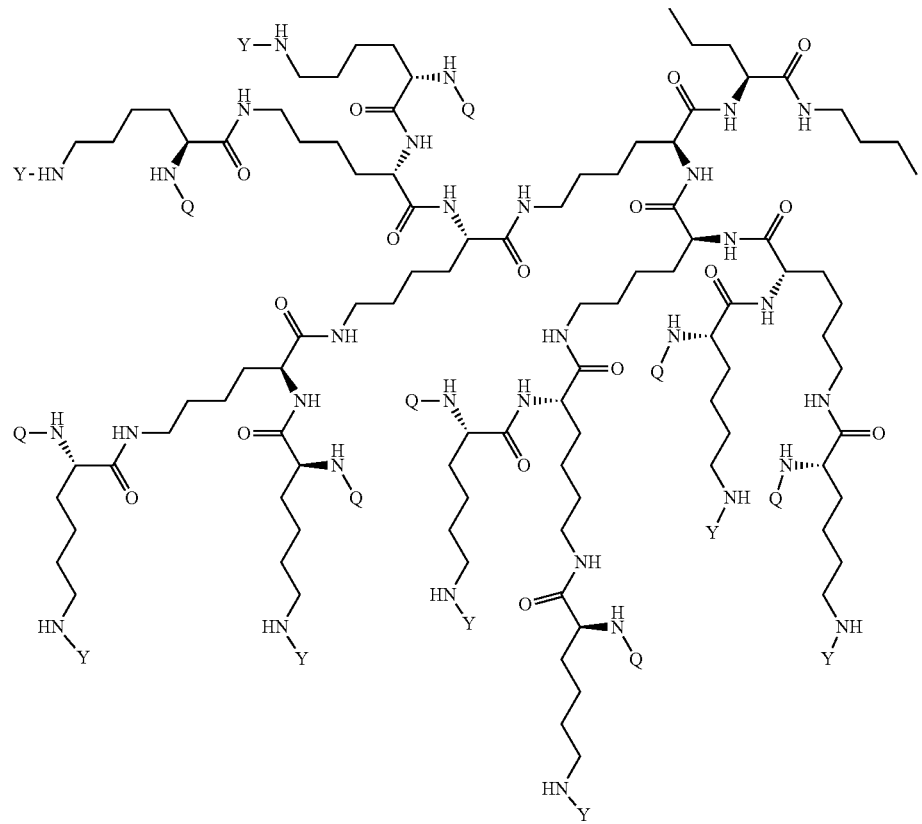

-continued
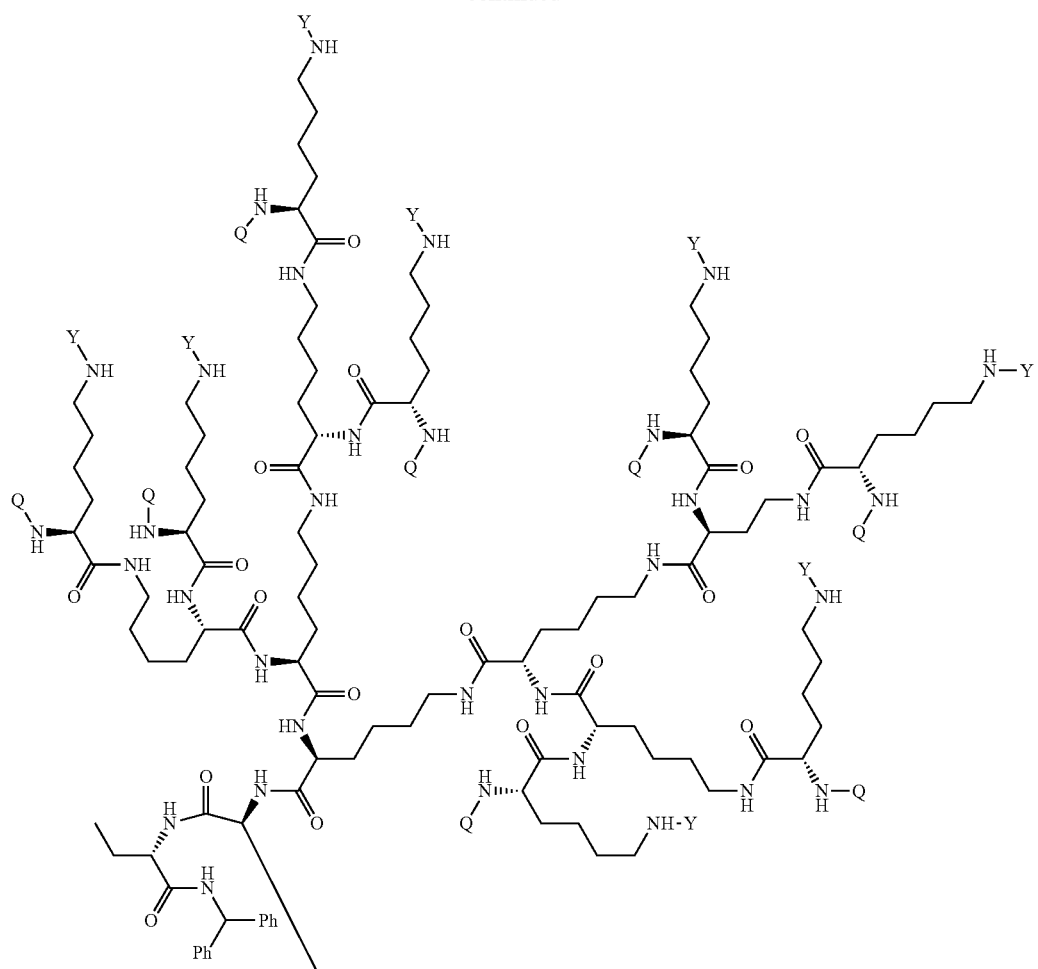

-continued
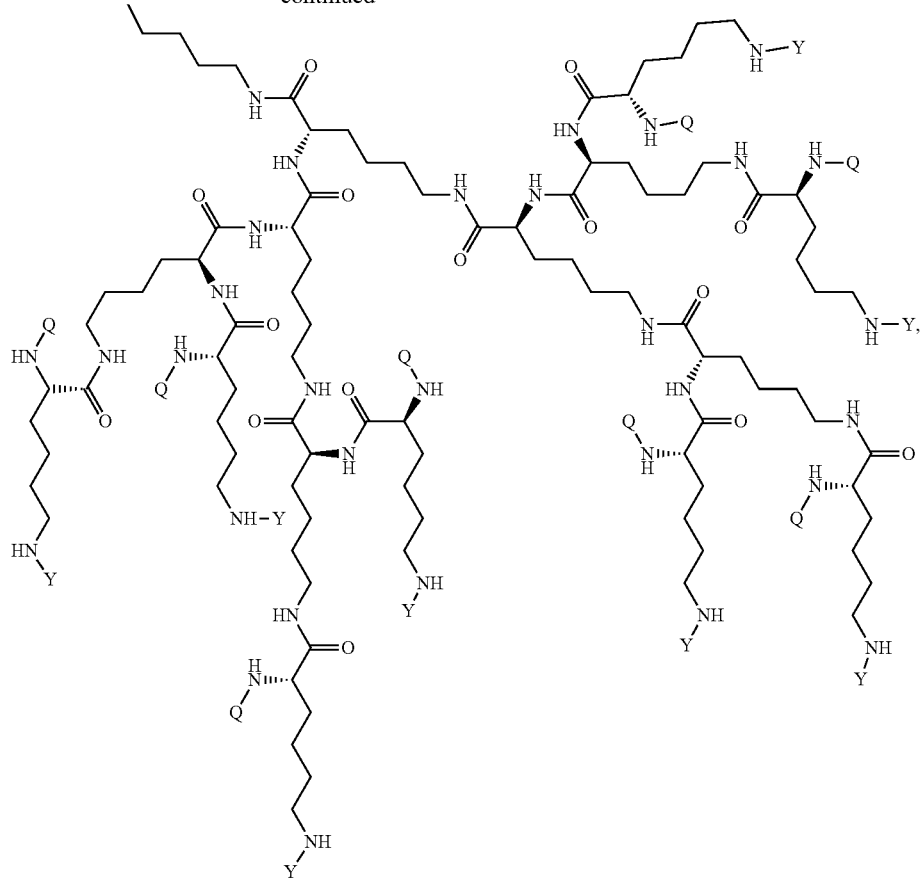
or a pharmaceutically acceptable salt thereof, wherein
Y is PEG$_{1800-2400}$ or H;
Q is H or L-AA, wherein L-AA has the structure:
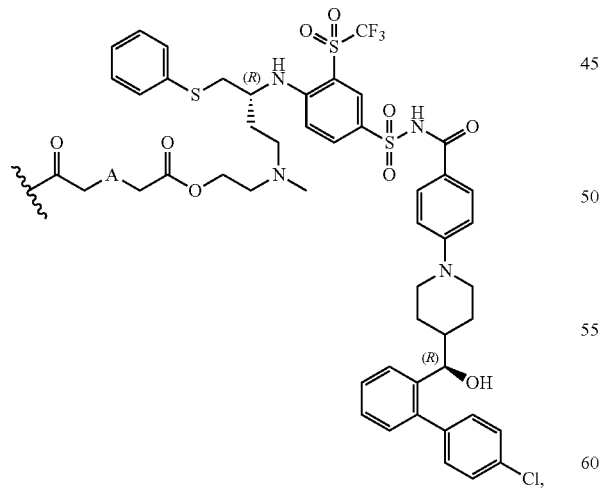
A is —S— or —N(CH$_3$), provided that if the sum of PEG$_{1800-2400}$ and L-AA is less than 64, the remaining Q and Y moieties are H, and provided that at least one Q is L-AA.

In some embodiments, disclosed are pharmaceutical compositions comprising a lyophilized dendrimer of formula (VI):
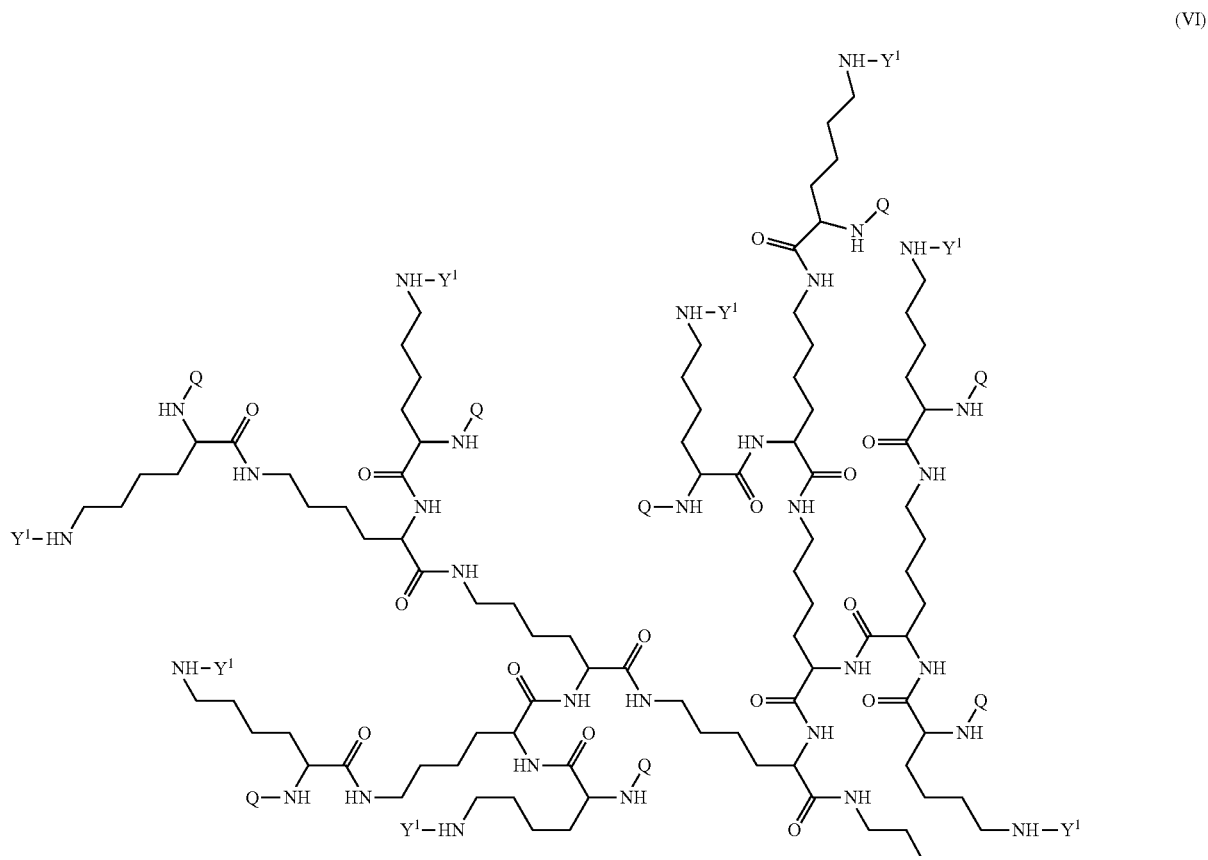
(VI)

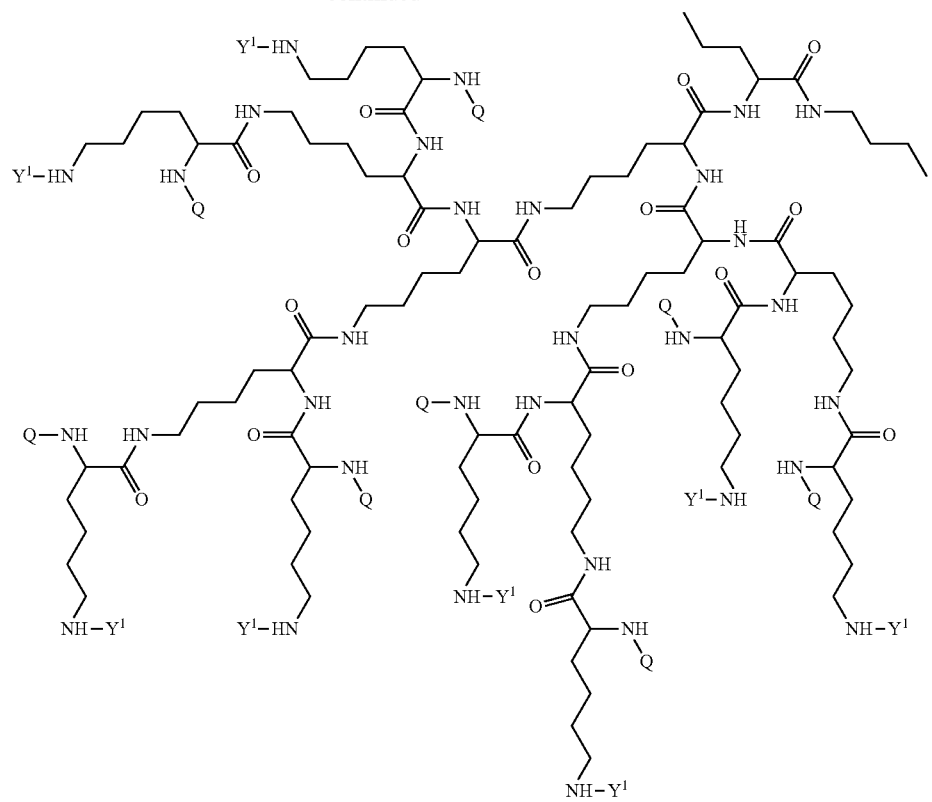

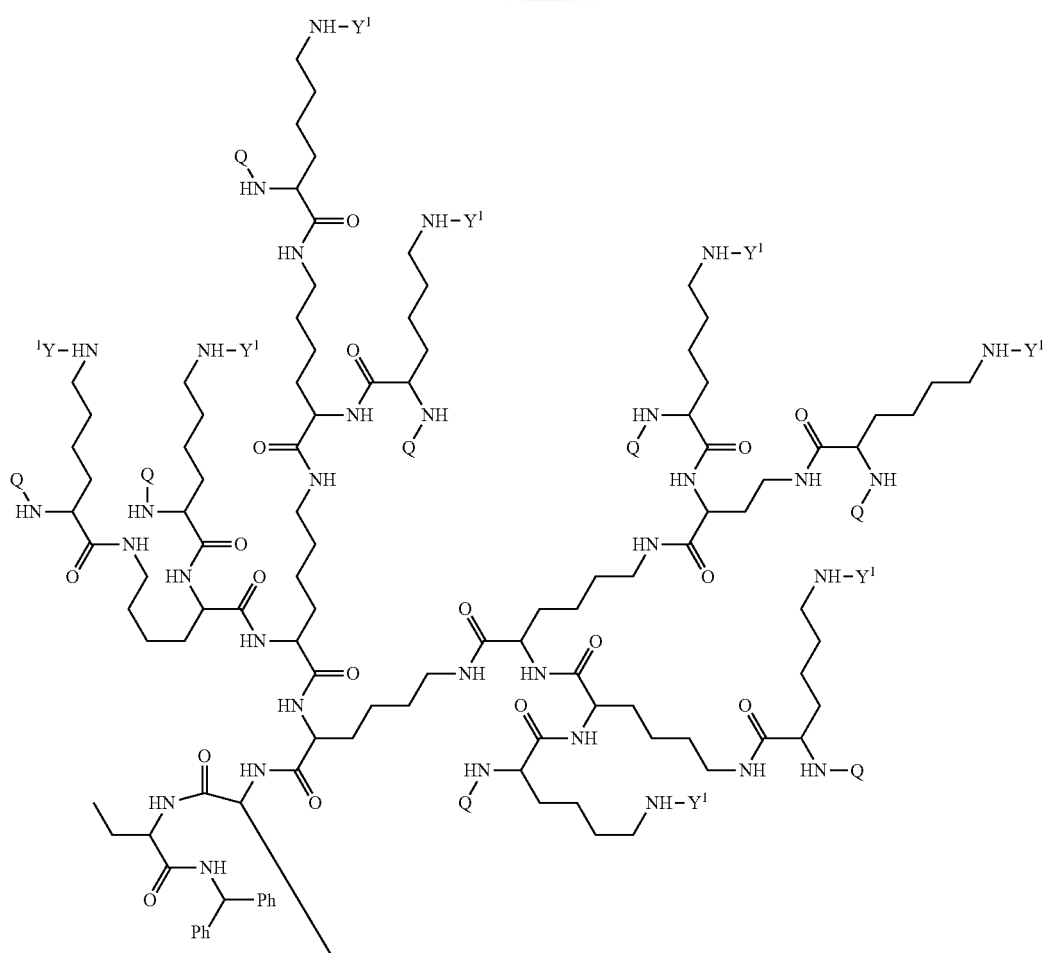

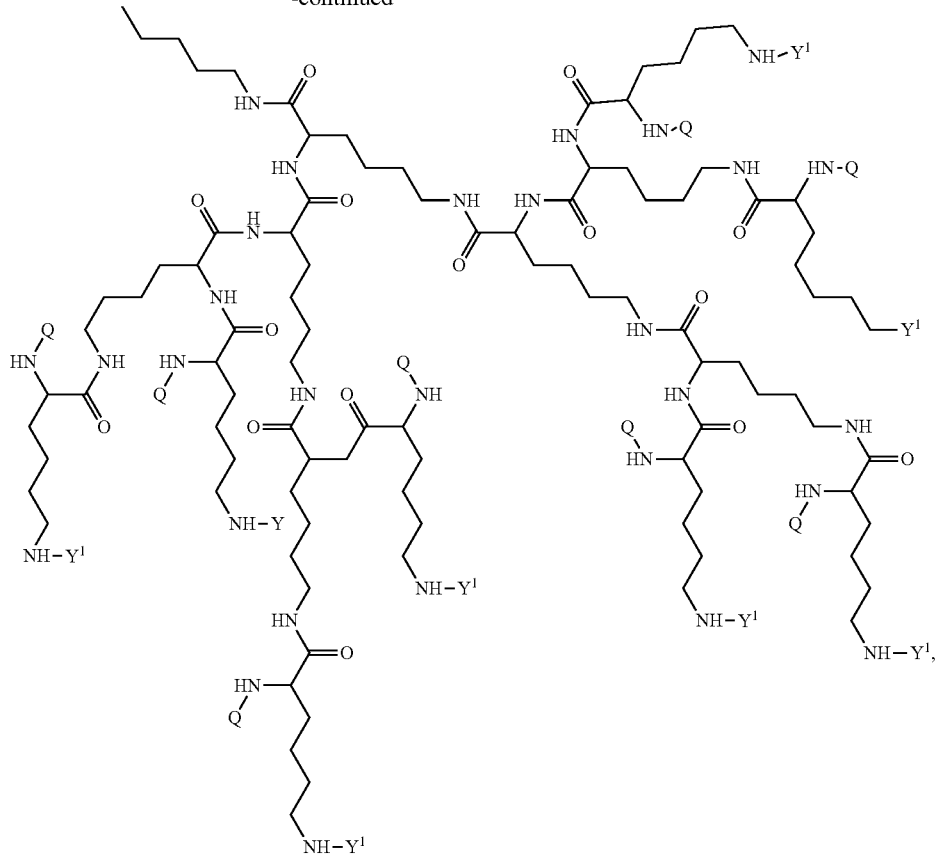

35 or a pharmaceutically acceptable salt thereof, wherein
$Y^1$ is —C(=O)CH$_2$—(OCH$_2$CH$_2$)$_x$—OCH$_3$ or H;
x is an integer from between 39 and 53; and
Q is H or L-AA, in which L-AA has the structure:

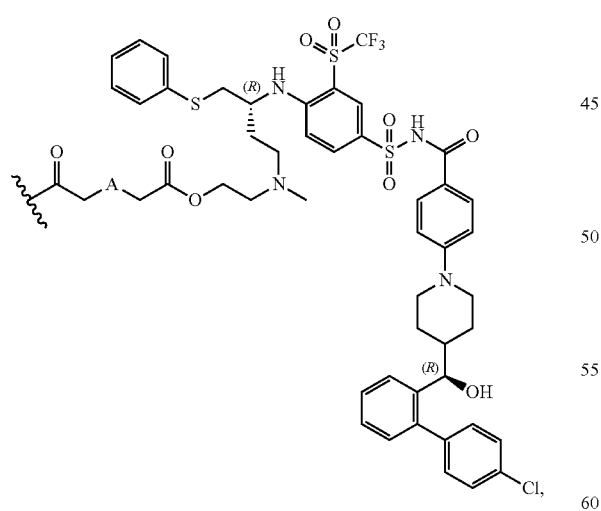

A is —S— or —N(CH$_3$), provided that if the sum of $Y^1$ and L-AA is less than 64, the remaining Q and $Y^1$ moieties are H, and provided that at least one Q is L-AA. In some embodiments, disclosed is the compound of formula (VI) in which A is —S—. In some embodiments, disclosed is the compound of formula (VI) in which A is —N(CH$_3$).

In some embodiments, disclosed are pharmaceutical compositions comprising a lyophilized dendrimer of formula (VII):
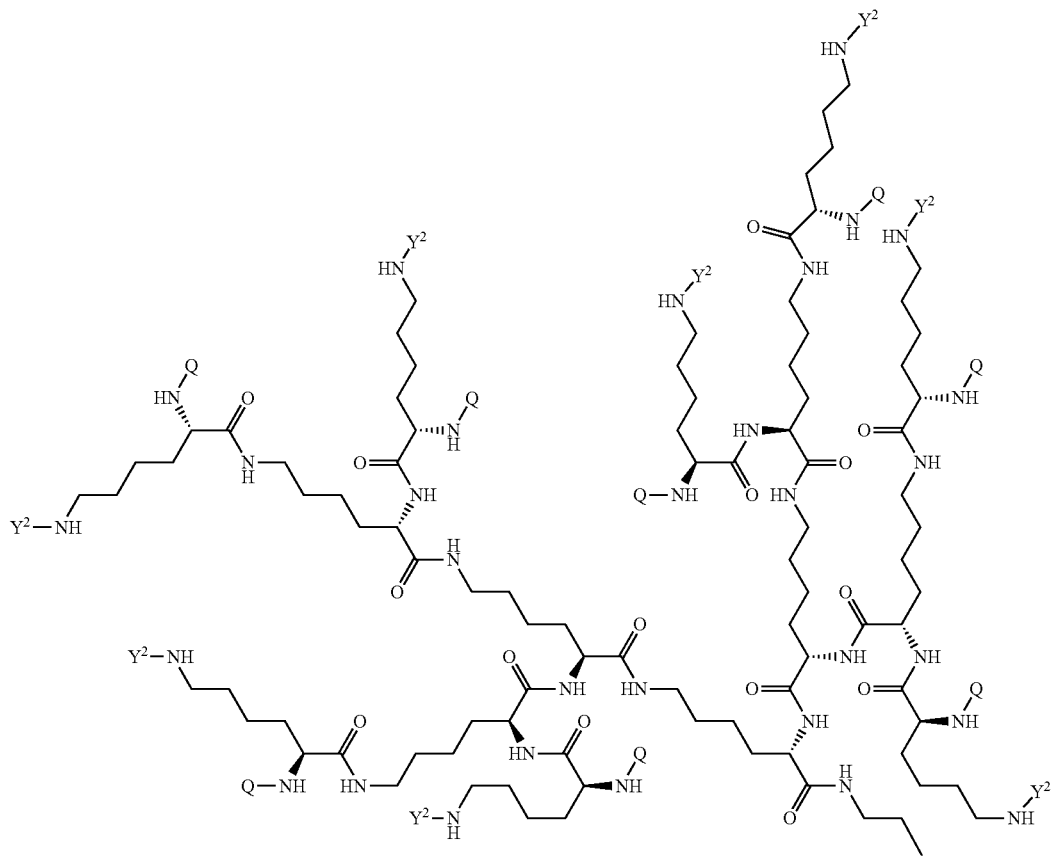
(VII)

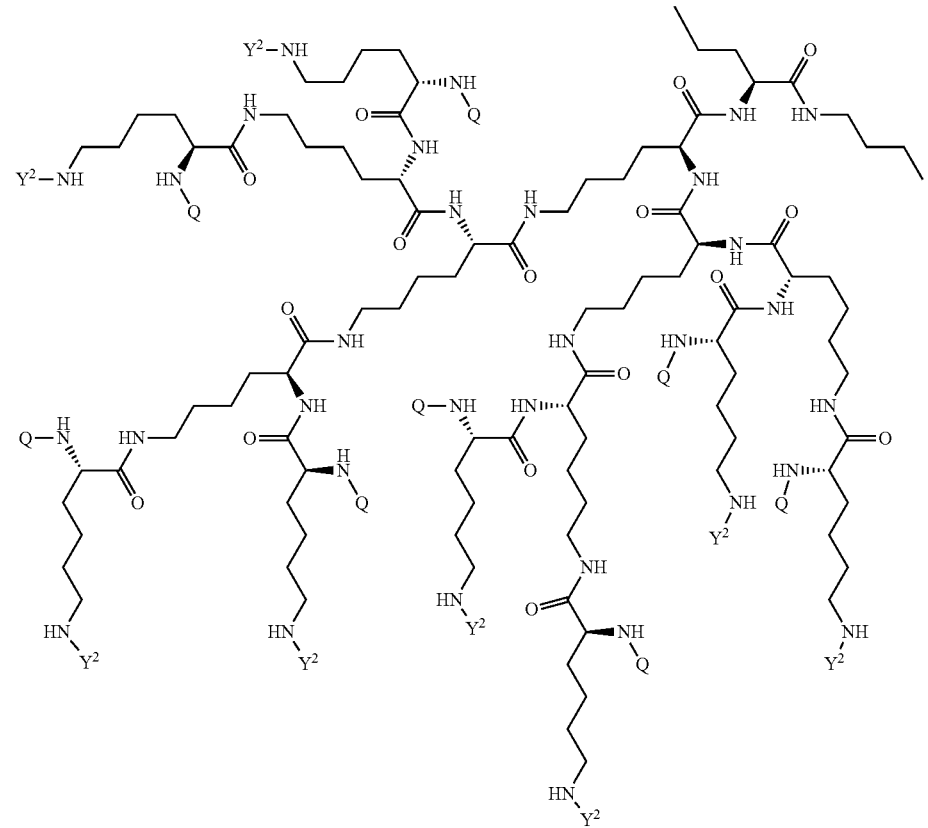

-continued
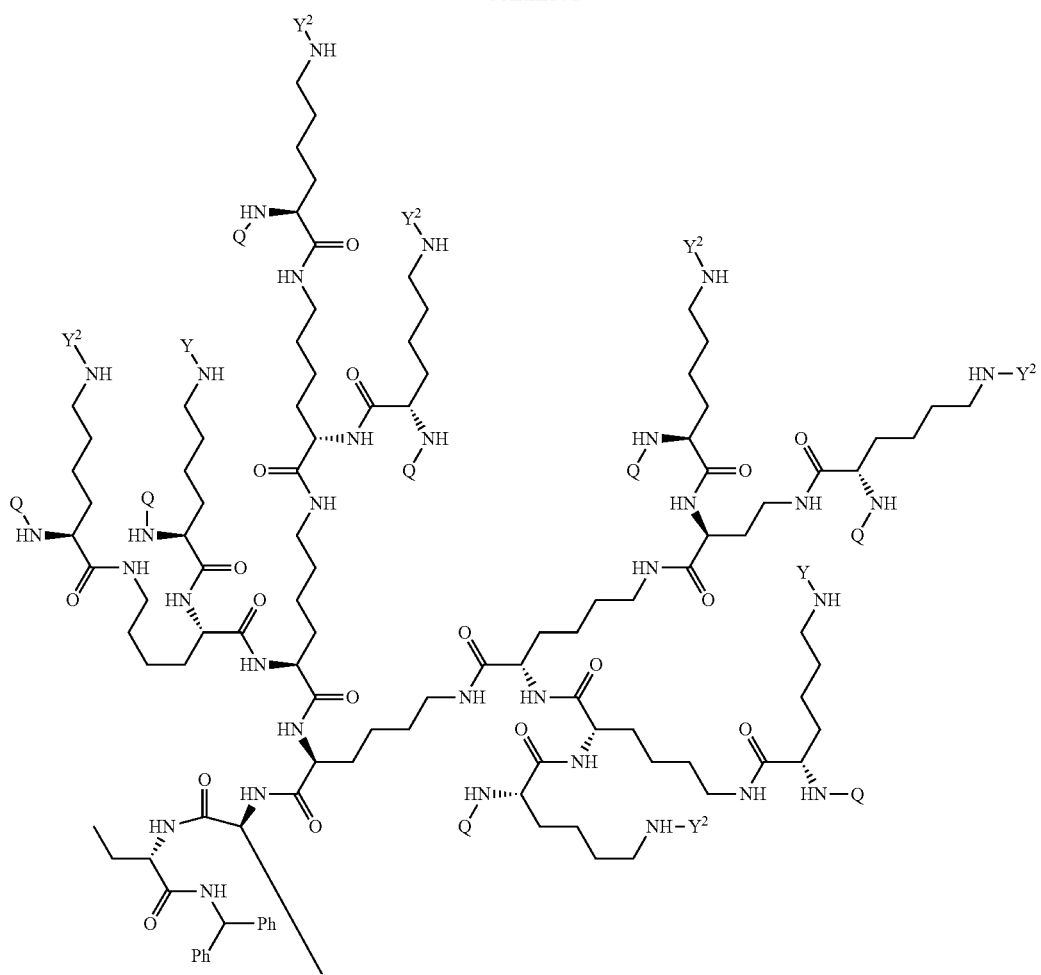

-continued

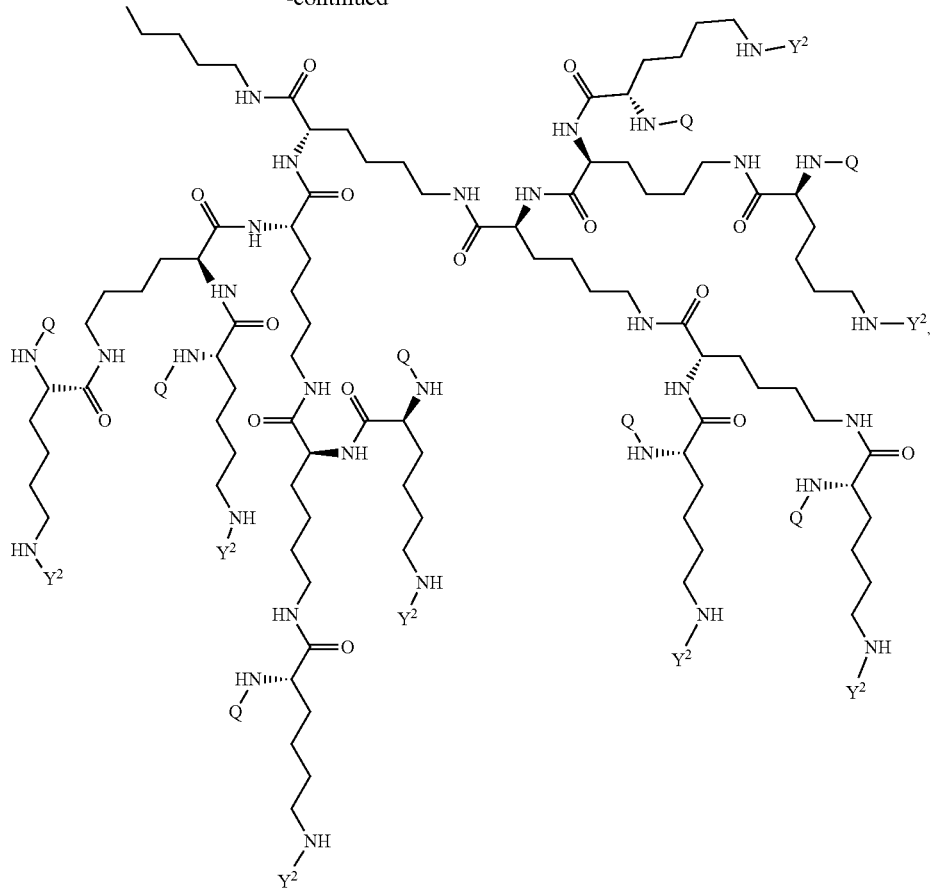

or a pharmaceutically acceptable salt thereof, wherein
$Y^2$ is —C(=O)CH$_2$—(OCH$_2$CH$_2$)$_y$—OCH$_3$ or H;
y is an integer from between 39 and 53; and
Q is H or L-AA, in which L-AA has the structure:

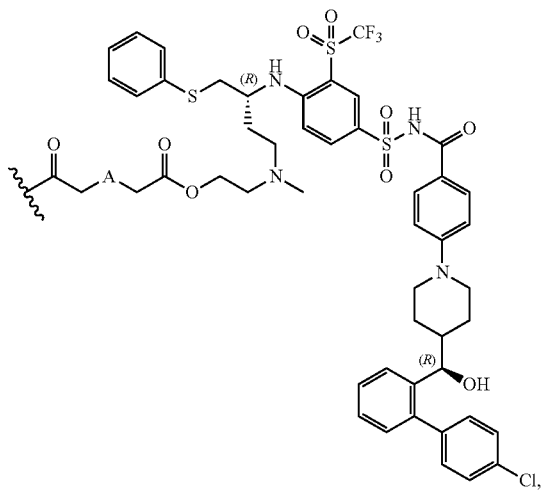

A is —S— or —N(CH$_3$), provided that if the sum of $Y^2$ and L-AA is less than 64, the remaining Q and $Y^2$ moieties are H, and provided that at least one Q is L-AA. In some embodiments, disclosed is the compound of formula (VII) in which A is —S—. In some embodiments, disclosed is the compound of formula (VII) in which A is —N(CH$_3$).

In some embodiments, disclosed are pharmaceutical compositions comprising a lyophilized dendrimer of formula (I), (II), (III), (IV), (V), (VI) or (VII), or a pharmaceutically acceptable salt thereof, prepared by the process comprising the steps of dissolving the compound of formula (I), (II), (III), (IV), (V), (VI) or (VII), or a pharmaceutically acceptable salt thereof, in glacial acetic acid to form a solution, freeze drying the solution and subliming the acetic acid at reduced pressure.

In some embodiments, disclosed are methods of treating cancer comprising intravenously administering to a subject in need thereof a pharmaceutical composition comprising an effective amount of a lyophilized dendrimer of formula (I), (II), (III), (IV), (V), (VI) or (VII), or a pharmaceutically acceptable salt thereof, and a pharmaceutically acceptable diluent or solvent.

In some embodiments, disclosed is the use of a pharmaceutical composition comprising a lyophilized dendrimer of formula (I), (II), (III), (IV), (V), (VI) or (VII), or a pharmaceutically acceptable salt thereof, in treating cancer.

In some embodiments, disclosed is the use of a pharmaceutical composition comprising a lyophilized dendrimer of formula (I), (II), (III), (IV), (V), (VI) or (VII), or a pharmaceutically acceptable salt thereof, for use in the manufacture of a medicament for treating cancer.

In some embodiments, disclosed is a kit of part comprising one or more containers comprising a pharmaceutical composition comprising a lyophilized dendrimer of formula (I), (II), (III), (IV), (V), (VI) or (VII), or a pharmaceutically acceptable salt thereof, and instructions for use.

DETAILED DESCRIPTION

Figure 1:
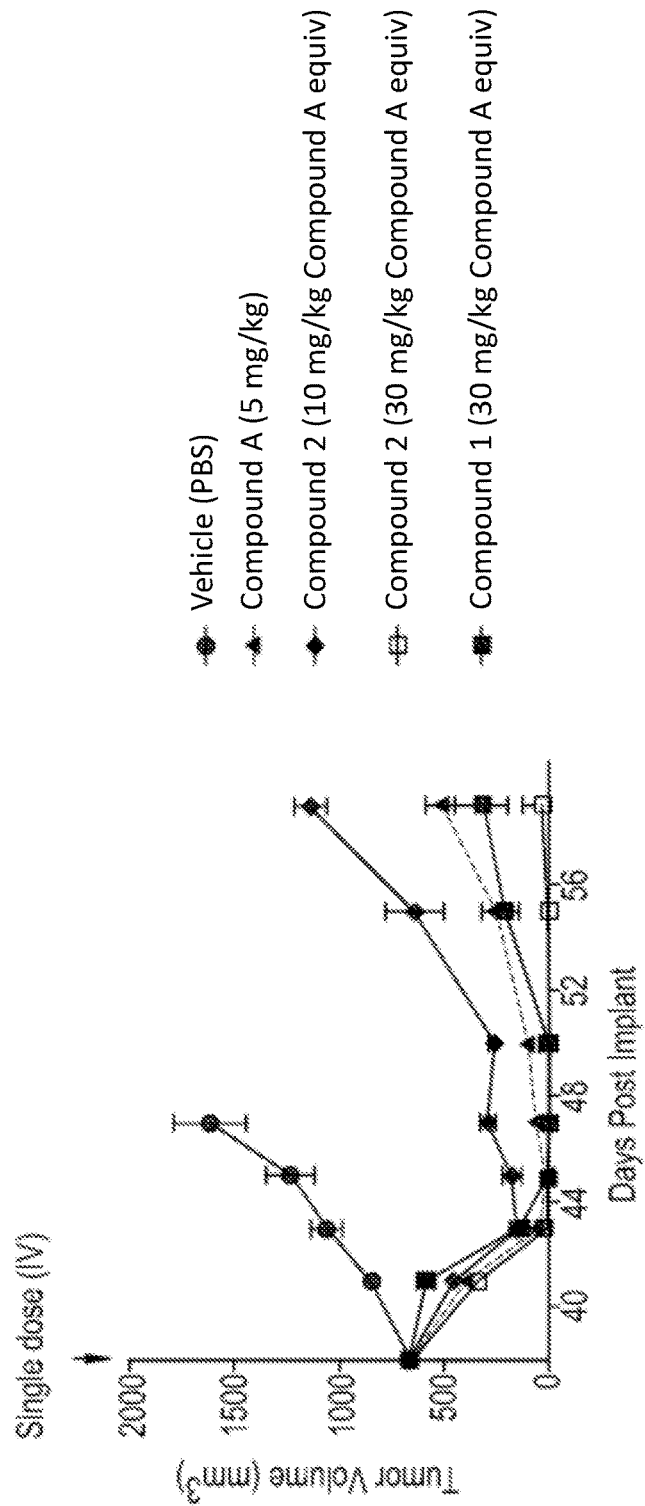
FIG. 1 displays an Acute Lymphoblastic Leukemia (ALL) Xenograft model in SCID mice using human acute lymphoblastic leukemia cells (RS4:11) for various macromolecules of the present invention. The efficacy evaluation of the vehicle (phosphate buffer saline), Compound A (formulated in 30% HP-β-CD, pH 4), Compound 1 in PBS (equivalent to 10 mg/kg Compound A) and Compound 2 in PBS (equivalent to 10 mg/kg and 30 mg/kg Compound A) is shown.

In some embodiments, disclosed are pharmaceutical compositions comprising a lyophilized dendrimer of formula (I)

$$\left\{ \text{Core} \left[ (BU1) - (BU2)_2 - \cdots - (BUx)_2^{(x-1)} \begin{matrix} W \\ \\ Z \end{matrix} \right] \right\}_b \quad (I)$$

or a pharmaceutically acceptable salt thereof, wherein:

Core is

[structure]

* indicates covalent attachment to a carbonyl moiety of (BU1);

b is 2;

BU are building units;

$BU_x$ are building units of generation x, wherein the total number of building units in generation x of the dendrimer of formula (I) is equal to $2^{(x)}$ and the total number of BU in the dendrimer of formula (I) is equal to $(2^x-1)b$; wherein BU has the following structure:

[structure]

# indicates covalent attachment to an amine moiety of Core or an amino moiety of BU;

+ indicates a covalent attachment to a carbonyl moiety of BU or a covalent attachment to W or Z;

W is independently $(PM)_c$ or $(H)_e$;

Z is independently $(L-AA)_d$ or $(H)_e$;

PM is $PEG_{1800-2400}$;

L-AA is a linker covalently attached to an active agent; wherein L-AA is of the formula:

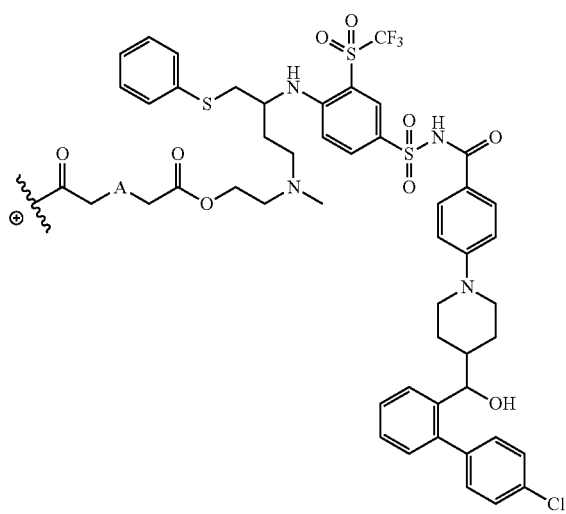

wherein

A is —N(CH$_3$) or —S—;

⊕ is the attachment point to an amine moiety of BUx;

provided that (c+d) s (2$^x$)b and d is 1; and provided that if (c+d)<(2$^x$)b, then any remaining W and Z groups are (H)$_e$, wherein e is [(2$^x$)b]−(c+d).

It will be appreciated that the core of the dendrimer represents the central unit from which the dendrimer is built. In this regard, the core represents the central unit from which the first and subsequent generations of building units are 'grown off'. In one embodiment, the Core in any of the dendrimers of formula (I), (II), (III), (IV), (V), (VI) or (VII) is

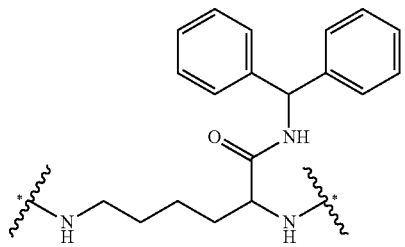 [SMILES: *NCCCCC(N*)C(=O)NC(c1ccccc1)c1ccccc1]

wherein * indicates a covalent attachment to the building units of the dendrimer. In some embodiments, Core in any of the dendrimers of formula (I), (II), (III), (IV), (V), (VI) or (VII) is

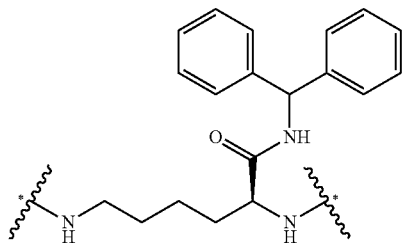

wherein * indicates a covalent attachment to the building units of the dendrimer.

The term "building unit" or "BU" includes molecules having at least three functional groups, one for attachment to the core or a building unit in a previous generation (or layer) of building units and two or more functional groups for attachment to building units in the next generation (or layer) of building units. The building units are used to build the dendrimer layers, by addition to the core or previous layer of building units. In some embodiments the building units have three functional groups.

The term "generation" includes the number of layers of building units that make up a dendron or dendrimer. For example, a one generation dendrimer will have one layer of building units attached to the core, for example, Core-[[building unit]b, where b is the number of dendrons attached to the core and the valency of the core. A two-generation dendrimer has two layers of building units in each dendron attached to the core. For example, when the building unit has one bivalent branch point, the dendrimer may be: Core[[building unit][building unit]2]b, a three generation dendrimer has three layers of building units in each dendron attached to the core, for example Core-[[building unit][building unit]2[building unit]4]b, a five generation dendrimer has five layers of building units in each dendron attached to the core, for example, Core-[[building unit][building unit]2[building unit]4[building unit]8[building unit]16]b, a 6 generation dendrimer has six layers of building units attached to the core, for example, Core-[[building unit][building unit]2[building unit]4[building unit]8[building unit]16[building unit]32]b, and the like. The last generation of building units (the outermost generation) provides the surface functionalization of the dendrimer and the number of surface functional groups available for binding the pharmacokinetic modifying group (PM) and/or linker and active agent (L-AA).

The term "surface functional groups" refers to the unreacted functional groups that are found in the final generation of the building units. In some embodiments, the number of surface functional groups are equal to (2$^x$)b, in which x is the number of generations in the dendrimer and b is the number of dendrons. In some embodiments, the surface functional groups are primary amino functional groups.

The total number of building units in a dendrimer with building units having 3 functional groups (e.g., one branch point) is equal to (2$^x$−1)b, where x is equal to the generation number and b is equal to the number of dendrons. For example, in a dendrimer having a core with two dendrons attached (b=2), if each building unit has one branch point and there are 5 generations, there will be 62 building units and the outermost generation will have 16 building units with 64 surface functional groups. In some embodiments, the surface functional groups are amino moieties, for example, primary or secondary amines. In some embodiments, the dendrimer is a fifth-generation dendrimer having a bivalent Core, 62 building units and 64 primary amino functional groups.

In some embodiments, the building units in any of the dendrimers of formula (I), (II), (III), (IV), (V), (VI) or (VII) have the structure:

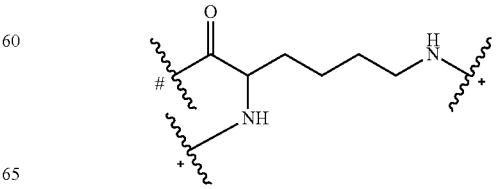

in which # indicates covalent attachment to an amine moiety of Core or an amino moiety of a building unit, and + indicates a covalent attachment to a carbonyl moiety of a building unit, or covalent attachment to a pharmacokinetic modifying group, a linker attached to an active agent or a hydrogen. In some embodiments, the dendrimer has 62 building units with 64 primary amino functional groups.

In some embodiments, the building units in any of the dendrimers of formula (I), (II), (III), (IV), (V), (VI) or (VII) have the structure:

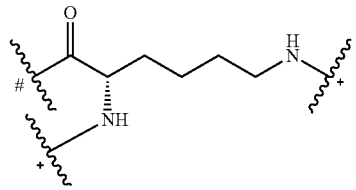 [SMILES: *NCCCC[C@H](N*)C(*)=O]

in which # indicates covalent attachment to an amine moiety of Core or an amino moiety of a building unit, and + indicates a covalent attachment to a carbonyl moiety of a building unit, or covalent attachment to a pharmacokinetic modifying group, a linker attached to an active agent or a hydrogen.

The term "pharmacokinetic modifying group" or "PM" includes moieties that may modify or modulate the pharmacokinetic profile of the dendrimer or the active agent it's delivering. In some embodiments, the PM may modulate the distribution, metabolism and/or excretion of the dendrimer or the active agent. In some embodiments, the PM may influence the release rate of the active agent, either by slowing or increasing the rate by which the active agent is released from the dendrimer by either chemical (e.g., hydrolysis) or enzymatic degradation pathways. In some embodiments, the PM may change the solubility profile of the dendrimer, either increasing or decreasing the solubility in a pharmaceutically acceptable carrier. In some embodiments, the PM may assist the dendrimer in delivering the active agent to specific tissues (e.g., tumors).

In some embodiments, in any of the dendrimers of formula (I), (II), (III), (IV) and (V), the PM is polyethylene glycol (PEG). In some embodiments the PEG has a molecular weight between about 1800 and about 2400 Da. In some embodiments, the PEG has an average molecular weight of about 2150. One of skill in the art would readily understand that the term "PEG$_{1800-2400}$" includes PEG with an average molecular weight of between about 1800 and about 2400 Da.

In some embodiments, the PEG has a polydispersity index (PDI) of between about 1.00 and about 2.00, between about 1.00 and 1.50, for example between about 1.00 and about 1.25, between about 1.00 and about 1.10 or between about 1.00 and about 1.10. In some embodiments, the PDI of the PEG is about 1.05. The term "polydispersity index" refers to a measure of the distribution of molecular mass in a given polymer sample. The PDI is equal to is the weight average molecular weight ($M_w$) divided by the number average molecular weight ($M_n$) and indicates the distribution of individual molecular masses in a batch of polymers. The PDI has a value equal to or greater than 1, but as the polymer approaches uniform chain length and average molecular weight, the PD1 will be closer to 1.

In some embodiments, the dendrimer has less than $(2^x)$b PEG groups, wherein x is the number of generations of the dendrimer and b is the number of dendrons. In some embodiments, all of the surface functional groups are covalently attached to PEG groups. In some embodiments, when x is 5, the dendrimer has between about 25 and about 60 PEG groups. In some embodiments, the dendrimer has no more than $2^x$ PEG groups. In some embodiments, the dendrimer has $2^x$ PEG groups. For example, when the building unit of the dendrimer has one bivalent branch point, a second-generation dendrimer would have no more than 4 PEG groups, a third-generation dendrimer would have no more than 8 PEG groups, a fourth generation dendrimer would have no more than 16 PEG groups, a fifth generation dendrimer would have no more than 32 PEG groups. In some embodiments, dendrimer has less than $2^x$ PEG groups. In some embodiments, the dendrimer has between about 25 and about 64 PEG groups. In some embodiments, the dendrimer has between about 25 and about 40 PEG groups. In some embodiments, the dendrimer has no more than 32 PEG groups. In some embodiments, the dendrimer has between about 25 and about 32 PEG groups. In some embodiments, the dendrimer has about 28 and about 32 PEG groups. In some embodiments, the dendrimer has 29 PEG groups, 30 PEG groups 31 PEG groups or 32 PEG groups.

The disclosed dendrimers of formula (I), (II), (III), (IV), (V), (VI) and (VII) include a linker covalently attached to an active agent (L-AA), in which the linker (L) is covalently attached to the surface functional groups on the final generation of the building units on one end of the linker and to an active agent (AA) on the other end of the linker. In some embodiments, the linker in any of the dendrimers of formula (I), (II), (III), (IV), (V), (VI) or (VII) has the structure:

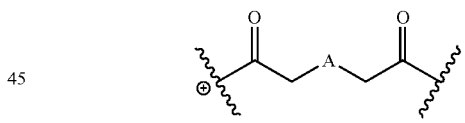

in which ⊕ is covalently attached to the amino functional groups on the final generation of the building units,

is a covalent attachment point to the active agent (AA), and A is —N(CH$_3$) or —S— In some embodiments, A is —S—. In some embodiments, A is —N(CH$_3$).

In some embodiments, AA is a Bcl inhibitor. In some embodiments, AA is a Bcl-2 and/or Bcl-XL inhibitor. In some embodiments, AA is a Bcl-2 and/or Bcl-XL inhibitor disclosed in U.S. Pat. No. 9,018,381. In some embodiments, AA in any of the dendrimers of formula (I), (II), (III), (IV), (V), (VI) or (VII) has the structure:

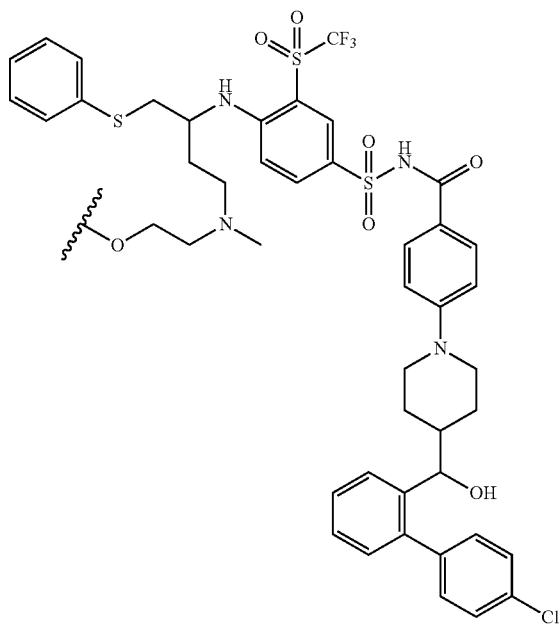 [SMILES: *OCCN(C)CCC(CSc1ccccc1)Nc1ccc(S(=O)(=O)NC(=O)c2ccc(N3CCC(C(O)c4ccccc4-c4ccc(Cl)cc4)CC3)cc2)cc1S(=O)(=O)C(F)(F)F]

in which

is a covalent attachment point to the linker. In some embodiments, AA in any the dendrimers of formula (I), (II), (III), (IV), (V), (VI) or (VII) has the structure:

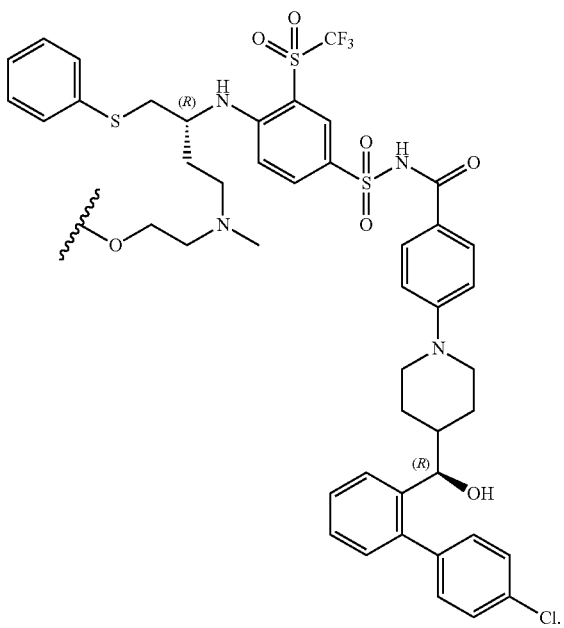

In some embodiments, the structure of L-AA in any of the dendrimers of (I), (II), (III), (IV), (V), (VI) or (VII) is:

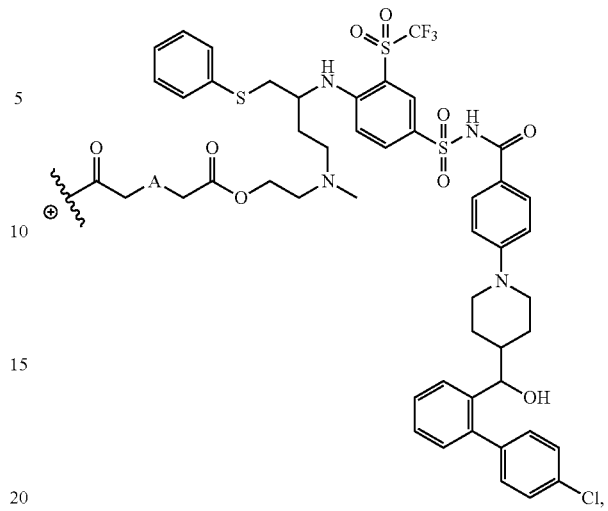

in which ⊕ is covalently attached to the amino functional groups on the final generation of the building units, and A is —N(CH₃) or —S—. In some embodiments, A is —S—. In some embodiments, A is —N(CH₃).

In some embodiments, the structure of L-AA in any of the dendrimers of formula (I), (II), (III), (IV), (V), (VI) or (VII) is:

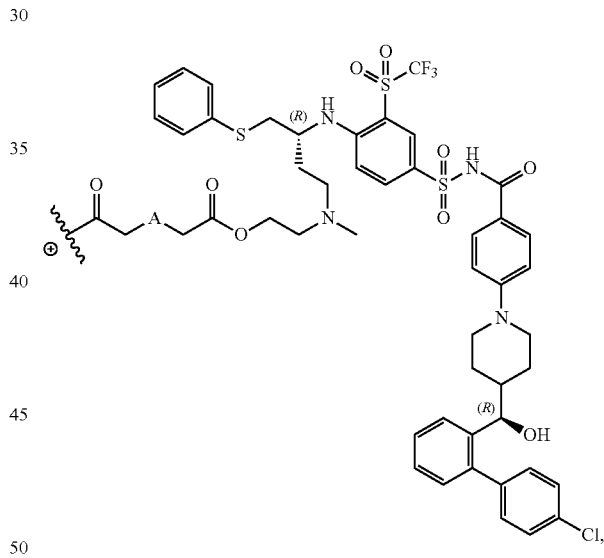

in which ⊕ is covalently attached to the amino functional groups on the final generation of the building units, and A is —N(CH₃) or —S—. In some embodiments, A is —S—. In some embodiments, A is —N(CH₃).

In some embodiments, the dendrimer of any one of formula (I), (II), (III), (IV), (V), (VI) and (VII) has less than $(2^x)b$ L-AA groups, wherein x is the number of generations of the dendrimer and b is the number of dendrons. In some embodiments, all of the surface functional groups are covalently attached to L-AA groups. In some embodiments, when x is 5, the dendrimer has between about 25 and about 64 L-AA groups. In some embodiments, the dendrimer has no more than $2^x$ L-AA groups. In some embodiments, the dendrimer has $2^x$ L-AA groups. For example, when the building unit of the dendrimer has one bifunctional branch point, a second generation dendrimer would have no more than 4 L-AA groups, a third generation dendrimer would have no more than 8 L-AA groups, a fourth generation dendrimer would have no more than 16 L-AA groups, a fifth generation dendrimer would have no more than 32 L-AA groups. In some embodiments, dendrimer has less than $2^x$ L-AA groups. In some embodiments, the dendrimer has between about 25 and about 64 L-AA groups. In some embodiments, the dendrimer has between about 25 and about 40 L-AA groups. In some embodiments, the dendrimer has no more than 32 L-AA groups. In some embodiments, the dendrimer has between about 25 and about 32 L-AA groups. In some embodiments, the dendrimer has between about 28 and about 32 L-AA groups. In some embodiments, the dendrimer has 29 L-AA groups, 30 L-AA groups, 31 L-AA groups or 32 L-AA groups.

In some embodiments, in any of the dendrimers of formula (I), (II), (III), (IV), (V), (VI) and (VII) the sum of L-AA groups and PEG groups may equal no more than 64. In some embodiments, the sum of L-AA groups and PEG groups may be less than 64, provided that the dendrimer has at least one L-AA group. In some embodiments, the sum of L-AA groups and PEG groups may be between about 50 and about 64. In the event that the sum of the L-AA groups and PEG groups is less than 64, the unreacted surface functional units of the final generation of building units remain primary amino groups, provided that the dendrimer has at least one L-AA group. For example, the number of primary amino groups on the final generation of building units is equal to 64 less the sum of the L-AA and PEG groups (e.g., 64-(L-AA+PEG), provided that the dendrimer has at least one L-AA group. For example, if the sum of the L-AA groups and PEG groups is 50, then 14 surface functional groups will remain primary amino moieties, if the sum of the L-AA groups and PEG groups is 51, 13 of the surface functional groups will remain primary amino moieties, if the sum of the L-AA groups and PEG groups is 52, then 12 of the surface functional groups will remain primary amino moieties, if the sum of the L-AA groups and PEG groups is 53, then 11 of the surface functional groups will remain primary amino moieties, etc. In some embodiments, the number of primary amino moieties on the dendrimer is between about 0 and about 14. In some embodiments, if the sum of the number of PEG groups and the number of L-AA groups is less that $(2^x)b$, in which x is the number of generations of the dendrimer and b is the number of dendrons, then the remaining surface functional groups are equal to 64 less the sum of the PEG groups and the L-AA groups, provided that the dendrimer has at least one L-AA group.

In some embodiments, is W is $(PM)_c$ or $(H)_e$; Z is $(L-AA)_d$ or $(H)_e$; provided that (c+d) s $(2^x)b$ and provided that d is >1; wherein x is the number of generations and b is the number of dendrons; and provided that if (c+d)<$(2^x)b$, then any remaining W and Z groups are $(H)_e$, wherein e is $[2^{(x+1)}]-(c+d)$. For example, when b is 2 and x is 5, then (c+d)≤64. In some embodiments, (c+d)=64; that is, the sum of $(PM)_c$ and $(L-AA)_d$ is equal to 64. In some embodiments, when b is 2 and x is 5, then (c+d)<64; that is the sum of $(PM)_c$ and $(L-AA)_d$ is less than 64, provided that d is 1. In some embodiments, (c+d) is an integer between 50 and 64. In some embodiments, (c+d) is an integer between 58 and 64.

In some embodiments, (c+d)=$(2^x)b$ in which case there are no $(H)_e$ and e is 0. For example, if b is 2 and x is 5, and the sum of $(PM)_c$ and $(L-AA)_d$ is equal to 64, then there are no unsubstituted surface functional groups on the fifth generation of building units in the dendrimer, and therefore e is 0. However, (c+d)<$(2^x)b$, then $(H)_e$ is equal to $(2^x)b-(c+d)$. For example, if b is 2, x is 5 and the sum of $(PM)_c$ and $(L-AA)_d$ is less than 64, then the number of unsubstituted surface functional groups on the fifth generation of building blocks is equal to 64 less than the sum of $(PM)_c$ and $(L-AA)_d$. In this case, e is equal to 64 less the sum of $(PM)_c$ and $(L-AA)_d$.

In some embodiments, when the sum of (c+d) is an integer between 50 and 64, e is an integer between 0 and 14. In some embodiments, when (c+d) is an integer between 58 and 64, e is an integer between 0 and 6. In some embodiments, (c+d) is 58 and e is 6. In some embodiments, (c+d) is 59 and e is 5. In some embodiments, (c+d) is 60 and e is 4. In some embodiments, (c+d) is 61 and e is 3. In some embodiments, (c+d) is 62 and e is 2. In some embodiments, (c+d) is 63 and e is 1. In some embodiments, (c+d) is 60 and e is 0.

In some embodiments, any of the dendrimers of formula (I), (II), (III), (IV), (V), (VI) and (VII) have a molecular weight of about 90 to about 120 KDa. In some embodiments, the dendrimer has a molecular weight of about 100 and 115 kDa. In some embodiments, the dendrimer has a molecular weight of about 100 to about 110 kDa. In some embodiments, the dendrimer has a molecular weight of about 100 to about 105 kDa. In some embodiments, the molecular weight of the dendrimer is about 100 kDa, about 101 kDa, about 102 kDa, about 103 KDa, about 104 kDa, about 105 kDa, about 106 KDa, about 107 kDa, about 108 kDa, about 109 kDa or about 110 kDa.

In some embodiments when BU is

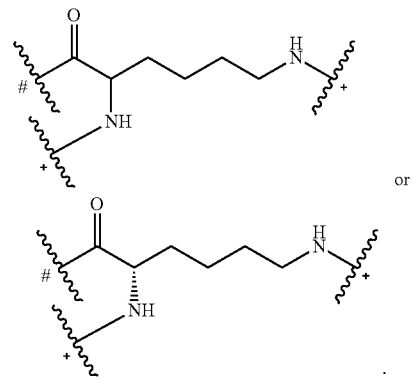

or

PEG is covalently attached to the amino functionality at the ε-position of the BU and the L-AA is covalently attached to amino functionality at the α-position of the BU.

In some embodiments, disclosed are pharmaceutical compositions comprising a lyophilized dendrimer of formula (II):

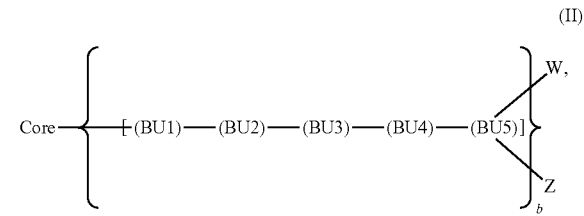

or a pharmaceutically acceptable salt thereof, wherein b is 2;

Core is

[structure: diphenylmethyl-NH-C(=O)-CH(NH-*)-(CH2)4-NH-* (lysine-like core)]

* indicates covalent attachment to a carbonyl moiety of (BU1);
BU are building units and the number of BU is equal to 62; wherein BU has the following structure:

[BU structure: lysine-based with # and + attachment points]

# indicates covalent attachment to an amine moiety of Core or an amino moiety of BU, and + indicates a covalent attachment to a carbonyl moiety of BU or a covalent attachment to W or Z;
W is independently $(PM)_c$ or $(H)_e$;
Z is independently $(L\text{-}AA)_d$ or $(H)_e$;
PM is $PEG_{1800-2400}$;
L-AA is a linker covalently attached to an active agent; wherein L-AA is of the formula:

[L-AA structure with A, phenylthio, triflyl, sulfonamide, piperidine, biphenyl-Cl groups]

wherein
A is —N(CH$_3$) or —S—;
⊕ indicates covalent attachment to an amine moiety of BU5;
provided that (c+d) is ≤64 and d is ≤1; and
provided that if (c+d)<64, then any remaining W and Z groups are $(H)_e$, wherein e is 64−(c+d).

In some embodiments of the dendrimer of formula (II), A is —N(CH$_3$). In some embodiments of the dendrimer of formula (II), A is —S—.

In some embodiments of the dendrimer of formula (II), c is an integer between 25 and 32. In some embodiments of the dendrimer of formula (II), c is an integer between 29 and 32.

In some embodiments of the dendrimer of formula (II), c is 29. In some embodiments of the dendrimer of formula (II), c is 30. In some embodiments of the dendrimer of formula (II), c is 31.

In some embodiments of the dendrimer of formula (II), c is 32.

In some embodiments of the dendrimer of formula (II), d is an integer between 25 and 32. In some embodiments of the dendrimer of formula (II), d is an integer between 29 and 32.

In some embodiments of the dendrimer of formula (II), d is 29. In some embodiments of the dendrimer of formula (II), d is 30. In some embodiments of the dendrimer of formula (II), d is 31.

In some embodiments of the dendrimer of formula (II), d is 32.

In some embodiments of the dendrimer of formula (II), e is an integer between 0 and 14.

In some embodiments of the dendrimer of formula (II), e is an integer between 0 and 6. In some embodiments of the dendrimer of formula (II), e is 0. In some embodiments of the dendrimer of formula (II), e is 1. In some embodiments of the dendrimer of formula (II), e is 2. In some embodiments of the dendrimer of formula (II), e is 3. In some embodiments of the dendrimer of formula (II), e is 4. In some embodiments of the dendrimer of formula (II), e is 5. In some embodiments of the dendrimer of formula (II), e is 6.

In some embodiments of the dendrimer of formula (II), L-AA is:

[L-AA structure with (R) stereocenters]

In some embodiments, disclosed are pharmaceutical compositions comprising a lyophilized dendrimer of formula (III):

D-Core-D     (III)

or a pharmaceutically acceptable salt thereof, wherein

Core is

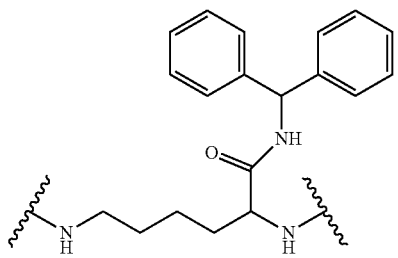 [SMILES: *NCCCCC(N*)C(=O)NC(c1ccccc1)c1ccccc1]

D is

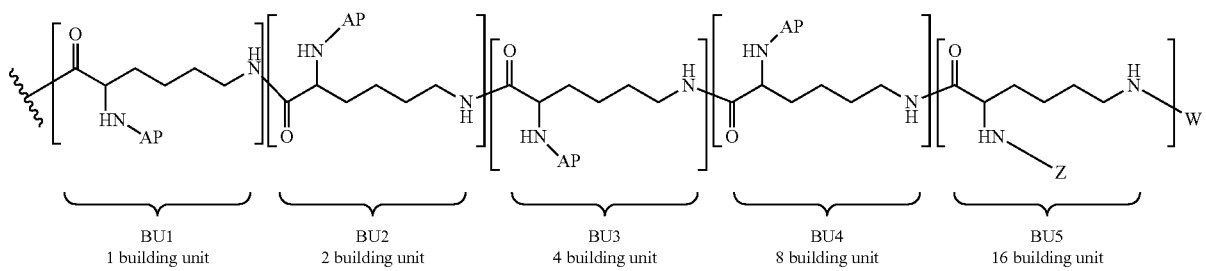

AP is an attachment point to another building unit;
W is independently $(PM)_c$ or $(H)_e$;
Z is independently $(L-AA)_d$ or $(H)_e$;
PM is $PEG_{1800-2400}$;
L-AA is a linker covalently attached to an active agent;
wherein L-AA is of the formula:

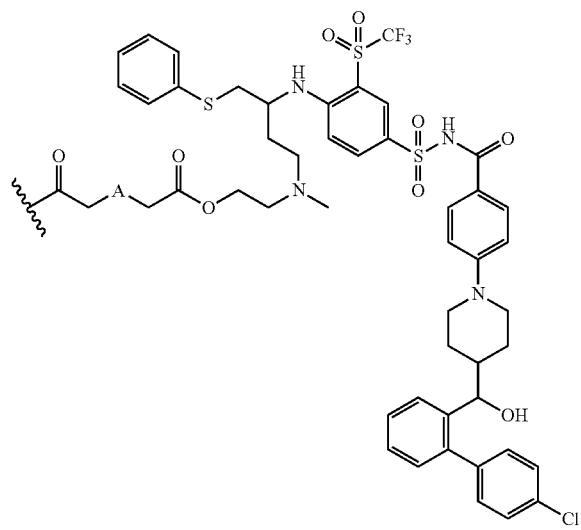

wherein
A is —N(CH$_3$), —O—, —S— or —CH$_2$—;
provided that if (c+d)<64, then any remaining W and Z groups are $(H)_e$, wherein e is 64-(c+d); and d is >1.

In some embodiments of the dendrimer of formula (III), $(PM)_c$ A is —N(CH$_3$). In some embodiments of the dendrimer of formula (III), A is —S—.

In some embodiments of the dendrimer of formula (III), c is an integer between 25 and 32. In some embodiments of the dendrimer of formula (III), c is an integer between 29 and 32.

In some embodiments of the dendrimer of formula (III), c is 29. In some embodiments of the dendrimer of formula (III), c is 30. In some embodiments of the dendrimer of formula (III), c is 31. In some embodiments of the dendrimer of formula (III), c is 32.

In some embodiments of the dendrimer of formula (III), d is an integer between 25 and 32. In some embodiments of the dendrimer of formula (III), d is an integer between 29 and 32.

In some embodiments of the dendrimer of formula (III), d is 29. In some embodiments of the dendrimer of formula (III), d is 30. In some embodiments of the dendrimer of formula (III), d is 31. In some embodiments of the dendrimer of formula (III), d is 32.

In some embodiments of the dendrimer of formula (III), e is an integer between 0 and 14.

In some embodiments of the dendrimer of formula (III), e is an integer between 0 and 6. In some embodiments of the dendrimer of formula (III), e is 0. In some embodiments of the dendrimer of formula (III), e is 1. In some embodiments of the dendrimer of formula (III), e is 2.

In some embodiments of the dendrimer of formula (III), e is 3. In some embodiments of the dendrimer of formula (III), e is 4. In some embodiments of the dendrimer of formula (III), e is 5.

In some embodiments of the dendrimer of formula (III), e is 6.

In some embodiments of the dendrimer of formula (III), L-AA of the dendrimer of formula (III) is:

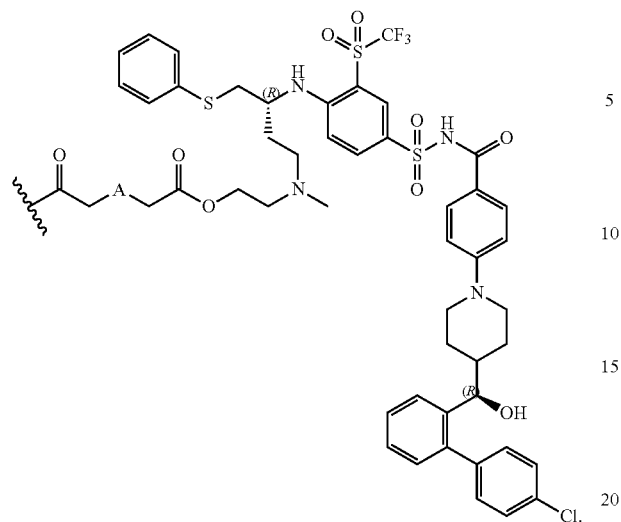
In some embodiments, disclosed are pharmaceutical compositions comprising a lyophilized dendrimer of formula (IV):
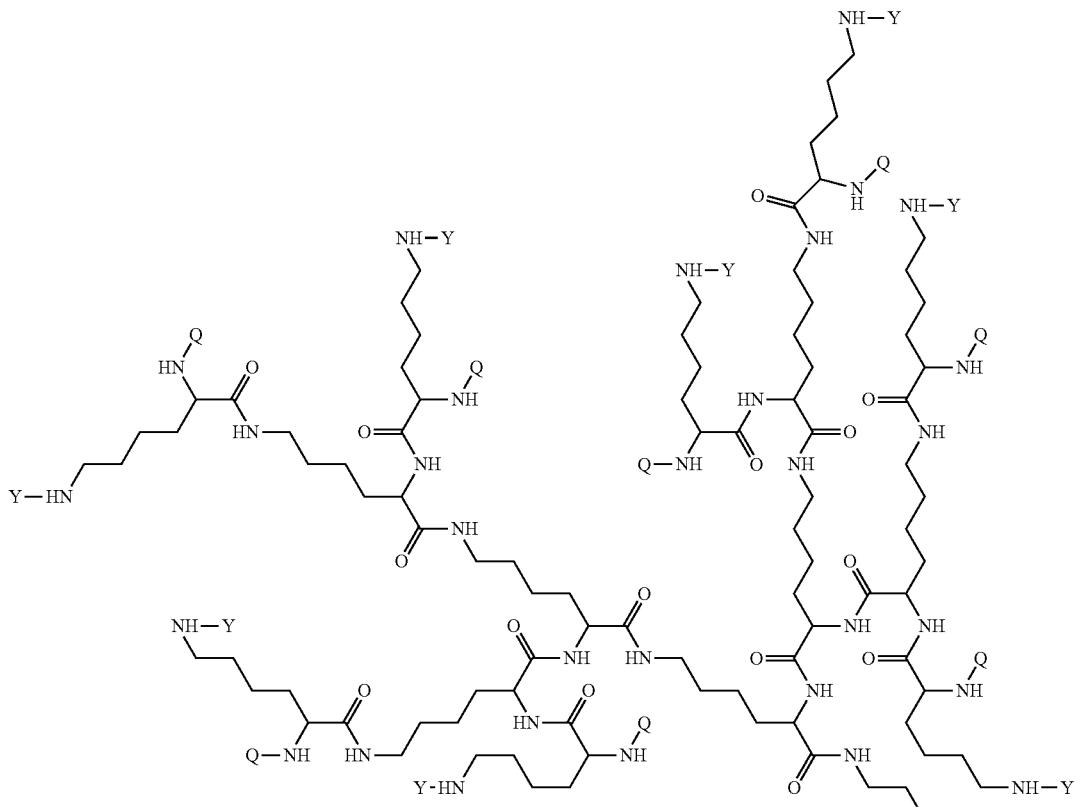

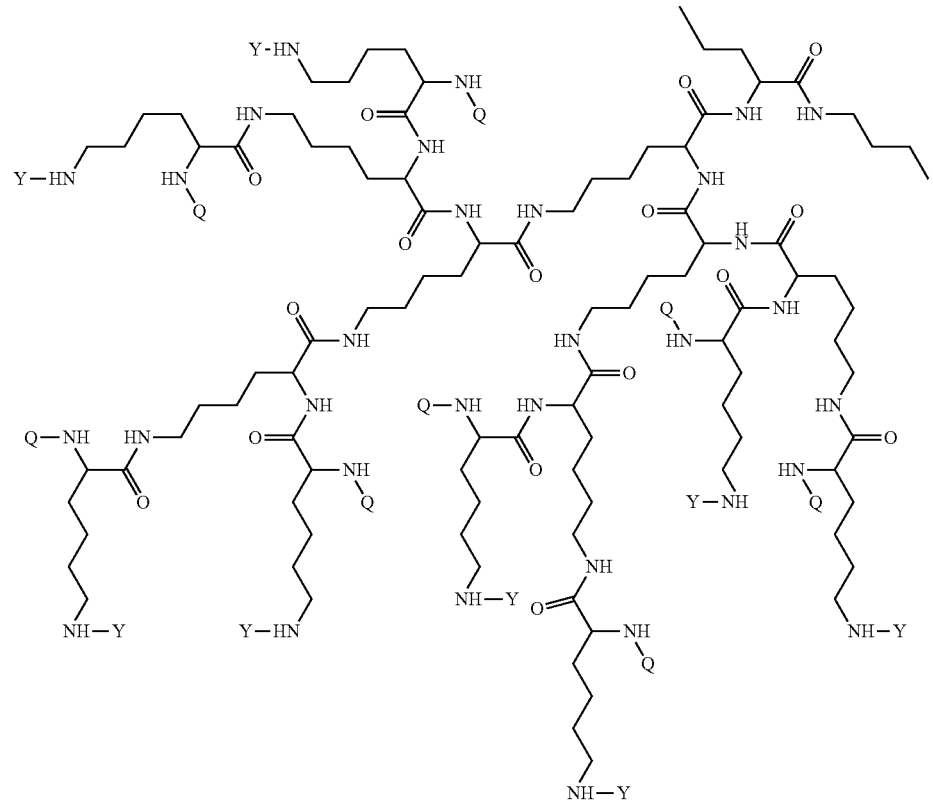

-continued
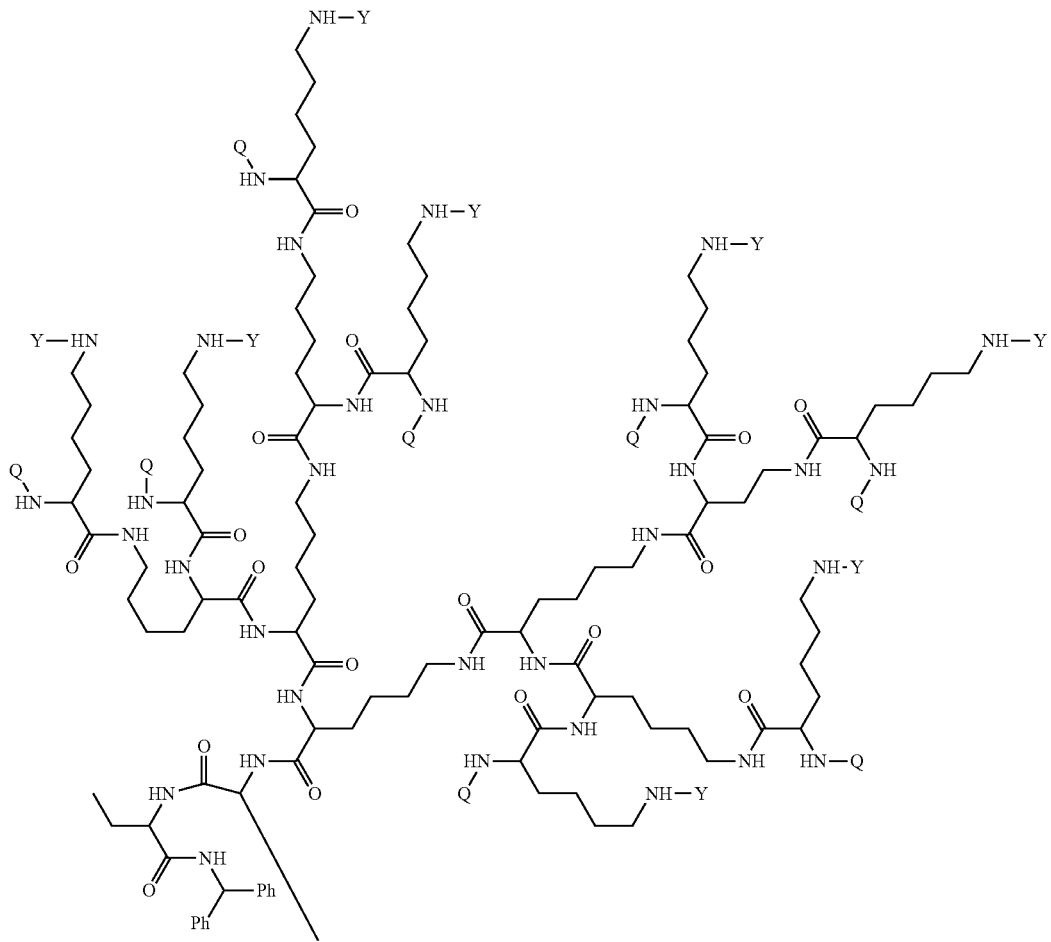

-continued

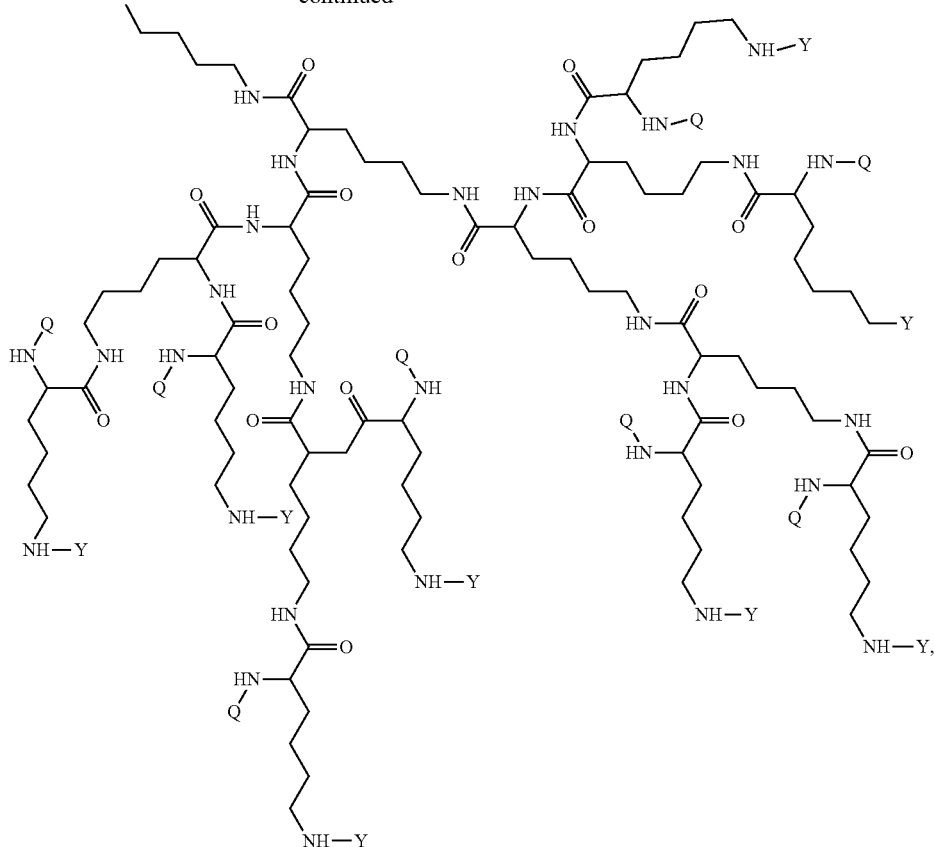

or a pharmaceutically acceptable salt thereof, wherein Y is PEG$_{1800-2400}$ or H; Q is H or L-AA, in which L-AA has the structure:

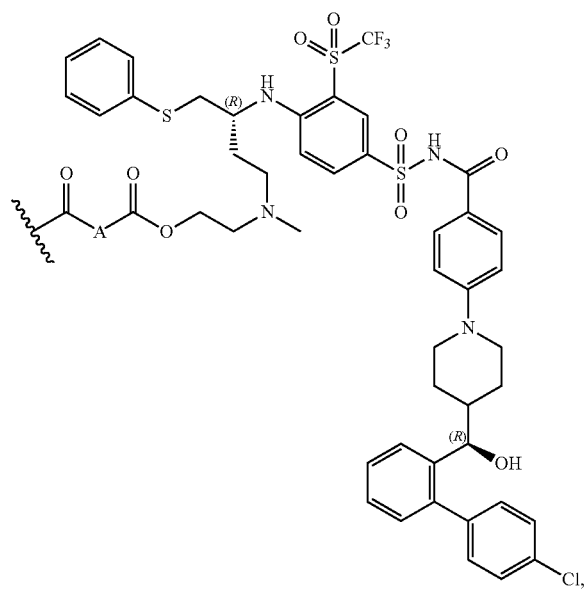

A is —S— or —N(CH$_3$), provided that if the sum of PEG$_{1800-2400}$ and L-AA is less than 64, the remaining Q and Y moieties are H, and provided that at least one Q is L-AA.

In some embodiments of the dendrimer of formula (IV), A is —N(CH$_3$). In some embodiments, of the dendrimer of formula (IV), A is —S—.

In some embodiments, the dendrimer of formula (IV) has between 25 and 32 PEG$_{1800-2400}$. In some embodiments, the dendrimer of formula (IV) has between 29 and 32 PEG$_{1800-2400}$.

In some embodiments, the dendrimer of formula (IV) has 29 PEG$_{1800-2400}$. In some embodiments, the dendrimer of formula (IV) has 30 PEG$_{1800-2400}$. In some embodiments, the dendrimer of formula (IV) has 31 PEG$_{1800-2400}$. In some embodiments, the dendrimer of formula (IV) has 32 PEG$_{1800-2400}$.

In some embodiments, the dendrimer of formula (IV) has between 25 and 32 L-AA. In some embodiments, the dendrimer of formula (IV) has between 29 and 32 L-AA. In some embodiments, the dendrimer of formula (IV) has 29 L-AA. In some embodiments, the dendrimer of formula (IV) has 30 L-AA. In some embodiments, the dendrimer of formula (IV) has 31 L-AA. In some embodiments, the dendrimer of formula (IV) has 32 L-AA.

In some embodiments, the dendrimer of formula (IV) has between 0 and 14 hydrogens at the Q and/or Y positions. In some embodiments, the dendrimer of formula (IV) has between 0 and 6 hydrogens at the Q and/or Y positions. In some embodiments, the dendrimer of formula (IV) has 1 hydrogen at the Q and/or Y positions. In some embodiments, the dendrimer of formula (IV) has 2 hydrogens at the Q and/or Y positions. In some embodiments, the dendrimer of formula (IV) has 3 hydrogens at the Q and/or Y positions. In some embodiments, the dendrimer of formula (IV) has 4 hydrogens at the Q and/or Y positions. In some embodiments, the dendrimer of formula (IV) has 5 hydrogens at the Q and/or Y positions. In some embodiments, the dendrimer of formula (IV) has 6 hydrogens at the Q and/or Y positions.
In some embodiments, disclosed are pharmaceutical compositions comprising a lyophilized dendrimer of formula (V):
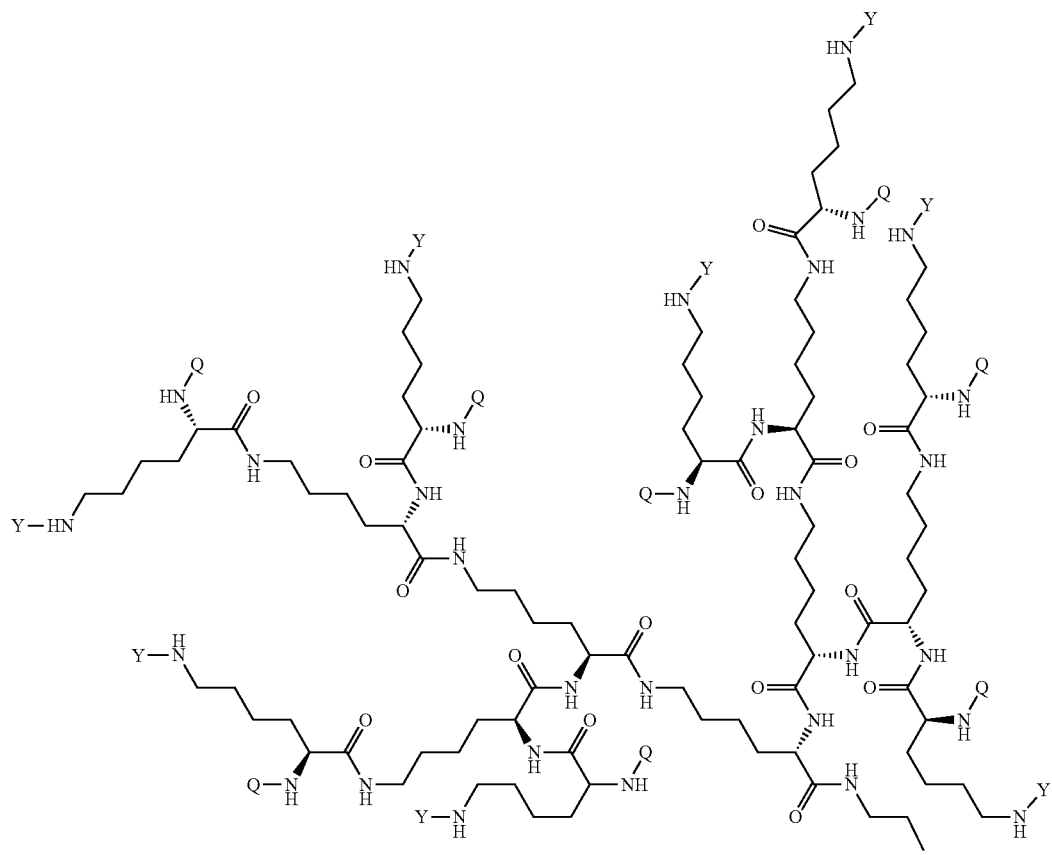
(V)

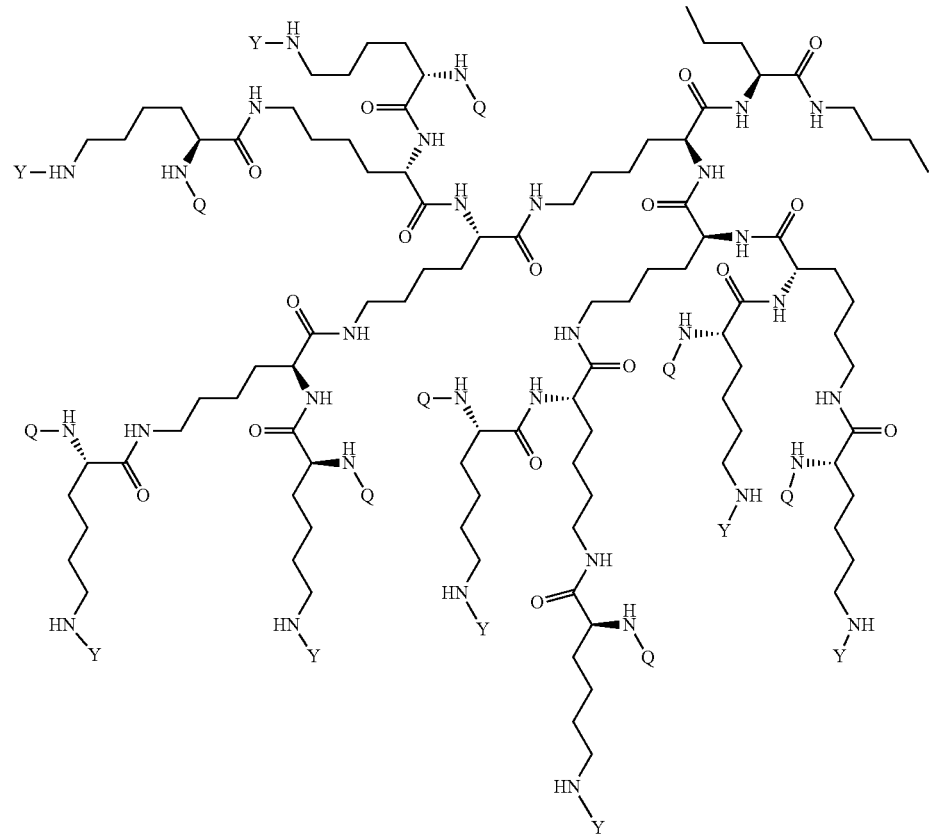

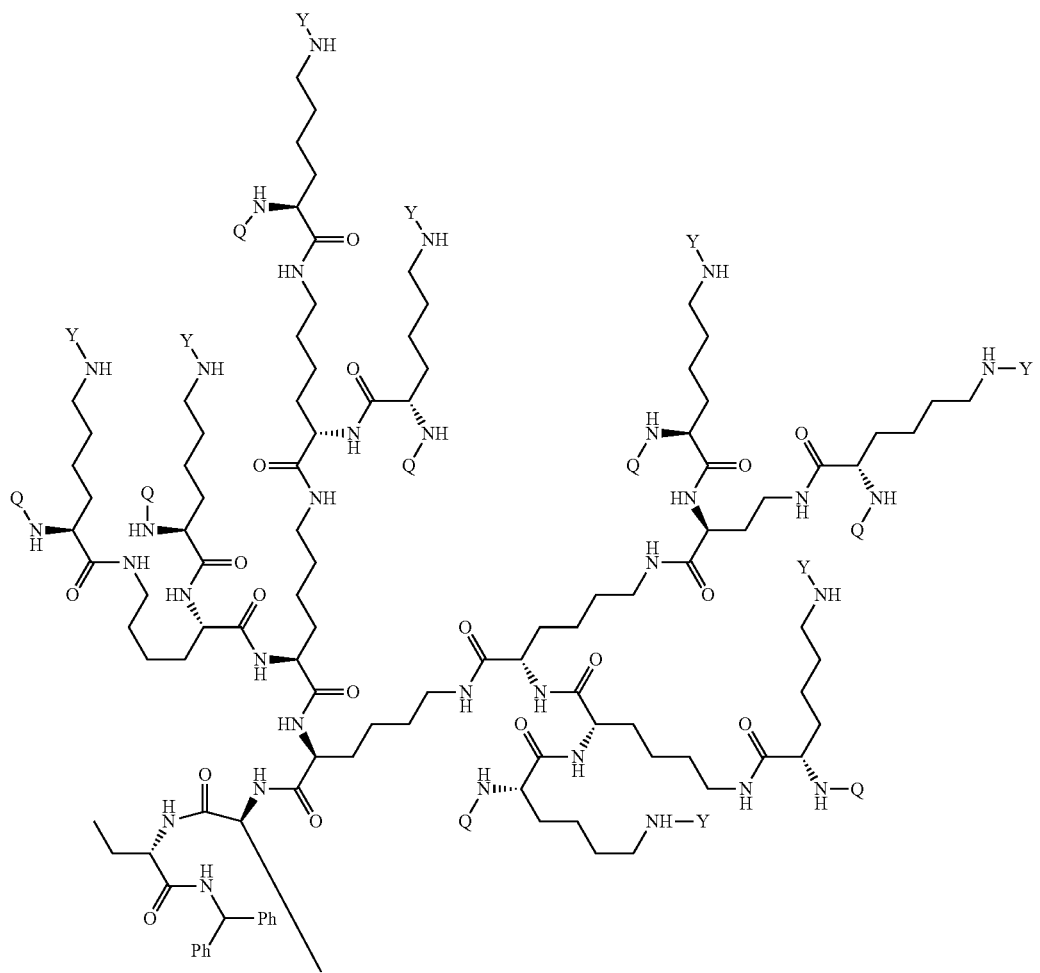

-continued

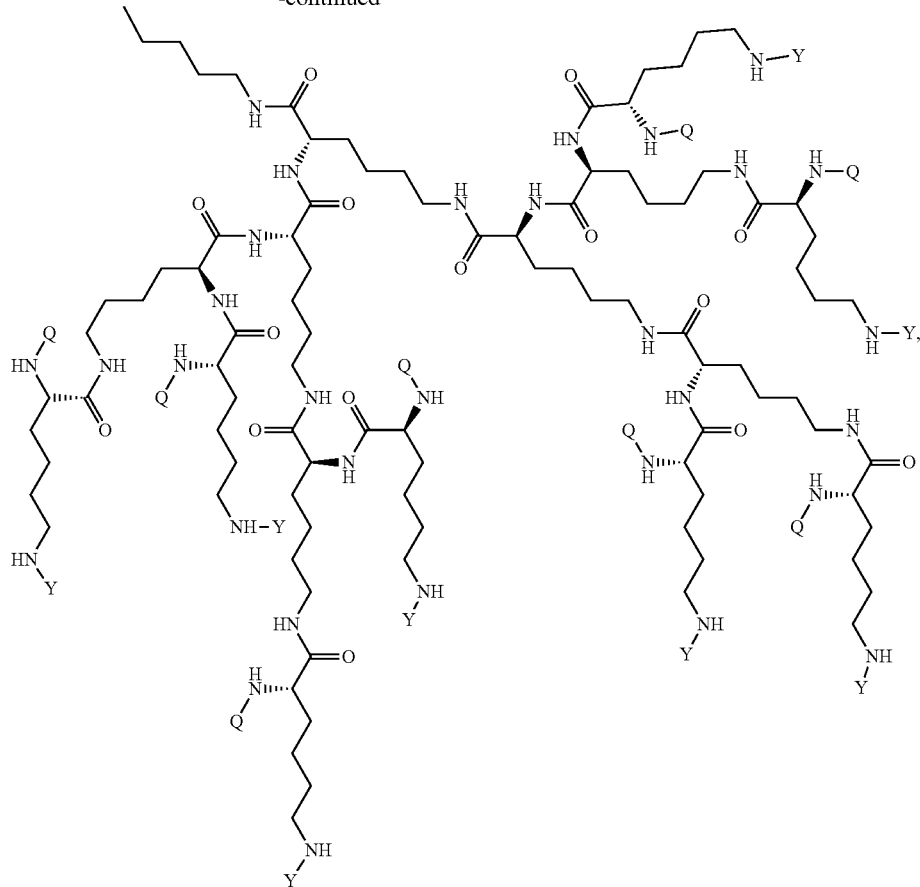

or a pharmaceutically acceptable salt thereof, wherein

Y is $PEG_{1800-2400}$ or H;

Q is H or L-AA, wherein L-AA has the structure:

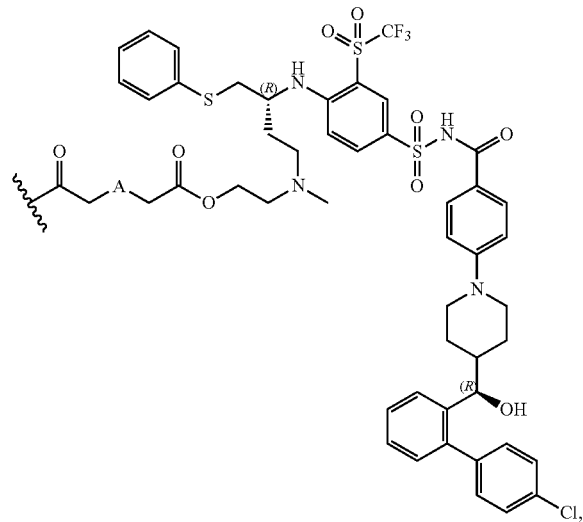

A is —S— or —N($CH_3$), provided that if the sum of $PEG_{1800-2400}$ and L-AA is less than 64, the remaining Q and Y moieties are H, and provided that at least one Q is L-AA.

In some embodiments of the dendrimer of formula (V), A is —N($CH_3$) (Compound 1). In some embodiments, of the dendrimer of formula (V), A is —S— (Compound 2).

In some embodiments, the dendrimer of formula (V) has between 25 and 32 $PEG_{1800-2400}$. In some embodiments, the dendrimer of formula (V) has between 29 and 32 $PEG_{1800-2400}$.

In some embodiments, the dendrimer of formula (V) has 29 $PEG_{1800-2400}$. In some embodiments, the dendrimer of formula (V) has 30 $PEG_{1800-2400}$. In some embodiments, the dendrimer of formula (V) has 31 $PEG_{1800-2400}$. In some embodiments, the dendrimer of formula (V) has 32 $PEG_{1800-2400}$.

In some embodiments, the dendrimer of formula (V) has between 25 and 32 L-AA. In some embodiments, the dendrimer of formula (V) has between 29 and 32 L-AA. In some embodiments, the dendrimer of formula (V) has 29 L-AA. In some embodiments, the dendrimer of formula (V) has 30 L-AA. In some embodiments, the dendrimer of formula (V) has 31 L-AA. In some embodiments, the dendrimer of formula (V) has 32 L-AA.

In some embodiments, the dendrimer of formula (V) has between 0 and 14 hydrogens at the Q and/or Y positions. In some embodiments, the dendrimer of formula (V) has between 0 and 6 hydrogens at the Q and/or Y positions. In some embodiments, the dendrimer of formula (V) has 1 hydrogen at the Q and/or Y positions. In some embodiments, the dendrimer of formula (V) has 2 hydrogens at the Q and/or Y positions. In some embodiments, the dendrimer of formula (V) has 3 hydrogens at the Q and/or Y positions. In some embodiments, the dendrimer of formula (V) has 4 hydrogens at the Q and/or Y positions. In some embodiments, the dendrimer of formula (V) has 5 hydrogens at the Q and/or Y positions. In some embodiments, the dendrimer of formula (V) has 6 hydrogens at the Q and/or Y positions.
In some embodiments, disclosed are pharmaceutical compositions comprising a lyophilized dendrimer of formula (VI):
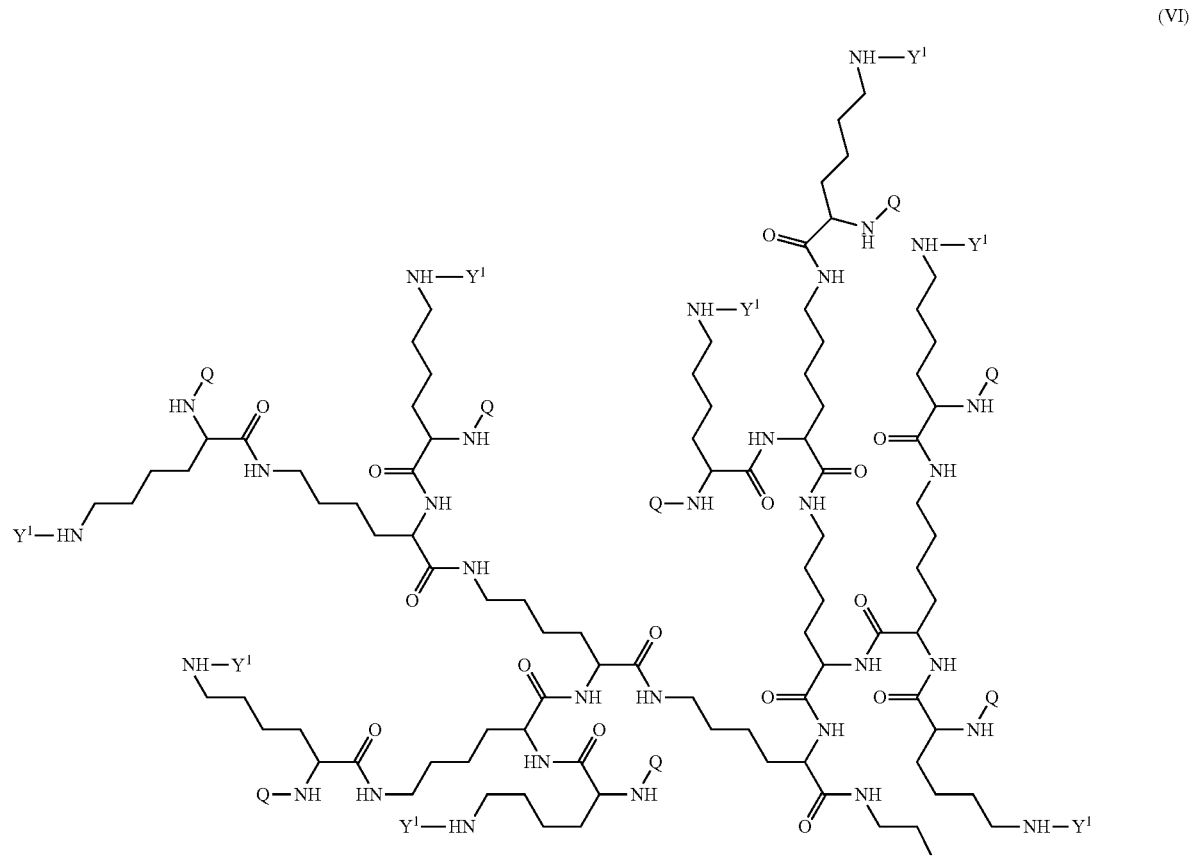

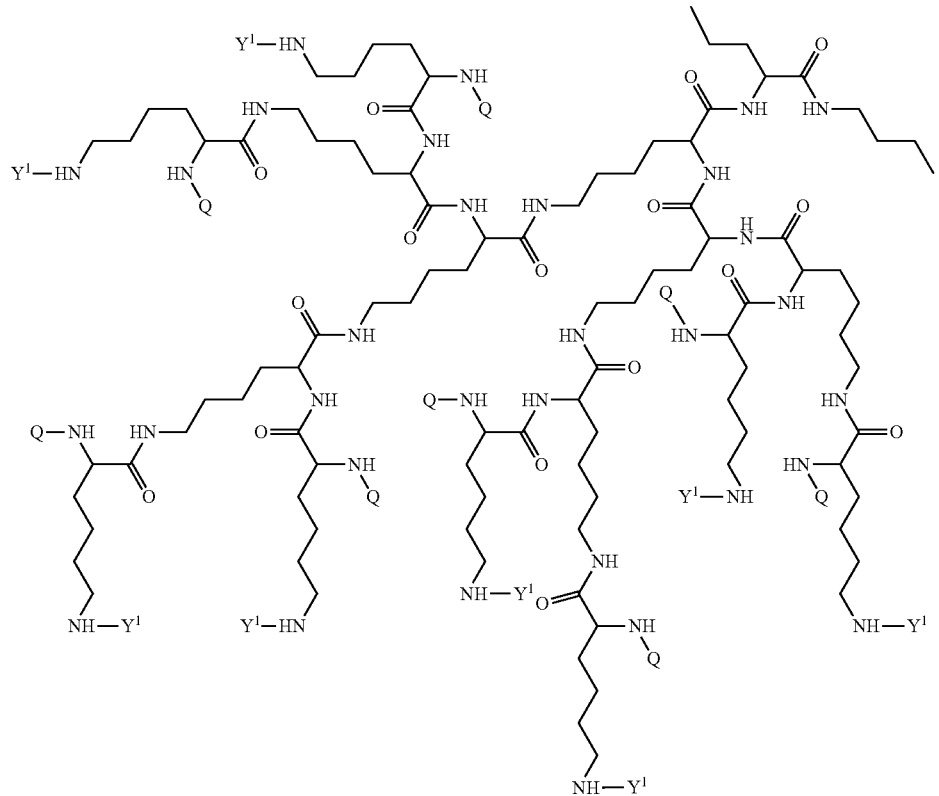

-continued
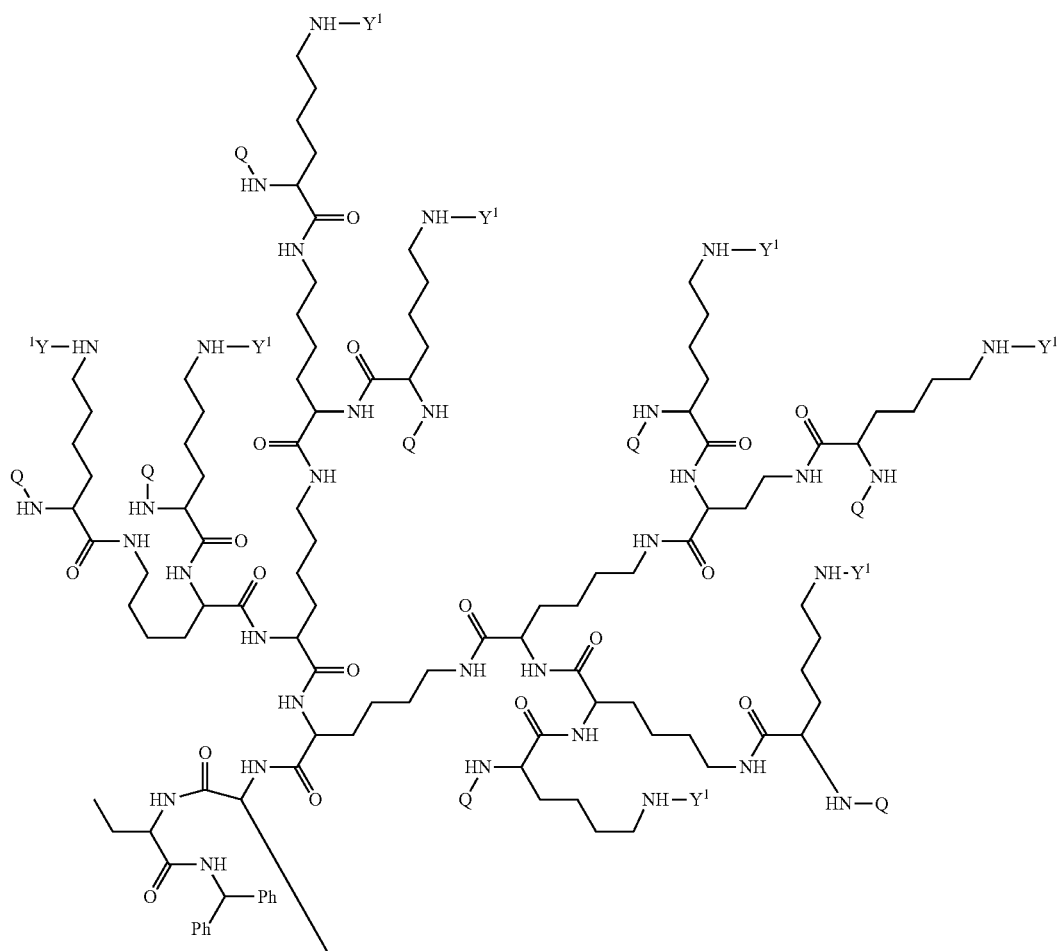

-continued

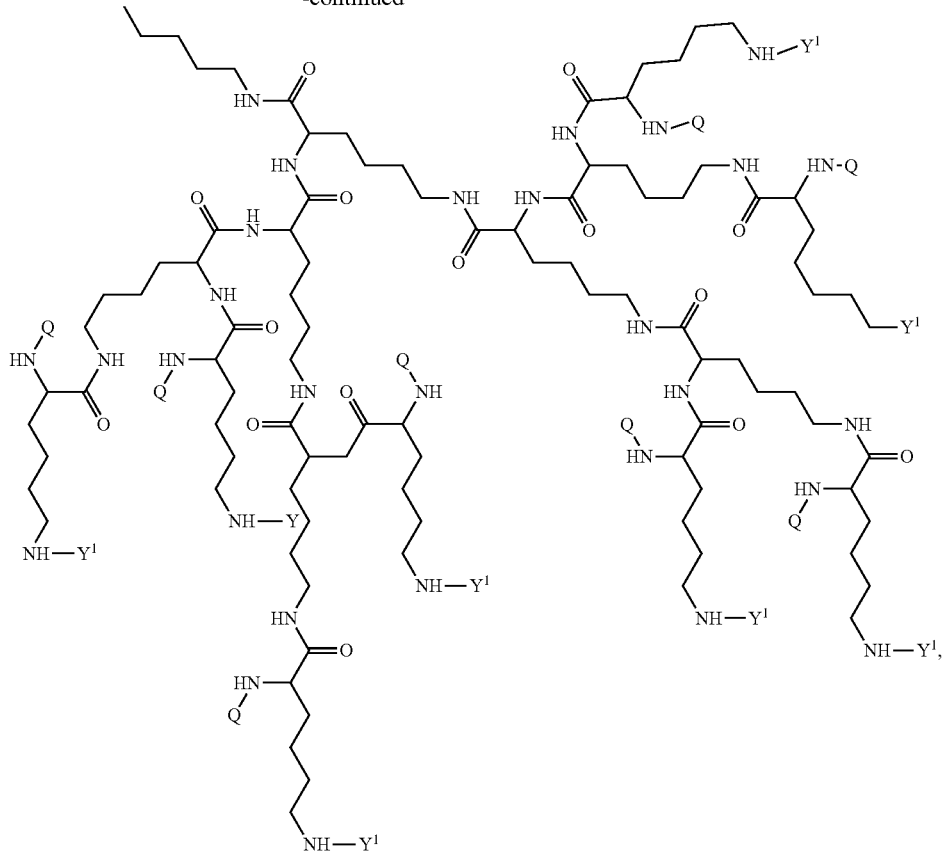

or a pharmaceutically acceptable salt thereof, wherein
Y$^1$ is —C(=O)CH$_2$—(OCH$_2$CH$_2$)$_x$—OCH$_3$ or H;
x is an integer from between 39 and 53; and
Q is H or L-AA, in which L-AA has the structure:

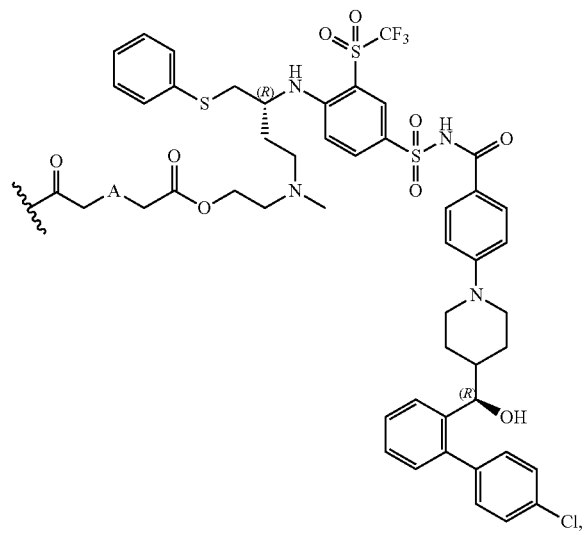

A is —S— or —N(CH$_3$), provided that if the sum of Y$^1$ and L-AA is less than 64, the remaining Q and Y$^1$ moieties are H, and provided that at least one Q is L-AA. In some embodiments, disclosed is the compound of formula (VI) in which A is —S—. In some embodiments, disclosed is the compound of formula (VI) in which A is —N(CH$_3$).

In some embodiments, the dendrimer of formula (VI) has between 25 and 32 Y$^1$ moieties. In some embodiments, the dendrimer of formula (VI) has between 29 and 32 Y$^1$ moieties. In some embodiments, the dendrimer of formula (VI) has 29 Y$^1$ moieties. In some embodiments, the dendrimer of formula (VI) has 30 Y$^1$ moieties. In some embodiments, the dendrimer of formula (VI) has 31 Y$^1$ moieties. In some embodiments, the dendrimer of formula (VI) has 32 Y$^1$ moieties.

In some embodiments, the dendrimer of formula (VI) has between 25 and 32 L-AA moieties. In some embodiments, the dendrimer of formula (VI) has between 29 and 32 L-AA moieties. In some embodiments, the dendrimer of formula (VI) has 29 L-AA moieties. In some embodiments, the dendrimer of formula (VI) has 30 L-AA moieties. In some embodiments, the dendrimer of formula (VI) has 31 L-AA moieties. In some embodiments, the dendrimer of formula (VI) has 32 L-AA moieties.

In some embodiments, the dendrimer of formula (VI) has between 0 and 14 hydrogens at the Q and/or Y$^1$ positions. In some embodiments, the dendrimer of formula (VI) has between 0 and 6 hydrogens at the Q and/or Y$^1$ positions. In some embodiments, the dendrimer of formula (VI) has 1 hydrogen at the Q and/or Y$^1$ positions. In some embodiments, the dendrimer of formula (VI) has 2 hydrogens at the Q and/or Y$^1$ positions. In some embodiments, the dendrimer of formula (VI) has 3 hydrogens at the Q and/or Y$^1$ positions. In some embodiments, the dendrimer of formula (VI) has 4 hydrogens at the Q and/or Y$^1$ positions. In some embodiments, the dendrimer of formula (VI) has 5 hydrogens at the Q and/or $Y^1$ positions. In some embodiments, the dendrimer of formula (VI) has 6 hydrogens at the Q and/or $Y^1$ positions.

In some embodiments, x is an integer between 39 and 53. In some embodiments, x is an integer between 41 and 50. In some embodiments, x is an integer between 44 and 48. In some embodiments, x is and integer selected from 45, 46 or 47. In some embodiments, x is 39.

In some embodiments, x is 40. In some embodiments, x is 41. In some embodiments, x is 42.

In some embodiments, x is 43. In some embodiments, x is 44. In some embodiments, x is 45.

In some embodiments, x is 46. In some embodiments, x is 47. In some embodiments, x is 48.

In some embodiments, x is 49. In some embodiments, x is 50. In some embodiments, x is 51.

In some embodiments, x is 52. In some embodiments, x is 53.

In some embodiments, disclosed are pharmaceutical compositions comprising a lyophilized dendrimer of formula (VII):

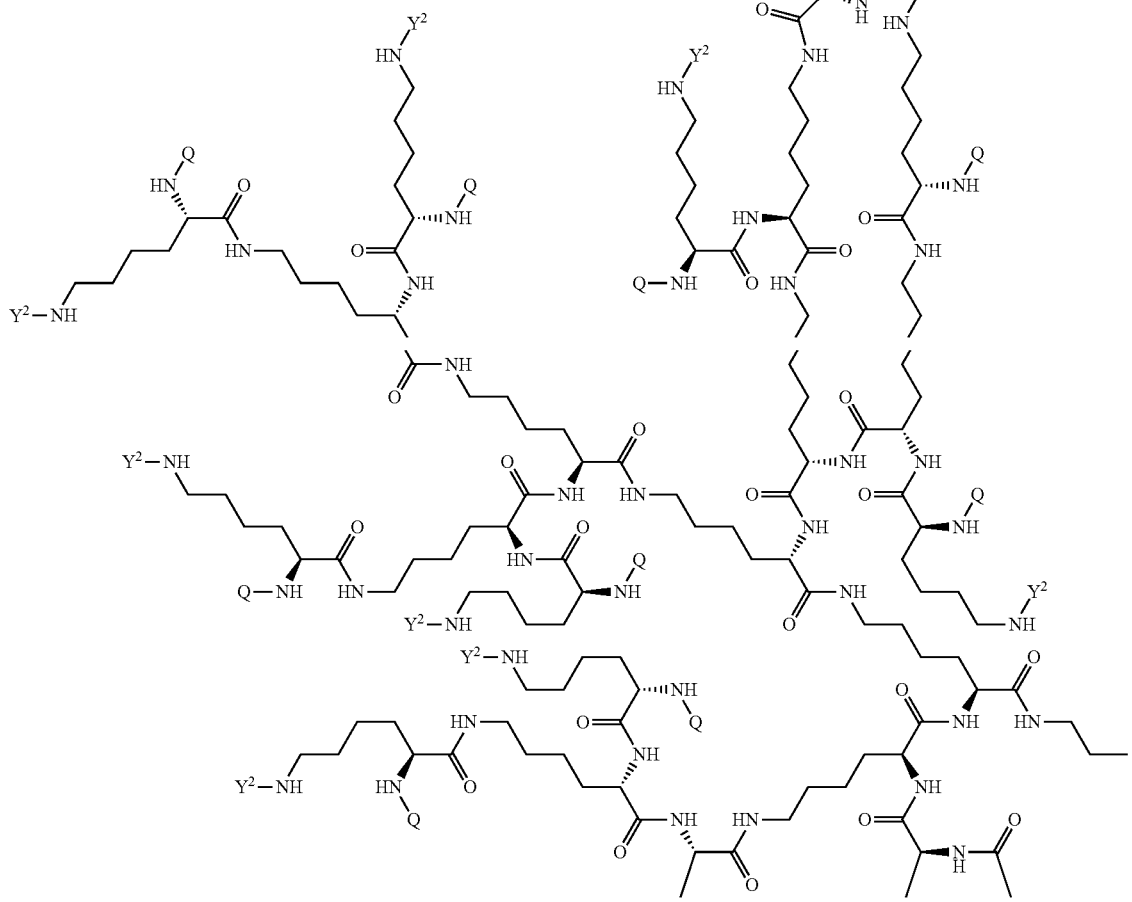

(VII)

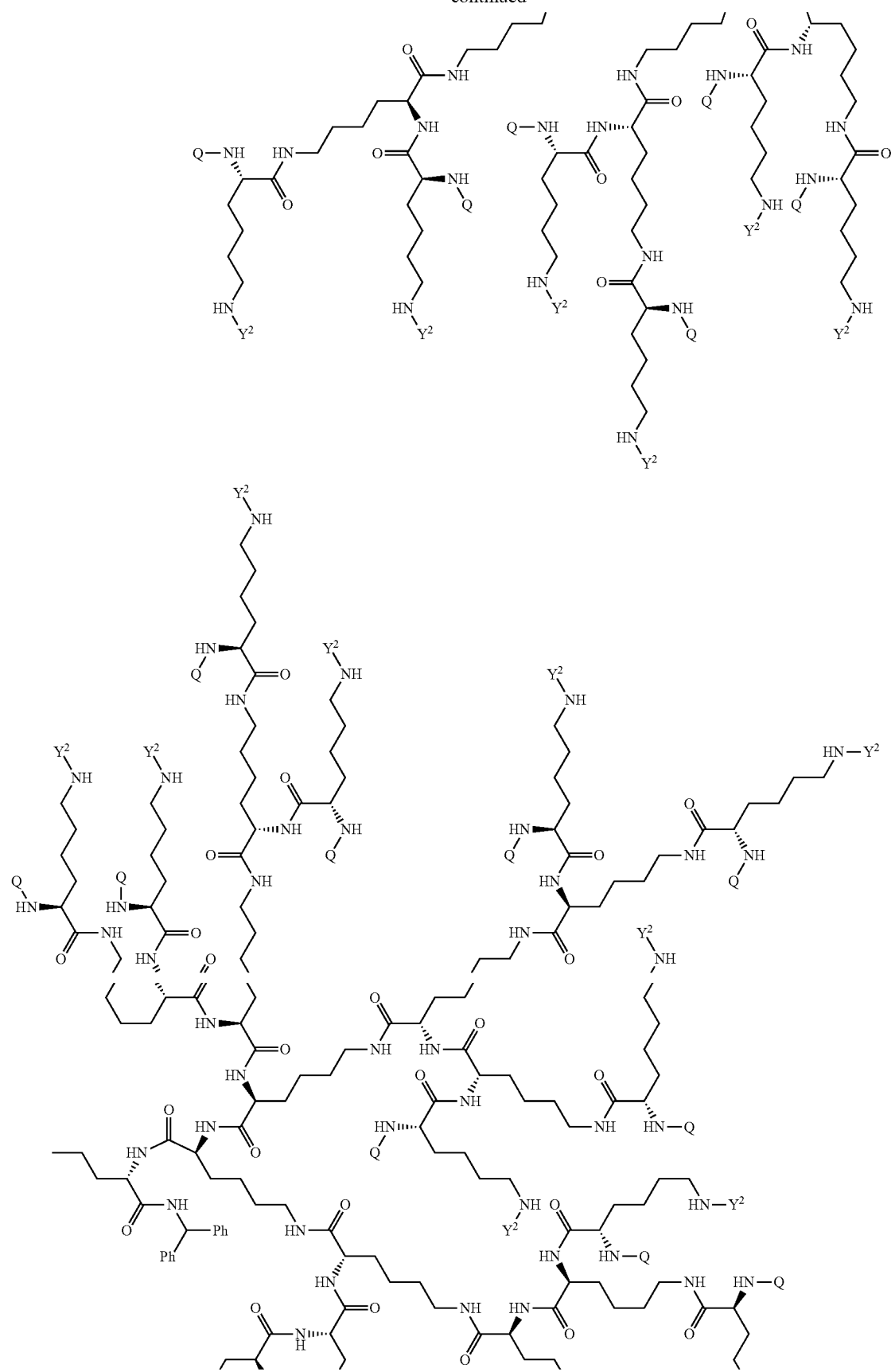

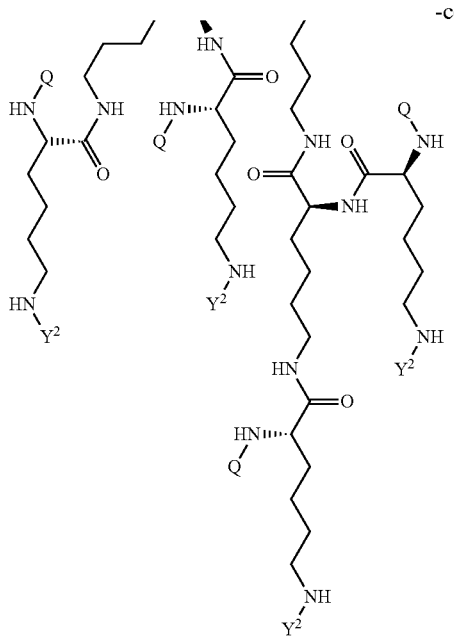
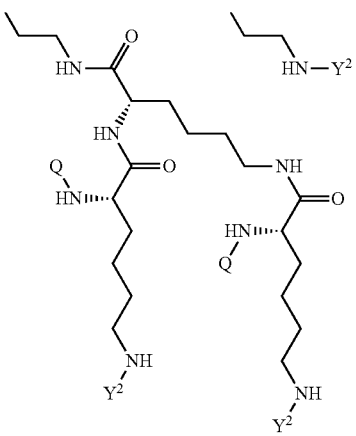

or a pharmaceutically acceptable salt thereof, wherein
Y$^2$ is —C(=O)CH$_2$—(OCH$_2$CH$_2$)$_y$—OCH$_3$ or H;
y is an integer from between 39 and 53; and
Q is H or L-AA, in which L-AA has the structure:

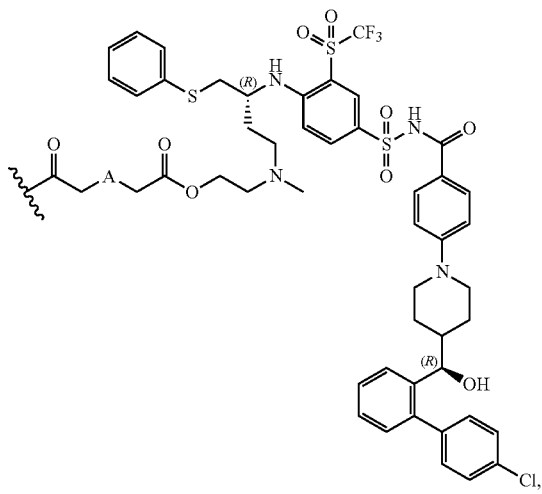

A is —S— or —N(CH$_3$), provided that if the sum of Y$^2$ and L-AA is less than 64, the remaining Q and Y$^2$ moieties are H, and provided that at least one Q is L-AA. In some embodiments, disclosed is the compound of formula (VII) in which A is —S—. In some embodiments, disclosed is the compound of formula (VII) in which A is —N(CH$_3$).

In some embodiments, the dendrimer of formula (VII) has between 25 and 32 Y$^2$ moieties. In some embodiments, the dendrimer of formula (VII) has between 29 and 32 Y$^2$ moieties. In some embodiments, the dendrimer of formula (VII) has 29 Y$^2$ moieties. In some embodiments, the dendrimer of formula (VII) has 30 Y$^2$ moieties. In some embodiments, the dendrimer of formula (VII) has 31 Y$^2$ moieties. In some embodiments, the dendrimer of formula (VII) has 32 Y$^2$ moieties.

In some embodiments, the dendrimer of formula (VII) has between 25 and 32 L-AA moieties. In some embodiments, the dendrimer of formula (VII) has between 29 and 32 L-AA moieties. In some embodiments, the dendrimer of formula (VII) has 29 L-AA moieties. In some embodiments, the dendrimer of formula (VII) has 30 L-AA moieties. In some embodiments, the dendrimer of formula (VII) has 31 L-AA moieties. In some embodiments, the dendrimer of formula (VII) has 32 L-AA moieties.

In some embodiments, the dendrimer of formula (VII) has between 0 and 14 hydrogens at the Q and/or Y$^2$ positions. In some embodiments, the dendrimer of formula (VII) has between 0 and 6 hydrogens at the Q and/or Y$^2$ positions. In some embodiments, the dendrimer of formula (VII) has 1 hydrogen at the Q and/or Y$^2$ positions. In some embodiments, the dendrimer of formula (VII) has 2 hydrogens at the Q and/or Y$^2$ positions. In some embodiments, the dendrimer of formula (VII) has 3 hydrogens at the Q and/or Y$^2$ positions. In some embodiments, the dendrimer of formula (VII) has 4 hydrogens at the Q and/or Y$^2$ positions. In some embodiments, the dendrimer of formula (VII) has 5 hydrogens at the Q and/or Y$^2$ positions. In some embodiments, the dendrimer of formula (VII) has 6 hydrogens at the Q and/or Y$^2$ positions.

In some embodiments, y is an integer between 39 and 53. In some embodiments, y is an integer between 41 and 50. In some embodiments, y is an integer between 44 and 48. In some embodiments, y is an integer selected from 45, 46 or 47. In some embodiments, y is 39. In some embodiments, y is 40. In some embodiments, y is 41. In some embodiments, y is 42. In some embodiments, y is 43. In some embodiments, y is 44. In some embodiments, y is 45. In some embodiments, y is 46. In some embodiments, y is 47. In some embodiments, y is 48. In some embodiments, y is 49. In some embodiments, y is 50. In some embodiments, y is 51. In some embodiments, y is 52. In some embodiments, y is 53.

The language "pharmaceutically acceptable salt" includes acid addition or base salts that retain the biological effectiveness and properties of the dendrimers of formula (I), (II), (III), (IV), (V), (VI) and (VIII), and, which typically are not biologically or otherwise undesirable. In many cases, the dendrimers of formula (I), (II), (III), (IV), (V), (VI) and (VII) are capable of forming acid and/or base salts by virtue of the presence of basic and/or carboxyl groups or groups similar thereto.

The pharmaceutically acceptable salts of the dendrimers of formula (I), (II), (III), (IV), (V), (VI) and (VII) can be synthesized from a basic or acidic moiety, by conventional chemical methods. Generally, such salts can be prepared by reacting free acid forms of these compounds with a stoichiometric amount of the appropriate base or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "*J. Pharm. Sci.,* 1977, 66, 1-19 and in "Handbook of Pharmaceutical Salts: Properties, Selection, and Use" by Stahl and Wermuth (Wiley-VCH, Weinheim, Germany, 2002).

Any formula given herein may also represent unlabeled forms as well as isotopically labeled forms for the dendrimers of formula (I), (II), (III), (IV), (V), (VI) and (VII), or a pharmaceutically acceptable salt thereof. Isotopically labeled compounds have structures depicted by the formulas given herein except that one or more atoms are replaced by an atom of the same element but with differing mass number. Examples of isotopes that can be incorporated into the dendrimer of formula (I), (II), (III), (IV), (V), (VI) and (VIII) and their salts include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{35}S$ and $^{125}I$. The dendrimers of formula (I), (II), (III), (IV), (V), (VI) and (VIII), or a pharmaceutically acceptable salt thereof, may include various isotopically labeled compounds into which radioactive isotopes, such as, $^{3}H$, $^{11}C$, $^{14}C$, $^{35}S$ and $^{36}Cl$ are present. Isotopically labeled dendrimers of formula (I), (II), (III), (IV), (V), (VI) and (VII), or a pharmaceutically acceptable salt thereof, can generally be prepared by conventional techniques known to those skilled in the art or by processes analogous to those described in the accompanying Examples using appropriate isotopically labeled reagents in place of the non-labeled reagents previously employed.

The dendrimers of formula (I), (II), (III), (IV), (V), (VI) and (VII), or a pharmaceutically acceptable salt thereof, may have different isomeric forms. The language "optical isomer" or "stereoisomer" refers to any of the various stereoisomeric configurations which may exist for a given dendrimer of formula (I), (II), (III), (IV), (V), (VI) and (VII), or a pharmaceutically acceptable salt thereof. In particular, the dendrimers of formula (I), (II), (III), (IV), (V), (VI) and (VIII), or a pharmaceutically acceptable salt thereof, possess chirality and as such may exist as mixtures of enantiomers with enantiomeric excess between about 0% and >98% e.e. When a compound is a pure enantiomer, the stereochemistry at each chiral center may be specified by either R or S. Such designations may also be used for mixtures that are enriched in one enantiomer. Resolved compounds whose absolute configuration is unknown can be designated (+) or (−) depending on the direction (dextro- or levorotatory) which they rotate plane polarized light at the wavelength of the sodium D line. The present disclosure is meant to include all such possible isomers, including racemic mixtures, optically pure forms and intermediate mixtures. Optically active (R)- and (S)-isomers may be prepared using chiral synthons, chiral reagents or chiral catalysts, or resolved using conventional techniques well known in the art, such as chiral HPLC.

In some embodiments, disclosed are lyophilized compositions comprising a dendrimer of formula (I), (II), (III), (IV), (V), (VI) or (VII), or a pharmaceutically acceptable salt thereof, prepared by the process comprising the steps of dissolving the compound of formula (I), (II), (III), (IV) (V), (VI), or (VII), or a pharmaceutically acceptable salt thereof, in glacial acetic acid to form a solution, freeze drying the solution and subliming the acetic acid at reduced pressure.

The language "pharmaceutically acceptable compositions" includes compounds, materials, diluent or solvents, excipients, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be obtained by conventional procedures using conventional pharmaceutical excipients well known in the art, for example, suspending agents, dispersing or wetting agents, preservatives, anti-oxidants, emulsifying agents, binders, disintegrants, glidants, lubricants or sorbents.

In some embodiments, the disclosed pharmaceutical compositions are reconstituted in a pharmaceutically acceptable diluent or solvent to form a sterile injectable solution in one or more aqueous or non-aqueous non-toxic parenterally-acceptable buffer systems, diluent or solvents, solubilizing agents, co-solvents, or carriers. A sterile injectable preparation may also be a sterile injectable aqueous or oily suspension or suspension in a non-aqueous diluent or solvent, carrier or co-solvent, which may be formulated according to known procedures using one or more of the appropriate dispersing or wetting agents and suspending agents. In some embodiments, the pharmaceutically acceptable diluent or solvent comprises a citrate buffer solution. In some embodiments, the citrate buffer is at pH 5. In some embodiments, the citrate buffer comprises citric acid monohydrate, sodium citrate dihydrate and dextrose anhydrous. In some embodiments, the diluent or solvent is a 50 mM citrate buffer at pH 5 in 5% (w/w) dextrose. In some embodiments, the diluent or solvent is a pH5 citrate/phosphate buffer diluted 1 in 10 with 5% w/v glucose. In some embodiments, the pharmaceutically acceptable diluent or solvent comprises an acetate buffer solution. In some embodiments, the acetate buffer solution is at pH 5. In some embodiments, the acetate buffer solution comprises acetic acid, sodium acetate anhydrous and dextrose. In some embodiments, the acetate buffer comprises 100 mM acetate buffer (pH 5) in 2.5% (w/w) dextrose.

The pharmaceutical compositions could be reconstituted to form a solution for iv bolus/infusion injection, sterile dendrimer for reconstitution with a buffer system, or a lyophilized system (either dendrimer alone or with excipients) for reconstitution with a buffer system with or without other excipients. The lyophilized freeze-dried material may be prepared from non-aqueous solvents or aqueous solvents. The dosage form could also be a concentrate for further dilution for subsequent infusion.

The amount of active ingredient that may be combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The dendrimers of formula (I), (II), (III), (IV), (V), (VI) and (VII), or a pharmaceutically acceptable salt thereof, may be administered once, twice, three times a day or as many times in a 24-hour period as medically necessary. One of skill in the art would readily be able to determine the amount of each individual dose based on the subject. In some embodiments, the dendrimers of formula (I), (II), (III), (IV), (V), (VI) and (VII) or a pharmaceutically acceptable salt thereof, are administered in one dosage form. In some embodiments, the dendrimers of formula (I), (II), (III), (IV), (V), (VI) and (VII), or a pharmaceutically acceptable salt thereof, are administered in multiple dosage forms.

In some embodiments, the pH of the pharmaceutical composition is between about 4.0 and about 6.0, for example, between about 4.8 to about 5.6.

In some embodiments, the pharmaceutical composition comprises between about 90-110% of the dendrimer of formula (I), (II), (III), (IV), (V), (VI) or (VII), or a pharmaceutically acceptable salt thereof, when assayed against a reference standard of known purity.

In some embodiments, the purity of the pharmaceutical composition is not less than about 75%, about 80%, about 85%, about 90% or about 95% as measured by size exclusion chromatography-UV (SEC-UV) analysis. In some embodiments, the purity of the pharmaceutical composition is not less than about 85% as measured by SEC-UV analysis.

In some embodiments, the pharmaceutical composition comprises less than about 10% w/w total impurities, for example, about 9%, about 8%, about 7%, about 6%, about 5%, about 4%, about 3%, about 2% or about 1%. In some embodiments, the pharmaceutical composition comprises less than between about 1% and 10% w/w total impurities. In some embodiments, the pharmaceutical composition comprises less than between about 1% and 5% w/w total impurities. In some embodiments, the pharmaceutical composition comprises less than about 3% w/w total impurities.

In some embodiments, the pharmaceutical composition comprises less than about 10%, about 9%, about 8%, about 7%, about 6%, about 5%, about 4%, about 3%, about 2%, or about 1% w/w free Compound A.

In some embodiments, the pharmaceutical composition comprises less than about 10%, about 9%, about 8%, about 7%, about 6%, about 5%, about 4%, about 3%, about 2%, about 1% or about 0.5% w/w any single unspecified impurity. In some embodiments, the pharmaceutical composition comprises about 0.5% w/w of any single unspecified impurity.

In some embodiments, the pharmaceutical composition comprises less than about 10%, about 9%, about 8%, about 7%, about 6%, about 5%, about 4%, about 3%, about 2% or about 1% w/w total free impurities.

In some embodiments, the pharmaceutical composition comprises not more than about 10%, about 9%, about 8%, about 7%, about 6%, about 5%, about 4%, about 3% about 2% or about 1% w/w acetic acid. In some embodiments, the pharmaceutical composition comprises not more than about 1.5% w/w acetic acid.

In some embodiments, the pharmaceutical composition has an average particle size determined by dynamic light scattering (DLS) of between about 15 and about 25 d·nm, for example, between about 17 and about 19 d·nm.

In some embodiments, the pharmaceutical composition has an a PDI as determined by dynamic light scattering (DLS) of between about 0.20 and about 0.30.

In some embodiments, the pharmaceutical composition comprises not more than about 10,000, about 9,000, about 8,000, about 7,000, about 6000, about 5,000, about 4,000, about 3,000, about 2,000, about 1,000 or about 500 particulates of greater than or equal to about 10 µm per 50 mL container upon reconstitution in a pharmaceutically acceptable diluent or solvent.

In some embodiments, the pharmaceutical composition comprises not more than about 6,000 particulates of greater than or equal to about 10 µm per 50 mL container upon reconstitution in a pharmaceutically acceptable diluent or solvent.

In some embodiments, the pharmaceutical composition comprises not more than about 1,000, about 900, about 800, about 700, about 600, about 500, about 400, about 300, about 200, about 100 or about 50 particulates of greater than or equal to about 25 µm per 50 mL container upon reconstitution in a pharmaceutically acceptable diluent or solvent. In some embodiments, the pharmaceutical composition comprises not more than about 600 particulates of greater than or equal to about 25 µm per 50 mL upon reconstitution in a pharmaceutically acceptable diluent or solvent.

In some embodiments, the osmolality of the pharmaceutical composition is between about 200 and about 400 mOsmol/kg, for example between about 250 and about 350 mOsol/kg, between about 260 and about 330 mOsmol/kg, or between about 270 and about 328 mOsmol/kg upon reconstitution in a pharmaceutically acceptable diluent or solvent.

In some embodiments, the pharmaceutical composition has an endotoxin limit of no more than about 0.1 about 0.09, about 0.08, about 0.07, about 0.06, about 0.05, about 0.04, about 0.03, about 0.02 or about 0.01 EU/mg.

In some embodiments, the acetic acid has a low water content, for example, less than about 1000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm, or less than about 50 ppm. In some embodiments, the acetic acid has a water content of less than about 10%, less than about 5%, less than about 4%, less than about 3%, less than about 2%, less than about 1%, less than about 0.5%, less than about 0.1%, less than about 0.09%, less than about 0.08%, less than about 0.07%, less than about 0.06%, less than about 0.05%, less than about 0.04%, less than about 0.03%, less than about 0.02% or less than about 0.01%.

In some embodiments, disclosed is a pharmaceutical composition comprising a lyophilized dendrimer of formula (I), (II), (III), (IV), (V), (VI) or (VII), or a pharmaceutically acceptable salt thereof, wherein the pharmaceutical composition comprises acetic acid. In some embodiments, disclosed is a pharmaceutical composition comprising a lyophilized dendrimer of formula (I), (II), (III), (IV), (V), (VI) or (VII), or a pharmaceutically acceptable salt thereof, wherein the pharmaceutical composition comprises not more than about 2% acetic acid. In some embodiments, the pharmaceutical composition comprising a lyophilized dendrimer of formula (I), (II), (III), (IV), (V), (VI) or (VII), or a pharmaceutically acceptable salt thereof, and comprises not more than about 2% acetic acid, and wherein the acetic acid comprises less than about 200 ppm of water.

In some embodiments, disclosed are methods of treating cancer comprising intravenously administering to a subject in need thereof a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent.

In one aspect, disclosed is a pharmaceutical composition comprising a lyophilized dendrimer of formula (I), (II), (III), (IV), (V), (VI), or (VII), or a pharmaceutically acceptable salt thereof, for use in treating cancer.

In one aspect, disclosed is the use of a pharmaceutical composition comprising a lyophilized dendrimer of formula (I), (II), (III), (IV), (V), (VI) or (VII), or a pharmaceutically acceptable salt thereof, in the manufacture of a medicament for treating a cancer.

In one aspect, disclosed are pharmaceutical compositions comprising a lyophilized dendrimer of formula (I), (II), (III), (IV), (V), (VI) or (VII), or a pharmaceutically acceptable salt thereof, for use in treating cancer.

The language "treat," "treating" and "treatment" includes the reduction or inhibition of enzyme or protein activity related to Bcl-2 and/or Bcl-XL or cancer in a subject, amelioration of one or more symptoms of cancer in a subject, or the slowing or delaying of progression of cancer in a subject. The language "treat," "treating" and "treatment" also includes the reduction or inhibition of the growth of a tumor or proliferation of cancerous cells in a subject.

The term "cancer" includes, but is not limited to, hematological (e.g., lymphomas, leukemia) and solid malignancies. The term "cancer" includes, for example, T-cell leukemias, T-cell lymphomas, acute lymphoblastic lymphoma (ALL), acute myelogenous leukemia (AML), chronic lymphocytic leukemia (CLL), small lymphocytic lymphoma (SLL), chronic myelogenous leukemia (CML), acute monocytic leukemia (AML), multiple myeloma, mantle cell lymphoma, diffuse large B cell lymphoma (DLBCL), Burkitt's lymphoma, Non-Hodgkin's lymphoma, follicular lymphoma and solid tumors, for example, non-small cell lung cancer (NSCLC, e.g., EGF mutant NSCLC, KRAS mutant NSCLC), small cell lung cancer (SCLC), breast cancer, neuroblastoma, ovarian cancer, prostate cancer, melanoma (e.g., BRAF mutant melanoma, KRAS mutant melanoma), pancreatic cancer, uterine, endometrial and colon cancer (e.g., KRAS mutant colon cancer, BRAF mutant colon cancer).

The term "subject" includes warm blooded mammals, for example, primates, dogs, cats, rabbits, rats, and mice. In some embodiments, the subject is a primate, for example, a human. In some embodiments, the subject is suffering from cancer or an immune disorder. In some embodiments, the subject is in need of treatment (e.g., the subject would benefit biologically or medically from treatment). In some embodiments, the subject is suffering from cancer. In some embodiments, the subject is suffering from a EGFR-M positive cancer (e.g., non-small cell lung cancer). In some embodiments, the EGFR-M positive cancer has a predominately T790M-positive mutation. In some embodiments, the EGFR-M positive cancer has a predominately T790M-negative mutation. In some embodiments, the subject is suffering from a hematological (e.g., lymphomas, leukemia) or solid malignancy, such as, for example, acute lymphoblastic lymphoma (ALL), acute myelogenous leukemia (AML), chronic lymphocytic leukemia (CLL), small lymphocytic lymphoma (SLL), chronic myelogenous leukemia (CML), acute monocytic leukemia (AMoL), multiple myeloma, mantle cell lymphoma, diffuse large B cell lymphoma (DLBCL), Burkitt's lymphoma, Non-Hodgkin's lymphoma, follicular lymphoma and solid tumors, for example, non-small cell lung cancer (NSCLC), small cell lung cancer (SCLC), breast cancer, neuroblastoma, prostate cancer, melanoma, pancreatic cancer, uterine, endometrial and colon cancer.

The language "effective amount" includes an amount of a dendrimer of formula (I), (II), (III), (IV), (V), (VI) or (VII), or a pharmaceutically acceptable salt thereof, or a second anti-cancer agent that will elicit a biological or medical response in a subject, for example, the reduction or inhibition of enzyme or protein activity related to Bcl-2 and/or Bcl-XL or cancer; amelioration of symptoms of cancer; or the slowing or delaying of progression of cancer. In some embodiments, the language "effective amount" includes the amount of a dendrimer of formula (I), (II), (III), (IV), (V), (VI) or (VII), or a pharmaceutically acceptable salt thereof, or second anti-cancer agent, that when administered to a subject, is effective to at least partially alleviate, inhibit, and/or ameliorate cancer or inhibit Bcl-2 and/or Bcl-XL, and/or reduce or inhibit the growth of a tumor or proliferation of cancerous cells in a subject.

In some embodiments, an effective amount of a dendrimer of formula (I), (II), (III), (IV), (V), (VI) or (VII), or a pharmaceutically acceptable salt thereof, may be between about 1 and about 500 mg/kg. In some embodiments, an effective amount of a dendrimer of formula (I), (II), (III), (IV), (V), (VI) or (VII), or a pharmaceutically acceptable salt thereof, may be between about 10 and about 300 mg/kg. In some embodiments, an effective amount of a dendrimer of formula (I), (II), (III), (IV), (V), (VI) or (VII), or a pharmaceutically acceptable salt thereof, may be between about 10 and about 100 mg/kg. In some embodiments, an effective amount of a dendrimer of formula (I), (II), (III), (IV), (V), (VI) or (VII), or a pharmaceutically acceptable salt thereof, may be between about 10 and about 60 mg/kg. In some embodiments, an effective amount of a disclosed a dendrimer of formula (I), (II), (III), (IV), (V), (VI) or (VII), or a pharmaceutically acceptable salt thereof, may be between about 10 and about 30 mg/kg. In some embodiments, an effective amount of a dendrimer of (1), (II), (III), (IV), (V), (VI) or (VII), or a pharmaceutically acceptable salt thereof, may be about 20 to about 100 mg/kg. In some embodiments, an effective amount of a dendrimer of formula (I), (II), (III), (IV), (V), (VI) or (VII), or a pharmaceutically acceptable salt thereof, may be about 10 mg/kg, about 30 mg/kg, about 40 mg/kg, about 50 mg/kg, about 60 mg/kg, about 70 mg/kg, about 80 mg/kg, about 90 mg/kg, about 100 mg/kg, about 300 mg/kg or about 145 mg/kg.

In one embodiment, disclosed is a method of treating cancer in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating lymphoma in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating Non-Hodgkin's lymphoma in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating DLBCL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating activated B cell DLBCL (ABC-DLBCL) in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating BTK-sensitive or BTK-insensitive DLBCL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In some embodiments, disclosed is a method of treating OCI-LY10 DLBCL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating MCL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating leukemia in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent, and separately, sequentially or simultaneously orally administering an effective amount of acalabrutinib, or a pharmaceutically acceptable salt thereof, to the subject. In one embodiment, disclosed is a method of treating CLL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a method of treating AML in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of acalabrutinib, or a pharmaceutically acceptable salt thereof, to the subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of cancer in a subject, wherein said treatment comprises the separate, sequentially or simultaneous (i) intravenous administration of the pharmaceutical composition comprising lyophilized dendrimer of formula (I), (II), (III), (IV), (V), (VI) or (VII), or a pharmaceutically acceptable salt thereof, reconstituted in a pharmaceutically acceptable diluent or solvent, and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of non-Hodgkin's lymphoma in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of DLBCL in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of activated B-cell DLBCL (ABC-DLBCL) in a subject, wherein said treatment comprises the separate, sequential or simultaneous (i) intravenous administration of the pharmaceutical composition of the dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of BTK-sensitive or BTK-insensitive DLBCL in a subject, wherein said treatment comprises the separate, sequential or simultaneous (i) intravenous administration of the pharmaceutical composition of the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of OCI-LY10 DLBCL in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of MCL in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of leukemia in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of CLL in a subject, wherein said treatment comprises the separate, sequential or simultaneous (i) intravenous administration of the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of AML in a subject, wherein said treatment comprises the separate, sequential or simultaneous (i) intravenous administration of pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of acalabrutinib to said subject. In one embodiment, disclosed is acalabrutinib for treatment of cancer in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of DLBCL in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of activated B-cell DLBCL (ABC-DLBCL) in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of BTK-sensitive or BTK-insensitive DLBCL in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of OCI-LY10 DLBCL in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of MCL in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of leukemia in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of CLL in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is acalabrutinib for treatment of AML in a subject, wherein said treatment comprises the separate, sequential or simultaneous (i) oral administration of acalabrutinib, and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject.

In one embodiment, disclosed is a method of treating cancer in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating lymphoma in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating Non-Hodgkin's lymphoma in a subject comprising intravenously administering a pharmaceutical composition comprising an effective amount of a lyophilized dendrimer of (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating DLBCL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating activated germinal center B cell DLBCL (GCB-DLBCL) in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating leukemia in a subject comprising intravenously administering a pharmaceutical composition comprising a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating CLL in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a method of treating AML in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously intravenously administering an effective amount of rituximab, or a pharmaceutically acceptable salt thereof, to the subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of cancer in a subject, wherein said treatment comprises the separate, sequential or simultaneous (i) intravenous administration of the pharmaceutical composition comprising the dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of lymphoma in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of non-Hodgkin's lymphoma in a subject, wherein said treatment comprises the separate, sequential or simultaneous (i) intravenous administration of the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of DLBCL in a subject, wherein said treatment comprises the separate, sequential or simultaneous: (ii) intravenous administration of a pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of germinal cell B-cell DLBCL (GCB-DLBCL) in a subject, wherein said treatment comprises the separate, sequential or simultaneous: (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of leukemia in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of CLL in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of AML in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) intravenous administration of rituximab to said subject. In one embodiment, disclosed is rituximab for treatment of cancer in a subject, wherein said treatment comprises the separate, sequential or simultaneous (i) intravenous administration of rituximab and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is rituximab for treatment of lymphoma in a subject, wherein said treatment comprises the separate, sequential or simultaneous (i) intravenous administration of rituximab and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is rituximab for treatment of non-Hodgkin's in a subject, wherein said treatment comprises the separate, sequential or simultaneous (i) intravenous administration of rituximab and (ii) intravenous administration of a lyophilized dendrimer of formula (I), (II), (III), (IV), (V), (VI) or (VII) or a pharmaceutically acceptable salt thereof, reconstituted in a pharmaceutically acceptable diluent or solvent to said subject. In one embodiment, disclosed is rituximab for treatment of DLBCL in a subject, wherein said treatment comprises the separate, sequential or simultaneous (i) intravenous administration of rituximab and (ii) intravenous administration of a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is rituximab for treatment of germinal cell B-cell DLBCL (GBC-DLBCL) in a subject, wherein said treatment comprises the separate, sequential or simultaneous (i) intravenous administration of rituximab and (ii) intravenous administration of a lyophilized dendrimer of formula (I), (II), (III), (IV), (V), (VI) or (VII), or a pharmaceutically acceptable salt thereof to said subject. In one embodiment, disclosed is rituximab for treatment of leukemia in a subject, wherein said treatment comprises the separate, sequential or simultaneous (i) intravenous administration of rituximab and (ii) a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is rituximab for treatment of CLL in a subject, wherein said treatment comprises the separate, sequential or simultaneous (i) intravenous administration of rituximab and (ii) a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject. In one embodiment, disclosed is rituximab for treatment of AML in a subject, wherein said treatment comprises the separate, sequential or simultaneous (i) intravenous administration of rituximab and (ii) a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject.

In one embodiment, disclosed are methods of treating cancer in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of vistusertib (AZD2014), or a pharmaceutically acceptable salt thereof, to the subject. In one embodiment, disclosed are methods of treating small cell lung cancer in a subject comprising intravenously administering a pharmaceutical composition comprising an effective amount of a lyophilized dendrimer of formula (I), (II), (III), (IV), (V), (VI) or (VII), or a pharmaceutically acceptable salt thereof, reconstituted in a pharmaceutically acceptable diluent or solvent; and separately, sequentially or simultaneously orally administering an effective amount of vistusertib (AZD2014), or a pharmaceutically acceptable salt thereof, to the subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of cancer in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of vistusertib (AZD2014) to said subject. In one embodiment, disclosed is a pharmaceutical composition comprising a lyophilized dendrimer of formula (I), (II), (III), (IV), (V), (VI) or (VII), or a pharmaceutically acceptable salt thereof, for treatment of small-cell lung cancer in a subject, wherein said treatment comprises the separate, sequential or simultaneous (i) intravenous administration of the pharmaceutical composition comprising the lyophilized dendrimer of formula (I), (II), (III), (IV), (V), (VI) or (VII), or a pharmaceutically acceptable salt thereof, reconstituted in a pharmaceutically acceptable diluent or solvent; and (ii) oral administration of vistusertib (AZD2014) to said subject. In one embodiment, disclosed is vistusertib (AZD2014), or a pharmaceutically acceptable salt thereof, for treatment of cancer in a subject, wherein said treatment comprises the separate, sequential or simultaneous (i) oral administration of vistusertib (AZD2014); and (ii) intravenous administration of a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent, to said subject. In one embodiment, disclosed is vistusertib (AZD2014), or a pharmaceutically acceptable salt thereof, for treatment of small-cell lung cancer in a subject, wherein said treatment comprises the separate, sequential or simultaneous (i) oral administration of vistusertib, or a pharmaceutically acceptable salt thereof, and (ii) a pharmaceutical composition comprising a lyophilized dendrimer of formula (I), (II), (III), (IV), (V), (VI) or (VII), or a pharmaceutically acceptable salt thereof, reconstituted in a pharmaceutically acceptable diluent or solvent to said subject.

In one aspect, disclosed are methods for inhibiting Bcl-2 and/or Bcl-XL in a subject in need thereof, comprising intravenously administering to the subject a pharmaceutical composition comprising an effective amount of a dendrimer of formula (I), (II), (III), (IV), (V), (VI) or (VII), or a pharmaceutically acceptable salt thereof, reconstituted in a pharmaceutically acceptable diluent or solvent.

In one aspect, disclosed is a pharmaceutical composition comprising a lyophilized dendrimer of formula (I), (II), (III), (IV), (V), (VI) or (VII), or a pharmaceutically acceptable salt thereof, for use in inhibiting Bcl-2 and/or Bcl-XL.

In one aspect, disclosed is the use of a pharmaceutical composition comprising a lyophilized dendrimer of formula (I), (II), (III), (IV), (V), (VI) or (VII), or a pharmaceutically acceptable salt thereof, in the manufacture of a medicament for inhibiting Bcl-2 and/or Bcl-XL.

In one aspect, disclosed are pharmaceutical compositions comprising a lyophilized dendrimer of formula (I), (II), (III), (IV), (V), (VI) or (VII), or a pharmaceutically acceptable salt thereof, for use in inhibiting Bcl-2 and/or Bcl-XL.

The term "Bcl-2" refers to B-cell lymphoma 2 and the term "Bcl-XL" refers to B-cell lymphoma extra-large, which anti-apoptotic members of the BCL-2 family of proteins.

In some embodiments, disclosed is a kit of parts comprising one or more containers comprising a lyophilized pharmaceutical composition comprising a dendrimer of formula (I), (II), (III), (IV), (V), (VI) or (VII), or a pharmaceutically acceptable salt thereof, and instructions for use. In some embodiments, the kit further comprises one or more containers of a pharmaceutically acceptable diluent or solvent. The term "container" includes any container suitable for enclosing the lyophilized pharmaceutical compositions and pharmaceutically acceptable diluent or solvents, for example, vials, IV bags, cannisters, envelopes, bottles, syringes and the like. In some embodiments, the kits further comprise components required for administering the lyophilized pharmaceutical compositions comprising a dendrimer of formula (I), (II), (III), (IV), (V), (VI) or (VII), or a pharmaceutically acceptable salt thereof, for example, IV bags, needles, syringes, tubing and the like.

In some embodiments, the pharmaceutically acceptable diluent or solvent comprises a citrate buffer solution. In some embodiments, the citrate buffer is at pH 5. In some embodiments, the citrate buffer comprises citric acid monohydrate, sodium citrate dihydrate and dextrose anhydrous. In some embodiments, the diluent or solvent is a 50 mM citrate buffer at pH 5 in 5% (w/w) dextrose.

In some embodiments, the pharmaceutically acceptable diluent or solvent comprises an acetate buffer solution. In some embodiments, the acetate buffer solution is at pH 5. In some embodiments, the acetate buffer solution comprises acetic acid, sodium acetate anhydrous and dextrose. In some embodiments, the acetate buffer comprises 100 mM acetate buffer (pH 5) in 2.5% (w/w) dextrose.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:
(i) all syntheses were carried out at ambient temperature, i.e. in the range 17 to 25° C. and under an atmosphere of an inert gas such as nitrogen unless otherwise stated;
(ii) evaporations were carried out by rotary evaporation under reduced pressure, using Buchi or Heidolph equipment;
(iii) lyophilization was carried out using a Labconco FreeZone 6 Plus freeze dry system or other systems described herein or other appropriate system as determined by one of skill in the art;
(iv) size exclusion chromatography purifications were performed using columns packed with Sephadex LH-20 beads;
(v) preparative chromatography was performed on a Gilson Prep GX-271 system with UV-triggered collection, using a Waters XBridge BEH C18 (5 µM, 30×150 mm) column;
(vi) ultrafiltration purifications were performed using a Cole-Parmer gear pump drive system connected to a membrane casette (Merck Millipore Pellicon 3, 0.11 m2, 10 kDa).
(vii) analytical chromatography was performed on a Waters Alliance 2695 Separation Module with PDA detection;
(viii) yields, where present, are not necessarily the maximum attainable;
(ix) in general, the structures of end products of the dendrimers were confirmed by NMR spectroscopy; $^1$H and $^{19}$F NMR chemical shift values were measured on the delta scale, [proton magnetic resonance spectra were determined using a Bruker Avance 300 (300 MHz) instrument]; measurements were taken at ambient temperature unless otherwise specified; 1H NMR use the solvent residual peak as the internal standard and the following abbreviations: s, singlet; d, doublet; t, triplet; q, quartet; m, multiplet; dd, doublet of doublets; ddd, doublet of doublet of doublet; dt, doublet of triplets; br s, broad singlet;
(x) in general, dendrimer end products were also characterized by HPLC, using a Waters Alliance 2695 Separation Module with PDA detection, connected to either a Waters XBridge C8 (3.5 µm, 3×100 mm) or a Phenomenex Aeris C8 (3.6 µm, 2.1×100 mm) column;
(xi) intermediate purity was assessed by mass spectroscopy following liquid chromatography (LC-MS); using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm), for basic analysis the column used was a Waters Acquity BEH C18 (1.7 μm, 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 min (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 μm, 2.1×30 mm), for basic analysis the column used was a Waters Acquity BEH C18 (1.7 μm, 2.1×30 mm); The reported molecular ion corresponds to the [M+H]+ unless otherwise specified; for molecules with multiple isotopic patterns (Br, Cl, etc.) the reported value is the one obtained with highest intensity unless otherwise specified.

(xii) the following abbreviations have been used:
ACN Acetonitrile
BHA Benzhydrylamine
BOC tert-butyloxycarbonyl
CoA Certificate of Analysis
DGA Diglycolic acid
DIPEA Diisopropylethylamine
DMF Dimethylformamide
DMSO Dimethylsulfoxide
FBA 4-Fluorobenzoic acid
Glu Glutaric
HP-β-CD hydroxypropyl-beta-cyclodextrin
MeOH Methanol
MIDA Methyliminodiacetic acid
MSA Methanesulfonic acid
MTBE Methyl tert-butyl ether
MW Molecular Weight
NMM N-Methylmorpholine
PBS Phosphate buffered saline
PEG Polyethylene Glycol
PTFE Polytetrafluoroethylene
PyBOP Benzotriazol-1-yl-oxytripyrrolidinophosphonium hexafluorophosphate
QS/qs Quantum sufficit (the amount which is needed)
SBE-β-CD Sulfobutyl ether beta-cyclodextrin (Captisol®)
TDA Thiodiglycolic acid
TFA Trifluoroacetic acid
WFI Water for injection WFI As used in the Examples, the term "BHALys" refers to 2,6-diamino-N-benzhydrylhexanamide linked to lysine. BHA has the structure:

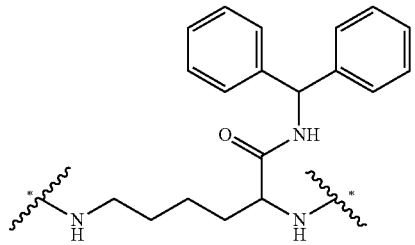 [SMILES: *NCCCCC(N*)C(=O)NC(c1ccccc1)c1ccccc1]

wherein * indicates a covalent attachment to the lysine building blocks. The term "Lys" refers to the building units of the dendrimer and has the structure:

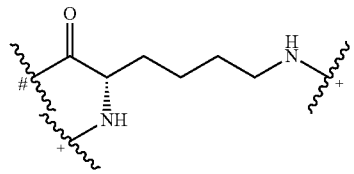

in which # indicates covalent attachment to an amine moiety of BHALys or an amino moiety of a Lys building unit, and + indicates a covalent attachment to a carbonyl moiety of a Lys building unit or a covalent attachment to PEG or the linker attached to the active agent.

For convenience, only the surface generation of building units in the dendrimers of the Examples is included in the name of the dendrimer. In addition, the symbol ‡ in the name refers to the theoretical number of ε-amino groups available for conjugation to PEG and the symbol † in the name refers to the theoretical number of α-amino groups on the dendrimer available for conjugation to the linker attached to the active agent, respectively. As an example, the name "BHALys[Lys]$_{32†}$[α-TDA-Compound A]$_{32}$[ε-PEG$_{2100, 2200}$]$_{32‡}$" refers to a fifth generation dendrimer with the BHALys core, Lys building units in the surface (fifth) layer, approximately 32 Compound A conjugated to the α-amino groups of the Lys surface building units with thiodiacetic acid linkers, approximately 32 PEG groups with and average molecular weight of between 2100 and 2200 conjugated to the ε-amino groups of the Lys surface building units.

Example 1: Preparation and Characterization of Compounds 1 and 2

1. Preparation and Characterization of BHALvs[Lys]$_{32}$[α-NH$_2$TFA]$_{32}$[ε-PEG-2000]$_{32‡}$ Note: 32‡ relates to the theoretical number of ε-amino groups available for substitution with PEG$_{\sim 2000}$. The actual mean number of PEG$_{\sim 2000}$ groups attached to the BHALys [Lys]$_{32}$ was determined experimentally by $^1$H NMR (see below section in this present Example entitled Characterization of BHALys[Lys]$_{32}$[α-NH$_2$-TFA]$_{32}$[ε-PEG~2000]$_{32‡}$).

(a) BHALvs[Boc]$_2$

Solid α,ε-(t-Boc)$_2$-(L)-lysine p-nitrophenol ester (2.787 kg, 5.96 mol) was added to a solution of aminodiphenylmethane (benzhydrylamine) (0.99 kg, 5.4 mol) in anhydrous acetonitrile (4.0 L), DMF (1.0 L) and triethylamine (1.09 kg) over a period of 15 min. The reaction mixture was agitated at 20° C. overnight. The reaction mixture was then warmed to 35° C. and aqueous sodium hydroxide (0.5 N, 10 L) was added slowly over 30 min. The mixture was stirred for an additional 30 min then filtered. The solid cake was washed with water and dried to a constant weight (2.76 kg, 5.4 mol) in 100% yield. $^1$H NMR (CD$_3$OD) δ 7.3 (m, 10H, Ph Calc 10H); 6.2 (s, 1H, CH-Ph$_2$ Calc 1H); 4.08 (m, α-CH, 1H); 3.18 (br, ε—CH$_2$) and 2.99 (m, ε—CH$_2$ 2H); 1.7-1.2 (br, β,γ,δ-CH$_2$) and 1.43 (s, tBu) total for β,γ,δ-CH$_2$ and tBu 25H Calc 24H. MS (ESI +ve) found 534.2 [M+Na]$^+$ calc for C$_{29}$H$_{41}$N$_3$O$_5$Na [M+Na]$^+$ 534.7.

(b) BHALys[HCl]$_2$

A solution of concentrated HCl (1.5 L) in methanol (1.5 L) was added slowly, in three portions, to a stirred suspension of BHALys[Boc]$_2$ (780.5 g, 1.52 mol) in methanol (1.5

L) at a rate to minimize excessive frothing. The reaction mixture was stirred for an additional 30 min, then concentrated under vacuum at 35° C. The residue was taken up in water (3.4 L) and concentrated under vacuum at 35° C. twice, then stored under vacuum overnight. Acetonitrile (3.4 L) was then added and the residue was again concentrated under vacuum at 35° C. to give BHALys[HCl]$_2$ as a white solid (586 g, 1.52 mol) in 100% yield. $^1$H NMR (D$_2$O) δ 7.23 (br m, 10H, Ph Calc 10H); 5.99 (s, 1H, CH-Ph$_2$ Calc 1H); 3.92 (t, J=6.5 Hz, α-CH, 1H, Calc 1H); 2.71 (t, J=7.8 Hz, ε-CH$_2$, 2H, Calc 2H); 1.78 (m, β,γ,δ-CH$_2$, 2H), 1.47 (m, β,γ,δ-CH$_2$, 2H), and 1.17 (m, β,γ,δ-CH$_2$, 2H, total 6H Calc 6H). MS (ESI +ve) found 312 [M+H]+ calc for C$_{19}$H$_{26}$N$_3$O [M+H]+ 312.

(c) BHALys[Lys]$_2$[Boc]$_4$

To a suspension of BHALys[HCl]$_2$ (586 g, 1.52 mmol) in anhydrous DMF (3.8 L) was added triethylamine (1.08 kg) slowly to maintain the reaction temperature below 30° C. Solid α,ε-(t-Boc)$_2$-(L)-lysine p-nitrophenol ester (1.49 kg) was added in three portions, slowly and with stirring for 2 hours between additions. The reaction was allowed to stir overnight. An aqueous solution of sodium hydroxide (0.5 M, 17 L) was added slowly to the well stirred mixture, and stirring was maintained until the solid precipitate was freely moving. The precipitate was collected by filtration, and the solid cake was washed well with water (2×4 L) then acetone/water (1:4, 2×4 L). The solid was slurried again with water then filtered and dried under vacuum overnight to give BHALys [Lys]$_2$[Boc]$_4$ (1.51 kg) in 100% yield. $^1$H NMR (CD$_3$OD) δ 7.3 (m, 10H, Ph Calc 10H); 6.2 (s, 1H, CH-Ph$_2$ Calc 1H); 4.21 (m, α-CH), 4.02 (m, α-CH) and 3.93 (m, α-CH, total 3H, Calc 3H); 3.15 (m, ε—CH$_2$) and 3.00 (m, ε—CH$_2$ total 6H, Calc 6H); 1.7-1.3 (br, β,γ,δ-CH$_2$) and 1.43 (s, tBu) total for β,γ,δ-CH$_2$ and tBu 57H, Calc 54H. MS (ESI +ve) found 868.6 [M-Boc]+; 990.7 [M+Na]+ calc for C$_{51}$H$_{81}$N$_7$O$_{11}$Na [M+Na]+991.1.

(d) BHALys[Lys]$_2$[HCl]$_4$

BHALys[Lys]$_2$[Boc]$_4$ (1.41 kg, 1.46 mol) was suspended in methanol (1.7 L) with agitation at 35° C. Hydrochloric acid (1.7 L) was mixed with methanol (1.7 L), and the resulting solution was added in four portions to the dendrimer suspension and left to stir for 30 min. The solvent was removed under reduced pressure and worked up with two successive water (3.5 L) strips followed by two successive acetonitrile (4 L) strips to give BHALys[Lys]$_2$[HCl]$_4$ (1.05 Kg, 1.46 mmol) in 102% yield. $^1$H NMR (D$_2$O) δ 7.4 (br m, 10H, Ph Calc 10H); 6.14 (s, 1H, CH-Ph$_2$ Calc 1H); 4.47 (t, J=7.5 Hz, α-CH, 1H), 4.04 (t, J=6.5 Hz, α-CH, 1H), 3.91 (t, J=6.8 Hz, α-CH, 1H, total 3H, Calc 3H); 3.21 (t, J=7.4 Hz, ε-CH$_2$, 2H), 3.01 (t, J=7.8 Hz, ε-CH$_2$, 2H) and 2.74 (t, J=7.8 Hz, ε-CH$_2$, 2H, total 6H, Calc 6H); 1.88 (m, β,γ,δ-CH$_2$), 1.71 (m, β,γ,δ-CH$_2$), 1.57 (m, β,γ,δ-CH$_2$) and 1.35 (m, β,γ,δ-CH$_2$ total 19H, Calc 18H).

(e) BHALys[Lys]$_4$[Boc]$_8$

BHALys[Lys]$_2$[HCl]$_4$ (1.05 Kg, 1.47 mol) was dissolved in DMF (5.6 L) and triethylamine (2.19 L). The α,ε-(t-Boc)$_2$-(L)-lysine p-nitrophenol ester (2.35 Kg, 5.03 mol) was added in three portions and the reaction stirred overnight at 25° C. A NaOH (0.5M, 22 L) solution was added and the resulting mixture filtered, washed with water (42 L) and then air dried. The solid was dried under vacuum at 45° C. to give BHALys [Lys]$_4$[Boc]$_8$ (2.09 Kg, 1.11 mol) in 76% yield. $^1$H NMR (CD$_3$OD) δ 7.3 (m, 10H, Ph Calc 10H); 6.2 (s, 1H, CH-Ph$_2$ Calc 1H); 4.43 (m, α-CH), 4.34 (m, α-CH), 4.25 (m, α-CH) and 3.98 (br, α-CH, total 7H, Calc 7H); 3.15 (br, ε—CH$_2$) and 3.02 (br, ε-CH$_2$ total 14H, Calc 14H); 1.9-1.2 (br, β,γ,δ-CH$_2$) and 1.44 (br s, tBu) total for β,γ,δ-CH$_2$ and tBu 122H, Calc 144H.

(f) BHALys[Lys]$_4$[TFA]$_8$

To a stirred suspension of BHALys[Lys]$_4$[Boc]$_8$ (4 g, 2.13 mmol) in DCM (18 mL) was added TFA (13 mL) at 0° C. The solids dissolved, and the solution was stirred overnight under an atmosphere of argon. The solvents were removed under vacuum, and residual TFA was removed by trituration with diethyl ether (100 mL). The product was redissolved in water then freeze dried to give BHALys[Lys]$_4$[TFA]$_8$ as an off-white solid (4.27 g, 2.14 mmol) in 101% yield. $^1$H NMR (D$_2$O) δ 7.21 (br m, 10H, Ph Calc 10H); 5.91 (s, 1H, CH-Ph$_2$ Calc 1H); 4.17 (t, J=7.4 Hz, α-CH, 1H), 4.09 (t, J=7.1 Hz, α-CH, 1H), 4.02 (t, J=7.2 Hz, α-CH, 1H, 3.84 (t, J=6.5 Hz, α-CH, 2H), 3.73 (t, J=6.7 Hz, α-CH, 1H), 3.67 (t, J=6.7 Hz, α-CH, 1H, total 7H, Calc 7H); 3.0 (m, ε—CH$_2$), 2.93 (m, ε—CH$_2$) and 2.79 (b, ε—CH$_2$, total 15H, Calc 14H); 1.7 (br, β,γ,δ-CH$_2$), 1.5 (br, β,γ,δ-CH$_2$), 1.57 (m, β,γ,δ-CH$_2$) and 1.25 (br, β,γ,δ-CH$_2$ total 45H, Calc 42H). MS (ESI +ve) found 541.4 [M+2H]$^{2+}$; calc for C$_{55}$H$_{99}$N$_{15}$O$_7$[M+2H]$^{2+}$ 541.2.

(g) BHALys[Lys]$_8$[Boc]$_{16}$

A solution of α,ε-(t-Boc)$_2$-(L)-lysine p-nitrophenol ester (1.89 g, 4.05 mmol) in DMF (25 mL) was added to a solution of BHALys [Lys]$_4$[NH$_2$TFA]$_8$ (644 mg, 0.32 mmol) and triethylamine (0.72 mL, 5.2 mmol) in DMF (25 mL) and the reaction was left to stir overnight under an argon atmosphere. The reaction mixture was poured onto ice/water (500 mL) then filtered and the collected solid was dried overnight under vacuum. The dried solid was washed thoroughly with acetonitrile to give BHALys[Lys]$_8$[Boc]$_{16}$ as an off white solid (0.82 g, 0.22 mmol) in 68% yield. $^1$H NMR (CD$_3$OD) δ 7.3 (m, 10H, Ph Calc 10H); 6.2 (br s, 1H, CH-Ph$_2$ Calc 1H); 4.48 (br, α-CH), 4.30 (br, α-CH) and 4.05 (br, α-CH, total 16H Calc 15H); 3.18 (br, ε—CH$_2$) and 3.02 (m, ε—CH$_2$ total 31H, Calc 30H); 1.9-1.4 (br, β,γ,δ-CH$_2$) and 1.47 (br s, tBu) total for β,γ,δ-CH$_2$ and tBu 240H, Calc 234H. MS (ESI +ve) found 3509 [M+H-(Boc)$_2$]+ calc for C$_{173}$H$_3$O$_6$N$_{31}$O$_{43}$ [M+H-(Boc)$_2$]+3508.5; 3408 [M+H-(Boc)$_3$]+ calc for C$_{168}$H$_{298}$N$_{31}$O$_{41}$ [M+H-(Boc)$_3$]+3408.4.

(h) BHALys[Lys]$_8$[TFA]$_{16}$

A solution of TFA/DCM (1:1, 19 mL) was added slowly to a stirred suspension of BHALys[Lys]$_8$[Boc]$_{16}$ (800 mg, 0.22 mmol) in DCM (25 mL). The solids dissolved, and the solution was stirred overnight under an atmosphere of argon. The solvents were removed under vacuum, and residual TFA was removed by repetitive freeze drying of the residue, to give BHALys [Lys]$_8$[TFA]$_{16}$ as an off-white lyophylate (848 mg, 0.22 mmol) in 100% yield. $^1$H NMR (D$_2$O) δ 7.3 (br m, 10H, Ph Calc 10H); 6.08 (s, 1H, CH-Ph$_2$ Calc 1H); 4.3 (m, α-CH), 4.18 (m, α-CH), 4.0 (m, α-CH) and 3.89 (m, α-CH, total 16H, Calc 15H); 3.18 (br, ε—CH$_2$) and 2.94 (m, ε—CH$_2$ total 32H, Calc 30H); 1.9 (m, β,γ,δ-CH$_2$), 1.68 (m, β,γ,δ-CH$_2$) and 1.4 (m, β,γ,δ-CH$_2$ total 99H, Calc 90H). MS (ESI +ve) found 2106 [M+H]+ calc for C$_{103}$H$_{194}$N$_{31}$O$_{15}$ [M+H]+ 2106.9.

(i) BHALys[Lys]$_{16}$[Boc]$_{32}$

A solution of α,ε-(t-Boc)$_2$-(L)-lysine p-nitrophenol ester (1.89 g, 4.05 mmol) in DMF (25 mL) was added to a solution of BHALys [Lys]$_8$[TFA]$_{16}$ (644 mg, 0.32 mmol) and triethylamine (0.72 mL, 5.2 mmol) in DMF (25 mL) and the reaction was left to stir overnight under an argon atmosphere. The reaction was poured onto ice/water (500 mL) then filtered and the collected solid was dried overnight under vacuum. The dried solid was washed thoroughly with acetonitrile to give BHALys[Lys]$_{16}$[Boc]$_{32}$ as an off white solid (0.82 g, 0.2 2 mmol) in 68% yield. $^1$H NMR (CD$_3$OD) δ 7.28 (m, 9H, Ph Calc 10H); 6.2 (br s, 1H, CH-Ph$_2$ Calc 1H); 4.53 (br, α-CH), 4.32 (br, α-CH) and 4.05 (br, α-CH, total 35H, Calc 31H); 3.18 (br, ε—CH$_2$) and 3.04 (m, ε—CH$_2$ total 67H, Calc 62H); 1.9-1.5 (br, β,γ,δ-CH$_2$) and 1.47 (br s, tBu) total for β,γ,δ-CH$_2$ and tBu 474H Calc, 474H. MS (ESI +ve) found 6963 [M+H-(Boc)$_4$]+ calc for C$_{339}$H$_{610}$N$_{63}$O$_{87}$ [M+H-(Boc)$_4$]$^+$6960.9; 6862 [M+H-(Boc)$_5$]$^+$ calc for C$_{334}$H$_{604}$N$_{63}$O$_{85}$ [M+H-(Boc)$_5$]$^+$6860.8.

(j) BHALys[Lys]$_{16}$[TFA]$_{32}$

A solution of TFA/DCM (1:1, 19 mL) was added slowly to a stirred suspension of BHALys[Lys]$_{16}$[Boc]$_{32}$ (800 mg, 0.11 mmol) in DCM (25 mL). The solids dissolved, and the solution was stirred overnight under an atmosphere of argon. The solvents were removed under vacuum, and residual TFA was removed by repetitive freeze drying of the residue, to give BHALys[Lys]$_{16}$[TFA]$_{32}$ as an off-white lyophylate (847 mg, 0.11 mmol) in 100% yield. $^1$H NMR (D$_2$O) δ 7.3 (br m, 11H, Ph Calc 10H); 6.06 (s, 1H, CH-Ph$_2$ Calc 1H); 4.3 (m, α-CH), 4.19 (m, α-CH), 4.0 (m, α-CH) and 3.88 (m, α-CH, total 35H, Calc 31H); 3.15 (br, ε—CH$_2$) and 2.98 (m, ε—CH$_2$ total 69H, Calc 62H); 1.88 (m, β,γ,δ-CH$_2$), 1.7 (m, β,γ,δ-CH$_2$) and 1.42 (m, β,γ,δ-CH$_2$ total 215H, Calc 186H). MS (ESI +ve) found 4158 [M+H]$^+$ calc for C$_{199}$H$_{386}$N$_{63}$O$_{31}$ [M+H]+ 4157.6

(k) HO-Lys(α-BOC)(ε-PEG$_{2100}$)

DIPEA (0.37 mL, 2.10 mmol) was added to an ice-cooled mixture of NHS-PEG$_{2100}$

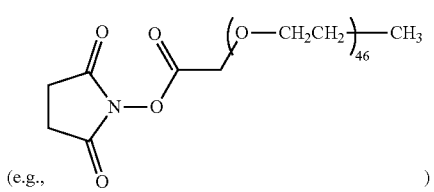

(e.g., )

(2.29 g, 1.05 mmol) and N-α-t-BOC-L-lysine (0.26 g, 1.05 mmol) in DMF (20 mL). The stirred mixture was allowed to warm to room temperature overnight then any remaining solids were filtered (0.45 μm PALL acrodisc) before removing the solvent in vacuo. The residue was taken up in ACN/H$_2$O (1:3, 54 mL) and purified by PREP HPLC (Waters XBridge C18, 5 μm, 19×150 mm, 25 to 32% ACN (5-15 min), 32 to 60% ACN (15 to 20 min), no buffer, 8 mL/min, RT=17 min), providing 1.41 g (56%) of HO-Lys (BOC)(PEG$_{2100}$). $^1$H NMR (CD$_3$OD) δ 3.96-4.09 (m, 1H), 3.34-3.87 (m, 188H); 3.32 (s, 3H), 3.15 (q, J=6.0 Hz, 2H), 2.40 (t, J=6.2 Hz, 2H), 1.28-1.88 (m, 6H), 1.41 (s, 9H).

(l) BHALys[Lys]$_{32}$[α-BOC]$_{32}$[ε-PEG2100]$_{32‡}$

To a stirred mixture of BHALys[Lys]$_{16}$[TFA]$_{32}$ (0.19 g, 24 μmol) in DMF (20 mL) was added DIPEA (0.86 mL, 4.86 mmol). This mixture was then added dropwise to a stirred mixture of PyBOP (0.62 g, 1.20 mmol) and Lys(BOC) (PEG$_{2100}$) (2.94 g, 1.20 mmol) in DMF (20 mL) at room temperature. The reaction mixture was left to stir overnight, then diluted with water (200 mL). The aqueous mixture was subjected to a centramate filtration (5 k membrane, 20 L water). The retentate was freeze dried, providing 1.27 g (73%) of desired dendrimer. HPLC (C8 XBridge, 3×100 mm, gradient: 5% ACN (0-1 min), 5-80% ACN/H2O) (1-7 min), 80% ACN (7-12 min), 80-5% ACN (12-13 min), 5% ACN (13-15 min), 214 nm, 0.1% TFA) Rf (min)=8.52. 1H-nmr (300 MHz, D$_2$O) δ (ppm): 1.10-2.10 (m, Lys CH$_2$ (β, χ, δ) and BOC, 666H), 3.02-3.36 (m, Lys CH$_2$ (E), 110H), 3.40 (s, PEG-OMe, 98H), 3.40-4.20 (m, PEG-OCH$_2$, 5750H+Lys CH surface, 32H), 4.20-4.50 (m, Lys, CH internal 32H), 7.20-7.54 (m, BHA, 8H). $^1$H NMR indicates approximately 29 PEGs.

(m) BHALys[Lys]$_{32}$[α-TFA]$_{32}$[ε-PEG$_{2100}$]$_{32‡}$ 1.27 g (17.4 μmol) of BHALys[Lys]$_{32}$[α-BOC]$_{32}$[ε-PEG$_{2100}$]$_{32}$ was stirred in TFA/DCM (1:1, 20 mL) at room temperature overnight. The volatiles were removed in vacuo, then the residue was taken up in water (30 mL). The mixture was then concentrated. This process was repeated two more times before being freeze dried, providing 1.35 g (106%) of desired product as a viscous colourless oil. HPLC (C8 XBridge, 3×100 mm, gradient: 5% ACN (0-1 min), 5-80% ACN/H$_2$O) (1-7 min), 80% ACN (7-12 min), 80-5% ACN (12-13 min), 5% ACN (13-15 min), 214 nm, 0.1% TFA) Rf (min)=8.51. $^1$H-nmr (300 MHz, D$_2$O) δ (ppm): 1.22-2.08 (Lys CH$_2$ ((β, χ, δ), 378H), 3.00-3.26 (Lys CH$_2$ (ε), 129H), 3.40 (PEG-OMe, 96H), 3.45-4.18 (PEG-OCH$_2$, 5610H+Lys CH surface, 32H), 4.20-4.46 (Lys, CH internal, 33H), 7.24-7.48 (8H, BHA). $^1$H NMR indicates approximately 29 PEGs.

(n) Characterization of BHALys[Lys]$_{32}$[α-NH$_2$TFA]$_{32}$[ε-PEG$_{\sim 2000}$]$_{32‡}$ Table 1 illustrates the various batches of BHALys[Lys]$_{32}$ [α-NH$_2$TFA]$_{32}$[ε-PEG$_{\sim 2000}$]$_{32\#}$ were used in the synthesis of Compounds 1 and 2, below, which have slightly different PEG lengths. The actual number of PEG chains on the dendrimer is also calculated by proton NMR.

TABLE 1

Various Batches of BHALys[Lys]$_{32}$[α-NH$_2$TFA]$_{32}$[ε-PEG$_{\sim 2000}$]$_{32‡}$

| Batch | Scale | PEG length from CoA (Da) | Number of PEGs (x) on BHALys[Lys]$_{32}$[α-NH$_2$•TFA]$_{32}$[ε-PEG$_{\sim 2000}$]$_x$ (from proton NMR*) | Estimated MW** (kDa) |
|---|---|---|---|---|
| 1 | 101 mg | 2200 | 29 | 75.7 |
| 2 | 98 mg | 2200 | 29 | 75.7 |
| 3 | 74.8 g | 2100 | 29 | 72.8 |
| 4 | 137 mg | 2200 | 29 | 75.7 |
| 5 | 1.19 g | 2100 | 31 | 77.0 |
| 6 | 18.98 g | 2100 | 29 | 72.8 |

*Number of PEGs is calculated from the proton NMR. For batch 1: No. of PEGs = Number (integration) of protons in PEG region of NMR (3.4-4.2 ppm)/Average (mean) number of protons per PEG chain (CoA PEG/44 Da x 4H)
=5706H/(2200/44 x 4)
=28.53 (approx. 29 PEG units)
**Molecular Weight estimated by adding MW of various components. For batch 1:
Total MW = Mw of dendrimer + Mw of TFA + Mw of PEG
=BHALys[Lys]$_{32}$ + 32(TFA) + 29(PEG)
=8,258 + 3,648 + 63800
=~75.7 kPa The proton NMR for the various batches of BHALys [Lys]$_{32}$[α-NH$_2$TFA]$_{32}$[ε-PEG$_{\sim 2000}$]$_{32‡}$ is presented in the Table 2:

TABLE 2

Proton NMR Data for Various Batches of
BHALys[Lys]$_{32}$[α-NH$_2$TFA]$_{32}$[ε-PEG$_{\sim2000}$]$_{32\ddagger}$

| Batch | Scale | Proton NMR of BHALys[Lys]$_{32}$[α-NH$_2$•TFA]$_{32}$[ε-PEG$_{\sim2000}$]$_x$ |
|---|---|---|
| 1 | 101 mg | 1.22-2.08 (Lys CH$_2$(β, χ, δ), 378H), 3.00-3.26 (Lys CH$_2$ (α), 129H), 3.40 (PEG-OMe, 96H), 3.45-4.18 (PEG-OCH$_2$, 5610H + Lys CH surface, 32H), 4.20-4.46 (Lys, CH internal, 33H), 7.24-7.48 (8H, BHA). |
| 2 | 98 mg | As for batch 1 |
| 3 | 74.8 g | 1.02-2.18 (Lys CH$_2$(β, χ, δ), 378H), 2.94-3.36 (Lys CH$_2$ (α), 129H), 3.41 (PEG-OMe, 93H), 3.45-4.18 (PEG-OCH$_2$, 5432H + Lys CH surface, 32H), 4.18-4.50 (Lys, CH internal, 32H), 7.12-7.64 (9H, BHA). |
| 4 | 137 mg | As for batch 1 |
| 5 | 1.19 g | 1.02-2.16 (Lys OH$_2$(β, χ, δ), 378H), 2.93-3.36 (Lys CH$_2$ (α), 129H), 3.41 (PEG-OMe, 101H), 3.45-4.18 (PEG-OCH$_2$, 5908H + Lys CH surface, 32H), 4.18-4.50 (Lys, CH internal, 33H), 7.21-7.54 (9H, BHA). |
| 6 | 18.98 g | As for batch 3 |

2. Preparation of Compound 1: BHALys[Lys]$_{32}$[α-MIDA-Compound A]$_{32\dagger}$[ε-PEG$_{2100}$]$_{32\ddagger}$ Note: 32† relates to the theoretical number of α-amino groups on the dendrimer available for substitution with MIDA-Compound A. The actual mean number of MIDA-Compound A groups attached to BHALys[Lys]$_{32}$ was determined experimentally by $^{19}$F NMR (see Example 2). 32‡ relates to the theoretical number of ε-amino groups on the dendrimer available for substitution with PEG$_{2100}$. The actual mean number of PEG$_{2100}$ groups attached to BHALys[Lys]$_{32}$ was determined experimentally by $^1$H NMR.

(a) Preparation of MIDA-Compound A

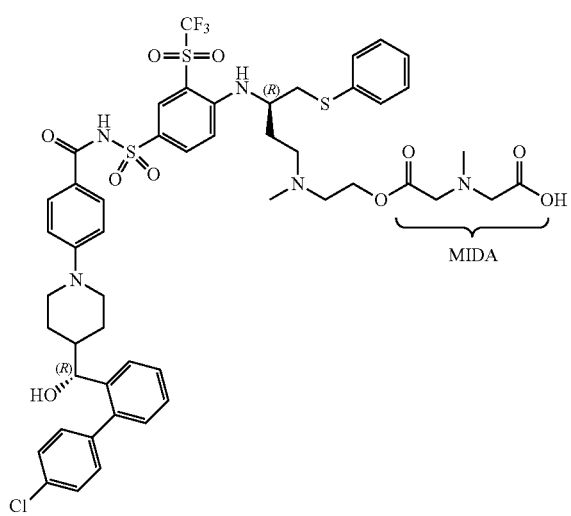

To a magnetically stirred suspension of Compound A (200 mg, 0.21 mmol) in DCM (5 mL) at room temperature was added and DIPEA (24 μL, 0.14 mmol), NMM (72 μL, 0.66 mmol) and 4-methylmorpholine-2,6-dione (33 mg, 0.26 mmol). The suspension dissolved quickly and the mixture was left to stir at room temperature overnight. Additional 4-methylmorpholine-2,6-dione was added over the following 24 hours until the reaction was judged >80% complete by HPLC. The volatiles were then removed in vacuo and the residue purified by preparative HPLC (BEH 300 Waters XBridge C18, 5 μM, 30×150 mm, 50-70% ACN/water (5-40 min), 0.1% TFA, RT=23 min) providing 190 mg (84%) of product as a white solid. LCMS (C18, gradient: 50-60% ACN/H$_2$O (1-10 min), 60% ACN (10-11 min), 60-50% ACN (11-13 min), 50% ACN (13-15 min), 0.1% formic acid, 0.4 mL/min, Rf (min)=2.55. ESI (+ve) observed [M+H]$^+$=1074. Calculated for C$_{50}$H$_{55}$ClF$_3$N$_5$O$_{10}$S$_3$=1073.28 Da. $^1$H-NMR (300 MHz, CD$_3$OD) δ (ppm): 0.86-1.07 (m, 1H), 1.08-1.37 (m, 2H), 1.72-1.88 (m, 1H), 1.96-2.09 (m, 1H), 2.10-2.24 (m, 1H), 2.24-2.38 (m, 1H), 2.66 (t, J=12.3 Hz, 1H), 2.79 (t, J=12.6 Hz, 1H), 2.92 (s, 3H), 3.00 (s, 3H), 3.14-3.28 (m, 2H), 3.33-3.43 (m, 2H), 3.47-3.57 (m, 2H), 3.72 (d, J=12.0 Hz, 1H), 3.89 (d, J=12.6 Hz, 1H), 4.03-4.15 (m, 1H), 4.06 (s, 2H), 4.19 (s, 2H), 4.43 (d, J=8.1 Hz, 1H), 4.54-4.64 (m, 2H), 6.88 (d, J=9.0 Hz, 2H), 6.93 (d, J=9.6 Hz, 1H), 7.01 (d, J=9.0 Hz, 1H), 7.09-7.25 (m, 4H), 7.26-7.47 (m, 8H), 7.61 (d, J=8.1 Hz, 1H), 7.68 (d, J=9.0 Hz, 2H), 8.07 (dd, J=9.3, 2.1 Hz, 1H), 8.31 (d, J=2.1 Hz, 1H).

Alternative Method of Preparation

Compound A (28.00 g, 2.96×10$^{-2}$ mol) and 4-methylmorpholine-2,6-dione (7.24 g, 5.33×10-2 mol., 1.80 equiv.) were charged into a 3-neck reaction vessel with an internal temperature probe and pressure equalizing dropping funnel, under an atmosphere of N$_2$. DCM (250 mL, 9 vol.) was introduced, and the ensuing suspension was cooled to 0° C. TEA (6.25 mL, 4.44×10$^{-2}$ mol., 1.5 equiv.) in DCM (50 mL, 1.8 vol.) was added drop-wise over a 10 minute period whilst maintaining the temperature at 0° C. Reaction in process controls were taken hourly. The reaction was deemed complete when Compound A is <10% by peak area (typically 4.5 h after the end of addition). The reaction mixture is diluted with DCM (1.40 L, 50 vol.) and washed twice with 1.6 M aq. Na$_2$CO$_3$ (1.60 L, 50 vol.). The organic layer was dried over MgSO$_4$ (90 g, 5% w/v), filtered through a sintered glass funnel and washed with DCM (100 mL, 5 vol.) affording an off-white solid after concentration in vacuo (0.2 bar, 30° C.) (33.07 g, 95% yield, 90.6% by HPLC).

(b) Preparation of BHALys[Lys]$_{32}$[α-MIDA-Compound A]$_{32\dagger}$[ε-PEG2100]$_{32\ddagger}$ Small Scale Method of Preparation

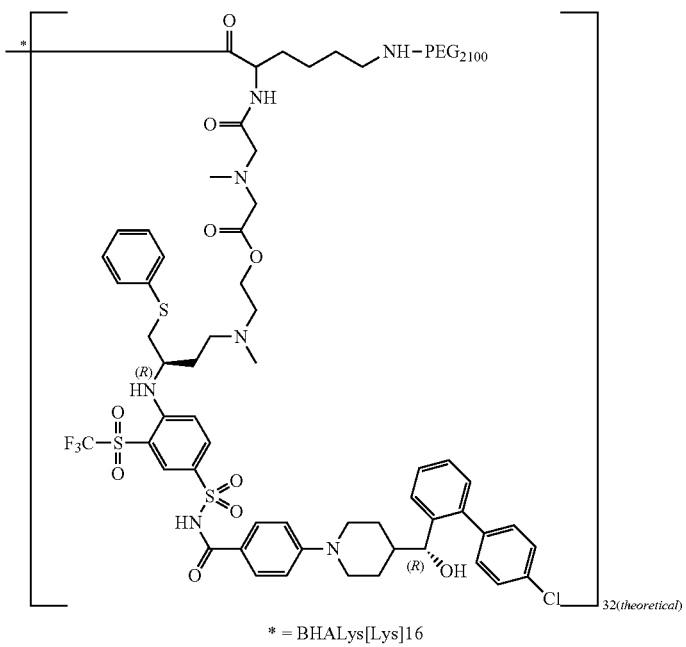

\* = BHALys[Lys]16

To a magnetically stirred mixture of Compound A-MIDA (730 mg, 0.68 mmol) and PyBOP (353 mg, 0.68 mmol) in DMF (10 mL) at room temperature was added a mixture of BHALys[Lys]$_{32}$[α-NH$_2$TFA]$_{32}$[ε-PEG$_{2100}$]$_{31}$ (934 mg, 12.1 μmol, Batch 5 of Example 4) and NMM (255 μL, 2.32 mmol), also in DMF (10 mL). After 16 hours at room temperature the volatiles were removed and the residue purified by size exclusion chromatography (sephadex, LH20, ACN). The appropriate fractions, as judged by HPLC, were combined and concentrated. The residue was then taken up in water, filtered (0.22 μm) and lyophilised, providing 1.19 g (92%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.80. 1H-NMR (300 MHz, CD$_3$OD) δ (ppm): 0.45-1.92 (m, 565H), 2.08-2.78 (m, 228H), 2.79-3.00 (m, 96H), 3.01-3.28 (m, 180H), 3.35 (s, 180H), 3.46-4.20 (m, 6164H), 4.20-4.68 (m, 139H), 6.40-8.52 (m, 680H).

Alternative (Large Scale) Method of Preparation

DMF (225 mL, 16.5 vol.) was added to BHALys[Lys]$_{32}$ [α-NH$_2$TFA]$_{32}$[ε-PEG$_{2100}$]$_{29}$ (13.49 g, 1.72×10$^{-4}$ mol, Batch 6 of Example 4) and Compound A-MIDA (8.50 g, 6.87×10$^{-3}$ mol., 40.2 equiv.) under an atmosphere of N$_2$. NMM (3.60 mL, 3.30×10-2 mol, 192 equiv.) was introduced, and the reaction mixture was warmed to 30-35° C. to aid dissolution (approximately 5 minutes). The mixture was then cooled back to 20° C., and PyBOP (4.13 g, 7.56×10$^{-3}$ mol, 44 equiv.) was introduced in two equal portions. In process control monitoring revealed reaction completion after 2 h. The reaction mixture was diluted with ACN (225 mL, 16.5 volumes), filtered through a sinter funnel and subjected to 16 (constant) diavolumes (200 mL, ACN) of ultrafiltration (Merck Millipore Pellicon 3, 0.11 m2 cassette, 10 kDa), maintaining a transmembrane pressure (TMP) of 25 PSI and 44 L/m2/hour (LMH). Concentration under reduced pressure (40° C., 0.2 bar; 60 minutes), and drying at ambient temperature for a further 16 h afforded 23.5 g of purified material as a light orange syrup. The syrup was dissolved in THF (235 mL, 10 volumes) at 35-40° C. (10 minutes) and filtered through a 47 mm, 0.45-micron PTFE membrane (Merck-Millippore Omnipore). The filtrate was concentrated to half its original volume (100 mL, 4.3 volumes), and charged to a pressure equalizing dropping funnel upon returning to ambient temperature.

MTBE (400 mL, 19.5 volumes) was charged to a 3-neck RBF fitted with an internal temperature probe, and cooled to 0° C. with the aid of an external ice bath under an atmosphere of N$_2$. Upon reaching 0° C., addition of dendrimer commenced lasting 15 minutes (max. internal temperature 5° C.), whilst stirring continued for 45 minutes (at 0-5° C.) to allow ripening of the precipitate. Transferring the ensuing mixture to a Buchner vacuum filter (160 mm diameter) under N$_2$, afforded the first wet cake within 15 minutes. The filter cake was washed twice with 5 vol. MTBE (100 mL per wash) and pulled to dryness (under N$_2$) lasting a total of 15 minutes. The filter cake was transferred to a vacuum oven where drying took place at (25° C., 0.2 bar) until constant mass was achieved (48 h), affording free flowing white powder in 18.98 g (102% yield). HPLC (C8 Phenomenix Aeris, 2.1×100 mm, gradient: 5% ACN (0-1 min), 5-45% ACN/H$_2$O) (1-2 min), 45-60% ACN (2-8 min), 60% ACN (8-10 min), 60-90% ACN (10-10.1 min), 90% ACN (10.1-12 min), 90-5% ACN (12-15 min), 5% ACN (15-20 min), 272 nm, 10 mM ammonium formate) Rf (min)=14.94. $^1$H-NMR (300 MHz, CD$_3$OD) δ (ppm): 0.31-2.84 (m, 953H), 2.86-3.27 (m, 211H), 3.35 (s, 109H), 3.37-4.23 (m, 5734H), 4.24-4.64 (m, 95H), 6.26-8.41 (m, 632H). $^{19}$F-NMR (300 MHz, DMSO-d$_6$) δ: −107.1 ppm (3.64 mg, FBA, set integration to 100), −79.1 ppm (31.2 mg dendrimer, 108.82). This provides 8.91 mg Compound A (or 28.6% loading).

3. Preparation of Compound 2: BHALys[Lys]$_{32}$[α-TDA-Compound A]$_{32†}$[ε-PEG$_{2100, 2200}$]$_{32‡}$ Note: 32† relates to the theoretical number of α-amino groups on the dendrimer available for substitution with TDA-Compound A. The actual mean number of TDA-Compound A groups attached to BHALys[Lys]$_{32}$ was determined experimentally by $^1$H NMR (see Example 2). 32‡ relates to the theoretical number of ε-amino groups on the dendrimer available for substitution with PEG$_{2100, 2200}$. The actual mean number of PEG$_{2100, 2200}$ groups attached to the BHALys[Lys]$_{32}$ was determined experimentally by $^1$H NMR.

(a) Preparation of TDA-Compound A

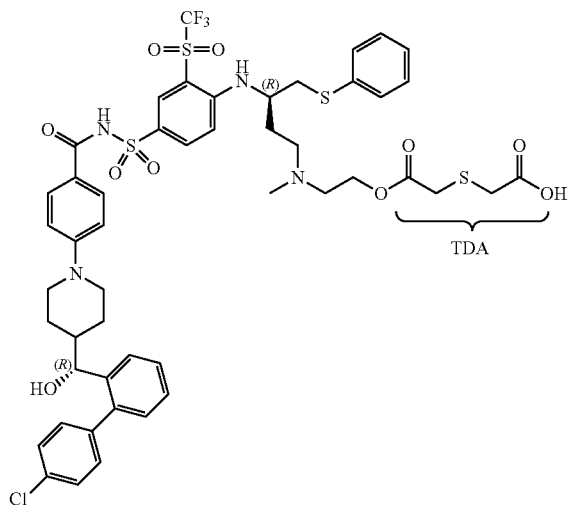

To a magnetically stirred suspension of Compound A (70 mg, 74.1 μmol) in DCM (5 mL) at room temperature was added thiodiglycolic anhydride (TDA, 10 mg, 74.1 μmol) and DIPEA (33 μL, 185 μmol). The suspension dissolved quickly and the mixture was left to stir at room temperature overnight. Additional thiodiglycolic anhydride was added over the following 24 hours until the reaction was judged >80% complete by HPLC. The volatiles were then removed in vacuo and the residue purified by preparative HPLC (BEH 300 Waters XBridge C18, 5 μM, 30×150 mm, 60-80% ACN/water (5-40 min), 0.1% TFA, RT=22 min) providing 63 mg (70%) of product as a white solid. LCMS (C18, gradient: 50-60% ACN/H$_2$O (1-10 min), 60% ACN (10-11 min), 60-50% ACN (11-13 min), 50% ACN (13-15 min), 0.1% formic acid, 0.4 mL/min, Rf (min)=7.33. ESI (+ve) observed [M+H]+=1077. Calculated for C$_{49}$H$_{52}$ClF$_3$N$_4$O$_{10}$S$_4$=1076.22 Da. $^1$H-NMR (300 MHz, CD$_3$OD) δ (ppm): 0.87-1.04 (m, 1H), 1.08-1.36 (m, 3H), 1.71-1.90 (m, 1H), 1.96-2.40 (m, 3H), 2.64 (t, J=12.0 Hz, 1H), 2.77 (t, J=12.6 Hz, 1H), 2.94 (s, 3H), 3.18-3.30 (m, 2H), 3.35 (s, 2H), 3.40 (s, 2H), 3.46-3.55 (m, 2H), 3.73 (d, J=13.5 Hz, 1H), 3.90 (d, J=12.9 Hz, 1H), 4.02-4.15 (m, 1H), 4.40-4.48 (m, 3H), 6.86 (d, J=9.3 Hz, 2H), 6.92 (d, J=9.6 Hz, 1H), 7.02 (d, J=9.0 Hz, 1H), 7.08-7.46 (m, 13H), 7.61 (d, J=7.8 Hz, 1H), 7.67 (d, J=9.0 Hz, 2H), 8.08 (dd, J=9.3, 2.1 Hz, 1H), 8.31 (d, J=2.1 Hz, 1H).

Alternative Method of Preparation

Compound A (25.50 g, 2.70×10$^{-2}$ mol) and TDA (4.81 g, 3.64×10$^{-2}$ mol, 1.35 equiv.) were charged into a 3-neck reaction vessel fitted with an internal temperature probe and pressure equalizing dropping funnel under an atmosphere of N$_2$. DCM (255 mL, 10 vol.) was introduced, and the ensuing suspension was cooled to −10° C. 0.29M TEA in DCM, (100 mL, 3.77×10$^{-2}$ mol, 1.4 equiv.) was introduced over a 40-minute period whilst maintaining the temperature at −10° C. Reaction in-process controls (IPC's) were taken hourly. The reaction was deemed complete when Compound A was <10% area by HPLC (typically 4.5 h after the end of addition). The reaction mixture was diluted with DCM (1.66 L, 65 vol.) and washed three times with aq. phosphate buffered saline (PBS) solution (1.02 L, 40 vol.). The combined organic extracts were dried over MgSO$_4$ (100 g, 5% w/v), affording a pale-yellow solid after concentration in vacuo (0.2 bar, 25° C.) overnight (typically 24.5 g, 85% yield, 86.83% by HPLC).

(b) Preparation of BHALys[Lys]$_{32}$[α-TDA-Compound A]$_{32†}$[ε-PEG$_{2100, 2200}$]$_{32‡}$ Small Scale Method of Preparation

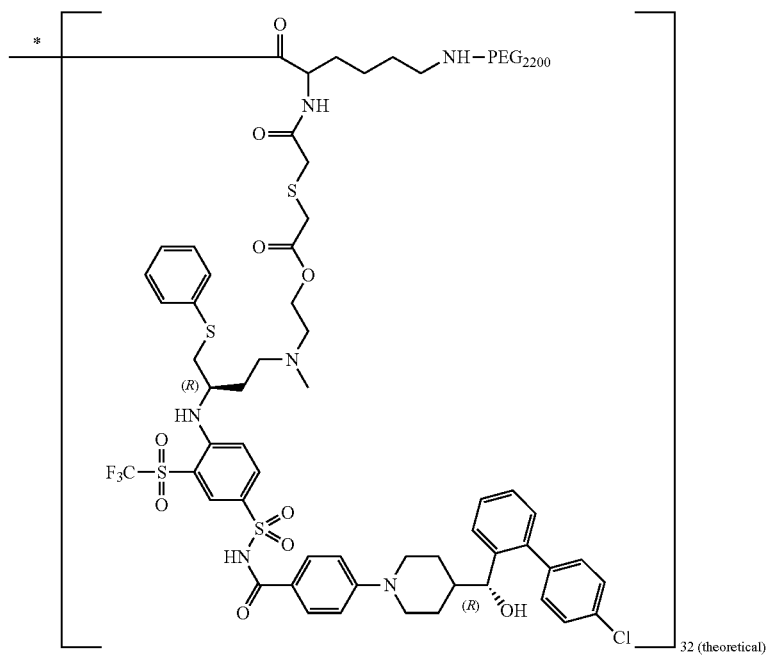

* = BHALys[Lys]16

To a magnetically stirred mixture of Compound A-TDA (62 mg, 58 μmol) and PyBOP (30 mg, 58 μmol) in DMF (1 mL) at room temperature was added a mixture of BHALys [Lys]$_{32}$[α-NH$_2$TFA]$_{32}$[ε-PEG$_{2200}$]$_{29}$ (97 mg, 1.28 μmol, Batch 2 of Example 4) and NMM (27 μL, 0.24 mmol), also in DMF (2 mL). After 16 hours at room temperature the volatiles were removed and the residue purified by size exclusion chromatography (sephadex, LH20, MeOH). The appropriate fractions, as judged by HPLC, were combined and concentrated. The residue was then taken up in water, filtered (0.22 μm) and lyophilized, providing 98 mg (72%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.24. $^1$H-NMR (300 MHz, CD$_3$OD) δ (ppm): 0.62-2.33 (m, 589H), 2.37-2.69 (m, 87H), 2.69-2.92 (m, 98H), 2.94-3.27 (m, 202H), 3.35 (s, 113H), 3.37-4.10 (m, 5781H), 4.10-4.70 (m, 154H), 6.50-8.45 (m, 661H).
Alternative (Large Scale) Method of Preparation The two batches (Batches A and B) were individually taken up in THF (4.7 vol.) and warmed to 35-40° C. until dissolution was complete (10 mins.). To a separate 3-neck round bottom vessel, fitted with an internal thermometer, pressure equalizing dropping funnel and magnetic stirrer was added MTBE (1.8 L, 19.5 vol.). The solvent was then cooled to 0° C. with the aid of an external ice bath. The combined THF solutions of batches A and B were charged to the dropping funnel upon reaching ambient temperature, and introduced drop-wise to the stirred solution of MTBE whilst maintaining the temperature at 0° C. At the first sight of cloudiness, the reaction was seeded with solid BHALys [Lys]$_{32}$[α-TDA-Compound A]$_{27}$[ε-PEG$_{2200}$]$_{29}$ (0.95 g, 1% w/w relative to input batches A and B) and addition resumed, lasting 30 minutes. Crystallization was allowed to ripen for 60 minutes, before being transferred to a Buchner vacuum filter (160 mm diameter) under N$_2$ (lasting 15 mins.). The filter cake was washed twice with 5 vol. MTBE (300 mL per

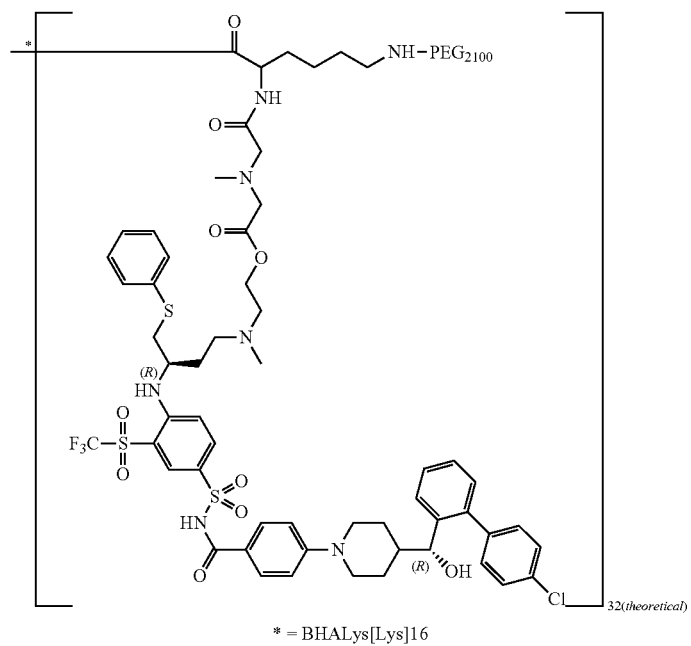

* = BHALys[Lys]16

DMF (495 mL, 16.5 vol.) was added to BHALys[Lys]$_{32}$ [α-NH$_2$TFA]$_{32}$[ε-PEG$_{2100}$]$_{29}$, (30.6 g, 3.82×10$^{-4}$ mol, Batch 3 of Example 4) and Compound A-TDA (19.01 g, 1.53×10$^{-2}$ mol, 40 equiv.) under an atmosphere of N$_2$. NMM (8.06 mL, 7.33×10$^{-2}$ mol, 192 equiv.) was introduced, and the reaction was warmed to 30° C. to aid dissolution (approximately 10 mins). The mixture was then cooled back to 20° C. and PyBOP (9.20 g, 1.68×10-2 mol., 44 equiv.) was introduced in two equal portions. In process control monitoring revealed reaction completion after 2 h. The reaction mixture was diluted with ACN (495 mL, 16.5 vol.), filtered through a sinter funnel and subjected to 10 constant diavolumes (600 mL, ACN) of ultrafiltration (Merck Millipore Pellicon 3, 2×0.11 m2 cassette), maintaining a transmembrane pressure (TMP) of 18 PSI and 48 L/m2/hour (LMH). Concentration under reduced pressure (45° C., 0.2 bar; for 30 mins.), and drying at ambient for a further 16 h afforded 45.7 g of Purified product (Batch A) as a dark yellow syrup. This process was repeated to produce another 46.8 g of material (Batch B).

wash) and pulled to dryness (under N$_2$) lasting a total of 30 minutes. The filter cake was transferred to a vacuum oven where drying took place at 40° C., 0.2 bar until constant mass was achieved (24 h), affording free flowing white powder in 74.8 g (105% yield). HPLC (C8 Phenomenix Aeris, 2.1×100 mm, gradient: 5% ACN (0-1 min), 5-45% ACN/H$_2$O) (1-2 min), 45-60% ACN (2-8 min), 60% ACN (8-10 min), 60-90% ACN (10-10.1 min), 90% ACN (10.1-12 min), 90-5% ACN (12-15 min), 5% ACN (15-20 min), 272 nm, 10 mM ammonium formate) Rf (min)=14.92. $^1$H-NMR (300 MHz, CD$_3$OD) δ (ppm): 0.40-2.30 (m, 589H), 2.31-2.79 (m, 154H), 2.81-3.29 (m, 263H), 3.35 (s, 116H), 3.36-4.10 (m, 5924H), 4.13-4.62 (m, 151H), 6.28-8.52 (m, 622H). 19F-NMR (300 MHz, DMSO-d6) δ: −106.9 ppm (3.81 mg, FBA, set integration to 100), −79.0 ppm (21.4 mg dendrimer, 62.80). This provides 5.36 mg Compound A (or 25.1% loading).

Example 2: Compound a Drug Loading of Dendrimers

The drug loading of Compound A in the dendrimers prepared above were determined by NMR. % Compound A loading by $^1$H NMR: Compound A loading was estimated via integration of the aromatic region (6.5-8.5 ppm), which was representative of Compound A, compared to the PEG region (3.4-4.2 ppm) which is representative of the dendrimer scaffold. % Compound A loading by $^{19}$F NMR: Compound A loadings were calculated by performing a $^{19}$F NMR of the conjugate using an internal standard (4-Fluorobenzoic acid, FBA).

An experiment was typically performed by accurately weighing out a known mass of dendrimer and FBA into a single vial. This was then taken up in DMSO, sonicated (2 min) then analyzed by NMR (100 scans, 30 s delay time). The FBA and dendrimer peaks was then be integrated and the % Compound A calculated using molar ratios (3:1 mole ratio of Compound (3F) to FBA (1F).

TABLE 3

Percent Loading of Compound A on Lys Dendrimer

| Compound | Scale | Compound A loading (%) | MW* (kDa) | No. of Compound A per dendrimer |
|---|---|---|---|---|
| 1 | Small Scale (1.19 g) | 23.6 ($^{19}$F NMR) | 99.7 | 25 |
|  | Large Scale (18.98 g) | 28.6 ($^{19}$F NMR) | 101.6 | 31 |
| 2 | Small Scale (98 mg) | 28.6 ($^1$H NMR) | 106.0 | 32 |
|  | Large Scale (74.8 g) | 25.1 ($^{19}$F NMR) | 96.2 | 27 |

*The total molecular weight can be estimated using the estimated MW of the dendrimer scaffold, the MW Compound
A-linker and the % Compound A loading from NMR. i.e. for
Example: MW = MW dendrimer scaffold − 32 (MW TFA)/(100 − Compound A loading % ((Mr
Compound A-linker − water)/Mr Compound A))/100

$$= \frac{75700 - 3648}{(100 - 28.2((1058 - 18)/945))/100}$$

$$= \frac{72052}{(100 - 28.2(1.10))/100}$$

$$= \frac{72052}{0.6898}$$

$$\approx 104.5 \; kDa$$

Example 4: Rat and Mouse Efficacy Studies

The formulations used in the efficacy studies were prepared as follows:

Preparation of Compounds 1 and 2 PBS formulations for dosing RS4:11 efficacy study: The appropriate amounts of Compound 1 and 2 were weighed into a volumetric flask. 10 mL Dulbecc's Phosphate Buffered Saline (PBS) was added and formulations were then stirred until the compound dissolved entirely.

Formulations of Compound 1 for SuDHL-4 efficacy study: Compound 1 was formulated in a pH 5 citrate/phosphate buffer diluted 1:10 with 5% glucose and containing 1% w/v Kolliphor HS-15, at concentrations up to 105 mg/mL of Compound 1 (equivalent to up to 30 mg/mL of Compound A concentration).

100 ml McIlvane citrate/phosphate buffer pH 5 was prepared. 1.02 g citric acid monohydrate and 3.69 g sodium phosphate dibasic dodecahydrate were weighed into a vial and 95 mL of water for injection was added. The vehicle was stirred (or sonicated) to dissolve. The pH was then measured and adjusted to pH 5 with 0.1M HCl or NaOH, as required. The vehicle was made to volume (100 mL) with Water for Injection.

This McIlvane buffer was used to prepare the diluted buffer vehicle (pH 5 citrate/phosphate buffer diluted 1:10 with 5% glucose and containing 1% w/v Kolliphor HS-15). The required amount of McIlvanes citrate/phosphate buffer, equivalent to 10% of the total target volume to be prepared, was added to a suitable container. Commercially available 5% glucose solution was added to approximately 90% of the target volume. Kolliphor HS-15 equivalent to 1% w/v was added and the vehicle stirred to dissolve the Kolliphor HS-15. pH was measured and adjusted to pH 5.0±0.05 with 0.1M HCl or NaOH (if required). The vehicle was then made to volume with 5% glucose. It was filter sterilized using a 0.22 μm pore size syringe filter, if necessary.

To prepare the formulation of Compound 1 for the higher dose (10 mg/mL Compound A or Compound 1 equivalent of 37 mg/mL), 370 mg of Example 9, equivalent to 100 mg Compound A, was transferred into a suitable container with a magnetic stirrer. Whilst the magnetic stirrer was in operation, diluted buffer vehicle (pH 4 citrate/phosphate buffer that has been diluted 1:10 with 5% glucose containing 1% w/v Kolliphor HS-15) was added to 95% of the target volume (9.5 mL). Continued stirring to aid dissolution, avoiding generation of excessive frothing, until a clear solution was formed. The formulation was then made to volume (0.5 mL) with diluted buffer vehicle and the pH checked. The formulation was assessed visually to rule out the presence of particles. 2 and 6 mg/ml were prepared from the higher concentration.

Formulations of Compound 1 were prepared at room temperature and dosed within 5 minutes of preparation.

Formulations of Compound 2 for dosing in SuDHL-4 efficacy study: Compound 2 was formulated in a pH 4 citrate/phosphate buffer diluted 1:10 with 5% Glucose and containing 1% w/v Kolliphor HS-15, at concentrations up to 121 mg/mL of Compound 2 (equivalent of up to 30 mg/mL of Compound A concentration).

100 ml McIlvane citrate/phosphate buffer pH4 was prepared. 1.29 g Citric acid monohydrate and 2.76 g sodium phosphate dibasic dodecahydrate were weighed into a vial and 95 mL of water for injection was added. The vehicle was stirred (or sonicated) to dissolve. The pH was then measured and adjusted to pH 4 with 0.1M HCl or NaOH, as required. The vehicle was made to volume (100 mL) with Water for Injection.

This McIlvane buffer was used to prepare the diluted buffer vehicle (pH 4 citrate/phosphate buffer diluted 1:10 with 5% glucose and containing 1% w/v Kolliphor HS-15). The required amount of McIlvane citrate/phosphate buffer, equivalent to 10% of the total target volume to be prepared, was added to a suitable container. Commercially available 5% glucose solution was added to approximately 90% of the target volume. Kolliphor HS-15 equivalent to 1% w/v was added and the vehicle stirred to dissolve the Kolliphor HS-15. pH was measured and adjusted to pH 4.0±0.05 with 0.1M HCl or NaOH (if required). The vehicle was then made to volume with 5% glucose. It was filter sterilized using a 0.22 μm pore size syringe filter, if necessary.

To prepare the formulation of Compound 2 for the higher dose (10 mg/mL Compound A or Compound 2 equivalent of 39 mg/mL), 390 mg of Compound 2, equivalent to 100 mg Compound A, was transferred into a suitable container with a magnetic stirrer. Whilst the magnetic stirrer was in operation, diluted buffer vehicle (pH 4 citrate/phosphate buffer that has been diluted 1:10 with 5% glucose containing 1% w/v Kolliphor HS-15) was added to 95% of the target volume (9.5 mL). Stirring of the formulation was continued to aid dissolution, avoiding generation of excessive frothing, until a clear solution was formed. The formulation was then made to volume (0.5 mL) with diluted buffer vehicle and the pH checked. The formulation was assessed visually to rule out the presence of particles. 2 and 6 mg/ml were prepared from the higher concentration.

Formulations of Compound 2 were prepared at room temperature and dosed within 5 minutes of preparation.

Formulation of Compound A in 30% w/v HP-β-CD

30% w/v HP-β-CD vehicle was prepared. 3 g HP-β-CD (Roquette Kleptose, parenteral grade) was weighed into a 10 mL volumetric flask and 8 mL WFI added and stirred (or sonicated) to dissolve. Once dissolved the volume was made up to 10 mL with WFI.

The appropriate amount of Compound A was weighed into a 10 mL volumetric flask. 8 mL of 30% w/v HP-β-CD vehicle was then added and the formulation stirred. 1M MSA was added dropwise until the pH was reduced to about 2. The formulation was then stirred until the compound dissolved entirely. The pH was measured and adjusted to pH 4, dropwise using 1M MSA or NaOH. The formulation was then stirred to make sure a clear solution (with possible haze) was obtained. The volume was then made up to 10 mL with 30% w/v HP-β-CD vehicle and stirred. The final pH was measured and recorded and the formulation filtered through a 0.22 μM filter prior to administration. Other formulation strengths were prepared by diluting the Compound A in 30% w/v HP-β-CD with an appropriate amount of 30% w/v HP-β-CD vehicle.

Efficacy of Compounds 1 and 2 in RS4:11 Xenograft Model: 5×10$^6$ RS4; 11 cells in a total volume of 100 μL were inoculated subcutaneously at the mouse right flank. When the tumor volume reached approximately ~350 mm$^3$, tumor-bearing mice were randomized into groups of 4 animals and treated with either control Vehicle (PBS) or treatment. FIG. 1 shows that with different release rates, the dendrimers exhibit differing efficacy. Compound 1 at 10 mg/kg Compound A equivalent and Compound 2 at 30 mg/kg Compound A equivalent with single IV dose have shown similar or slightly better activity than the Compound A HP-β-CD 10 mg/kg IV once, (100%, 98% vs. 90% regression, respectively).

Figure 2:
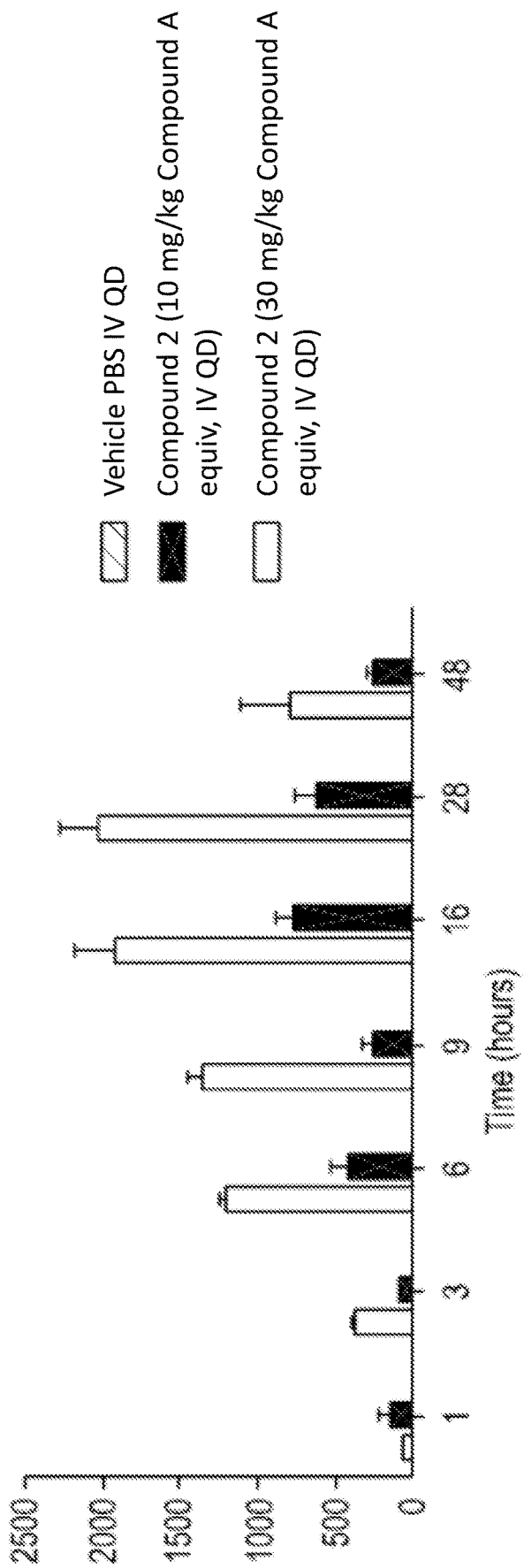
FIG. 2 displays the cell death (apoptosis) at various time points post a single dose of either vehicle (phosphate buffered saline) or Compound 2 in PBS (equivalent to 10 and 30 mg/kg Compound A). Cleaved Caspase 3 (CC3) response was used as a measure of cell death and was determined using the Cell Signaling Pathscan ELISA Kit.

When RS4; 11 tumor volume reached approximately ~400-600 mm$^3$, groups of 3 tumor-bearing mice were treated with a single dose of either vehicle (PBS) or Example 2 I.V at 10 and 30 mg/kg. Tumors were collected at different time-points post-dose and processed for analysis. Results shows that the linker induces comparable apoptotic response as indicated by cleaved Caspase 3, the responses were peaked at 16-28 hr post dose (FIG. 2). Compound 2 at 30 mg/kg Compound A equivalent (117 mg/kg Compound 2) induced the highest CC3 response.

Figure 3:
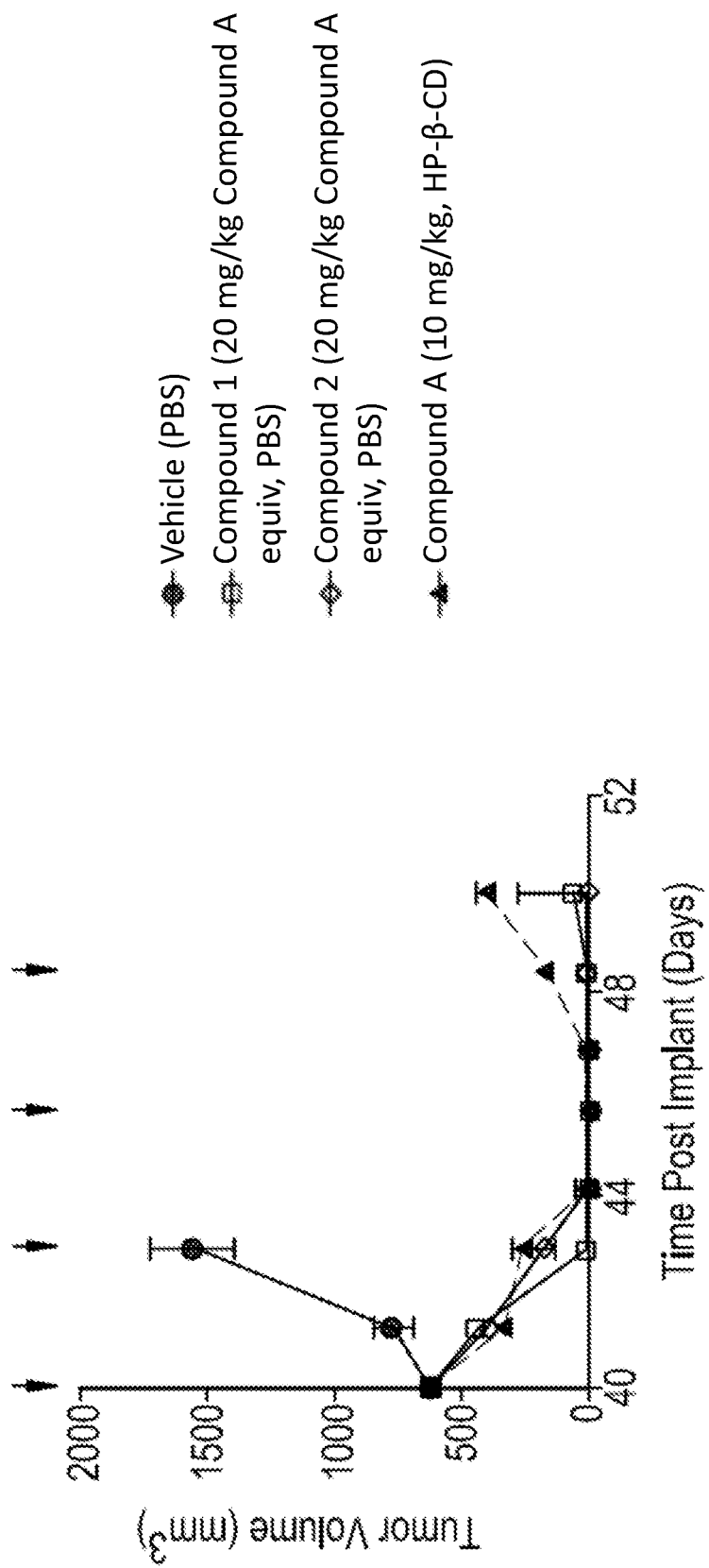
FIG. 3 displays an Acute Lymphoblastic Leukemia (ALL) Xenograft model in SCID mice using human acute lymphoblastic leukemia cells (RS4:11) for the various disclosed dendrimers. The efficacy evaluation of the vehicle (phosphate buffer saline, PBS), a formulation of Compound A in 30% HP-β-CD, Compound 1 in PBS (equivalent to 20 mg/kg Compound A) and Compound 2 in PBS (equivalent to 20 mg/kg Compound A) and is shown.

FIG. 3 shows that Compound 1 and Compound 2 dosed at 20 mg/kg Compound A equivalent (78 and 74 mg/kg of Compound 1 and 2, respectively) were slightly more efficacious than Compound A in the HP-β-CD formulation at 10 mg/kg weekly.

Figure 4:
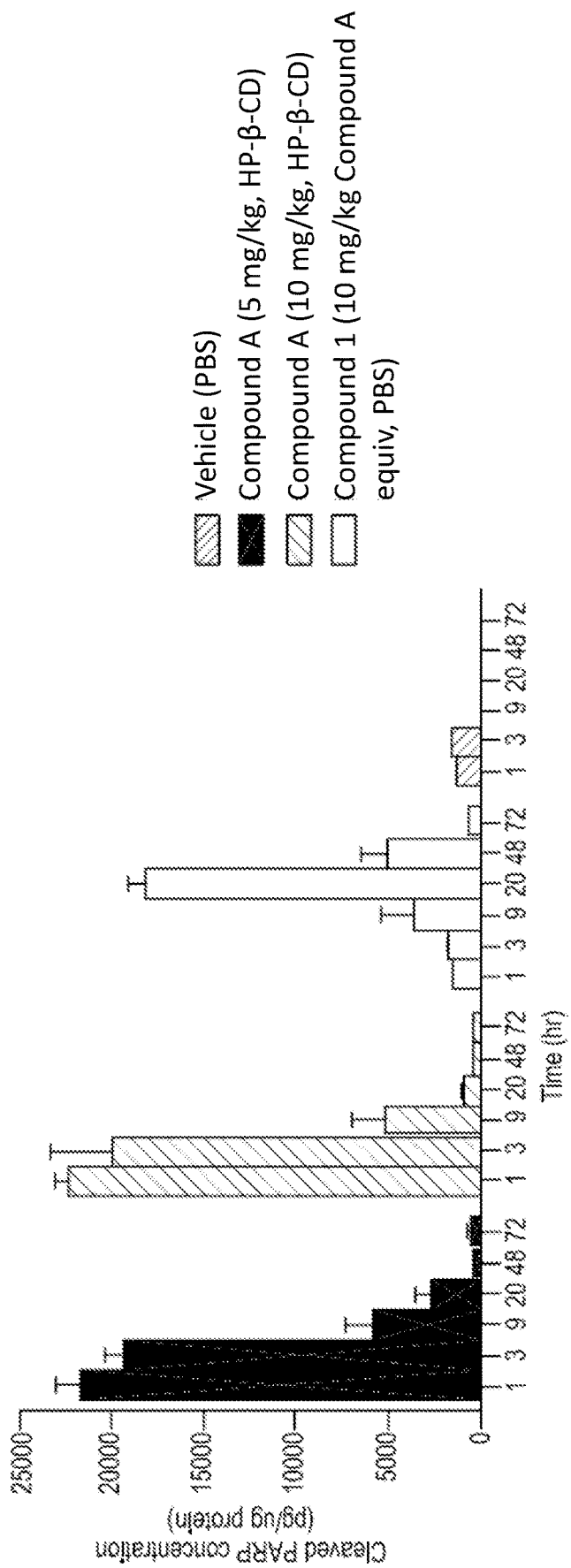
FIG. 4 displays the cell death (apoptosis), at various time points after a single dose of the vehicle (phosphate buffered saline), formulations of Compound A in 30% HP-β-CD at 5 mg/kg and 10 mg/kg and the dendrimer of Compound 1 in PBS at 10 mg/kg Compound A equivalent. Cleaved poly ADP ribose polymerase (PARP) response was used as a measure of cell death.

Additionally, cell death (apoptosis) was measured using cleaved PARP (FIG. 4). Compound A in the HP-β-CD (see Example 2) formulation induced cleaved PARP immediately post treatment 1 and 3 hr, while Compound 1 caused cell death maximum cell death at 20 hr post single dose.

Figure 5:
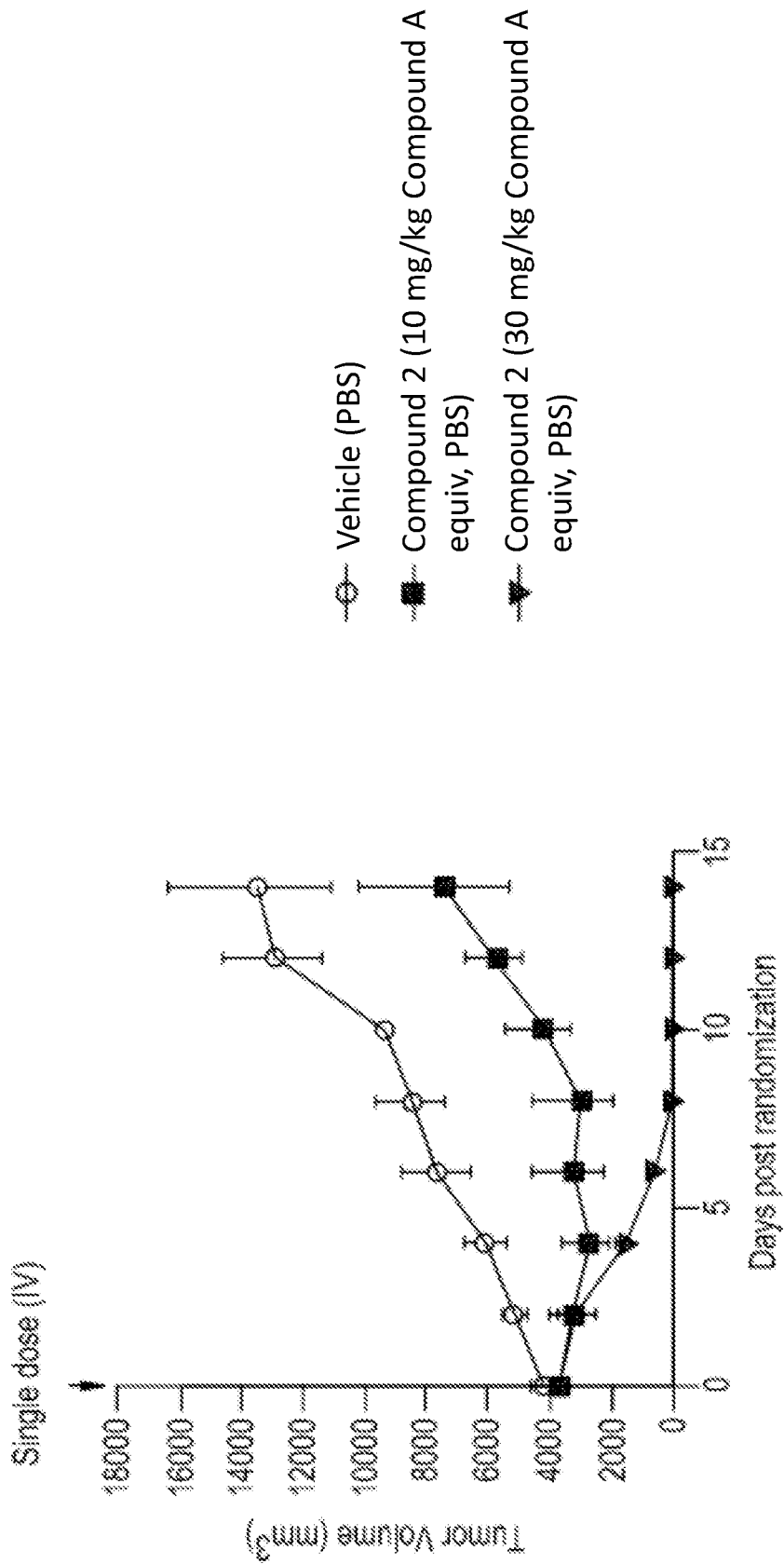
FIG. 5 displays an Acute Lymphoblastic Leukemia (ALL) Xenograft model in Rag2-/- rats using human acute lymphoblastic leukemia cells (RS4:11) for Compound 2 and the vehicle. The efficacy evaluation of the vehicle (phosphate buffer saline, PBS) and Compound 2 in PBS (equivalent to 10 mg/kg and 30 mg/kg Compound A) is shown.
Figure 6:
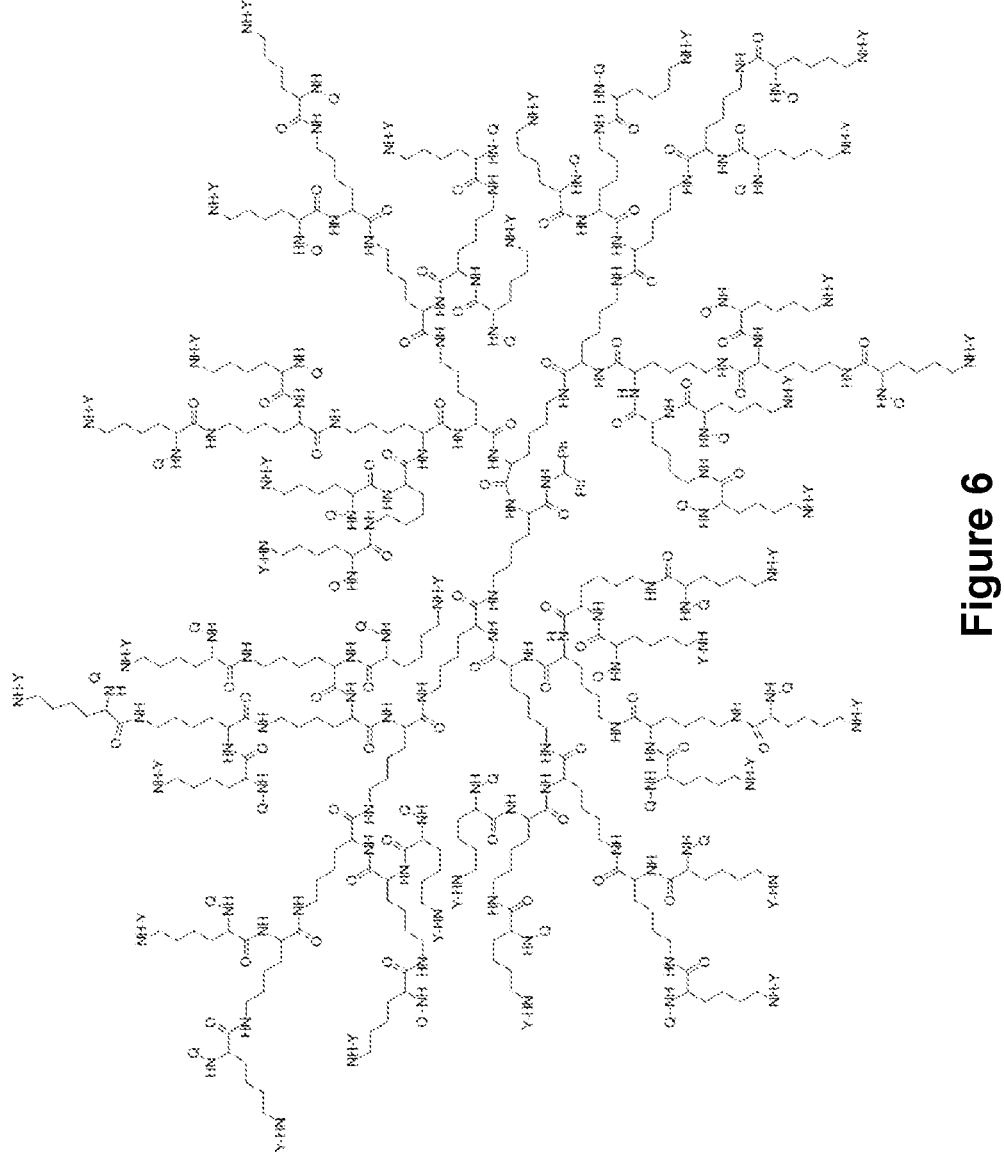
FIG. 6 displays the dendrimer of formula (IV).
Figure 7:
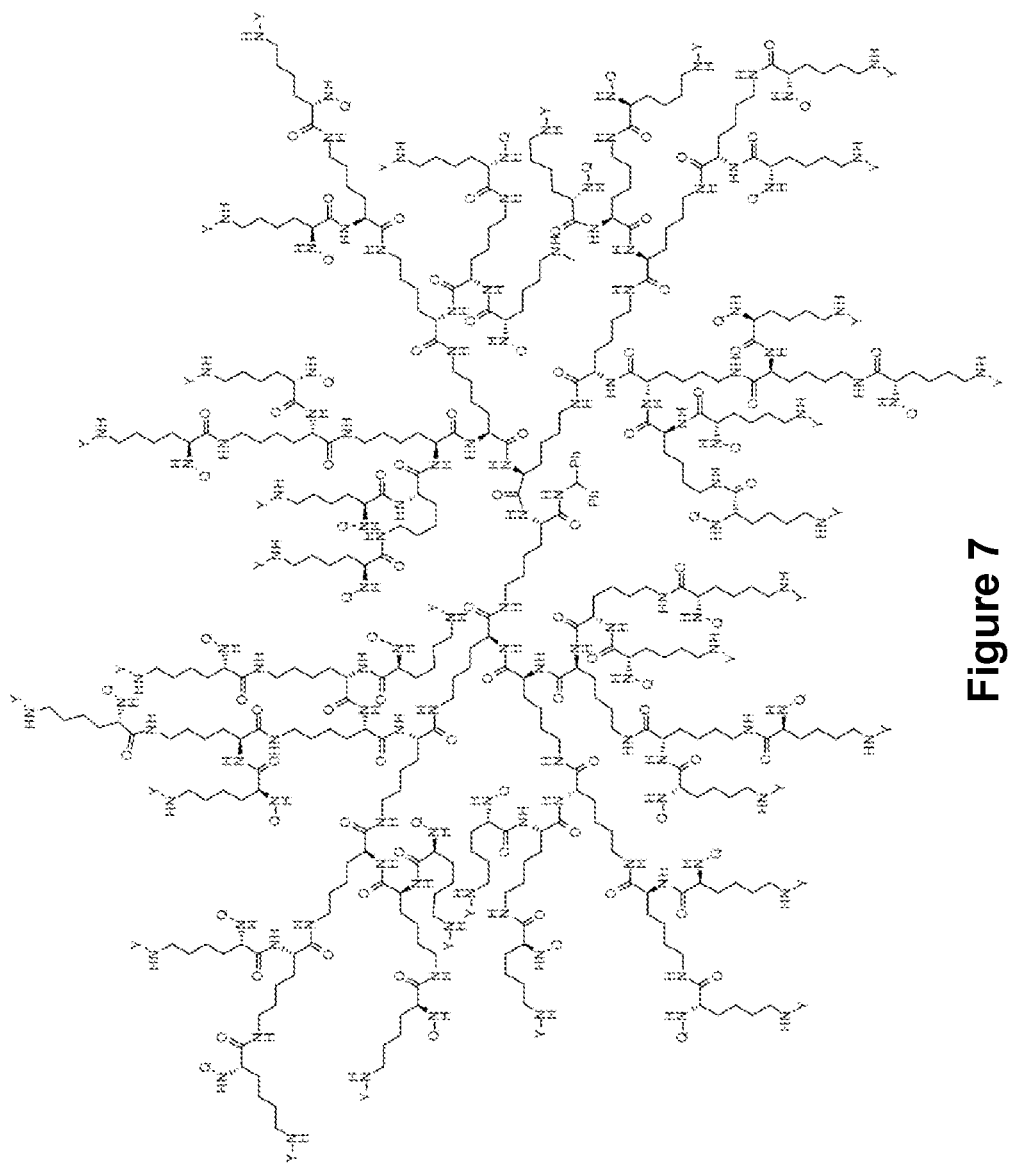
FIG. 7 displays the dendrimer of formula (V).

Efficacy of Compound 2 in RS4:11 xenograft model in Rag2−/− rat: FIG. 5 shows that Compound 2 dosed at 30 mg/kg Compound A equivalent (117 mg/kg Compound 2) causes regression of RS4; 11 tumor. 10 mg/kg Compound A equivalent (39 mg/kg Compound 2) single dose of Compound 2 inhibited tumor growth (stasis). Compounds 1 and 2 enhance inhibition of tumor growth by rituximab in SuDHL-4 Xenograft Model in SCID Mice: The SuDHL-4 xenograft model was used to test the ability of Compounds 1 and 2 to enhance the activity of rituximab in inhibiting tumor growth. When tumors grew to approximately 175-250 mm$^3$, mice were randomized to the following groups:

(1) vehicle control group;
(2) Compound 2 treatment group (50 mg/kg Compound A equivalent, 195 mg/kg Compound 2, i.v. once a week for 5 weeks);
(3) Compound 1 treatment group (50 mg/kg, Compound A equivalent, 185 mg/kg Compound 1, i.v. once a week for 5 weeks;
(4) rituximab group (10 mg/kg i.p. once a week for 5 weeks);
(5) Compound 2 (10 mg/kg Compound A equivalent, 39 mg/kg Compound 2) plus rituximab;
(6) Compound 2 (30 mg/kg Compound A equivalent, 117 mg/kg Compound 2) plus rituximab;
(7) Compound 2 (50 mg/kg Compound A equivalent, 195 mg/kg Compound 2) plus rituximab.

TABLE 4

Summary of inhibition and regression data for Compounds 1 and 2

| Group Number | Treatment | % Inhibition Day (47) | % Regression Day(47) | P-value Day (47) | T − C(Days) |
|---|---|---|---|---|---|
| 1 | Vehicle | | | | |
| 2 | Compound A 5 mg/kg | >100 | 90 | <0.0001 | |
| 3 | Compound 2 10 mg/kg Compound A equivalent (39 mg/kg macromolecule) | >100 | 56 | <0.0001 | |
| 4 | Compound 2 30 mg/kg Compound A equivalent (117 mg/kg macromolecule) | >100 | 100 | <0.0001 | >32 |
| | Compound 1 10 mg/kg Compound A equivalent (37 mg/kg macromolecule) | >100 | 98 | 0.0085 | |

(8) Compound 1 (10 mg/kg Compound A equivalent, 37 mg/kg Compound 1) plus rituximab;
(9) Compound 1 (30 mg/kg Compound A equivalent, 111 mg/kg Compound 1) plus rituximab;
(10) Compound 1 (50 mg/kg Compound A equivalent, 185 mg/kg Compound 1) plus rituximab;

Tumor sizes were measured 2 times a week and calculated as: Tumor Volume=$(A \times B^2)/2$ where A and B are the tumor length and width (in mm), respectively.

Figure 8:
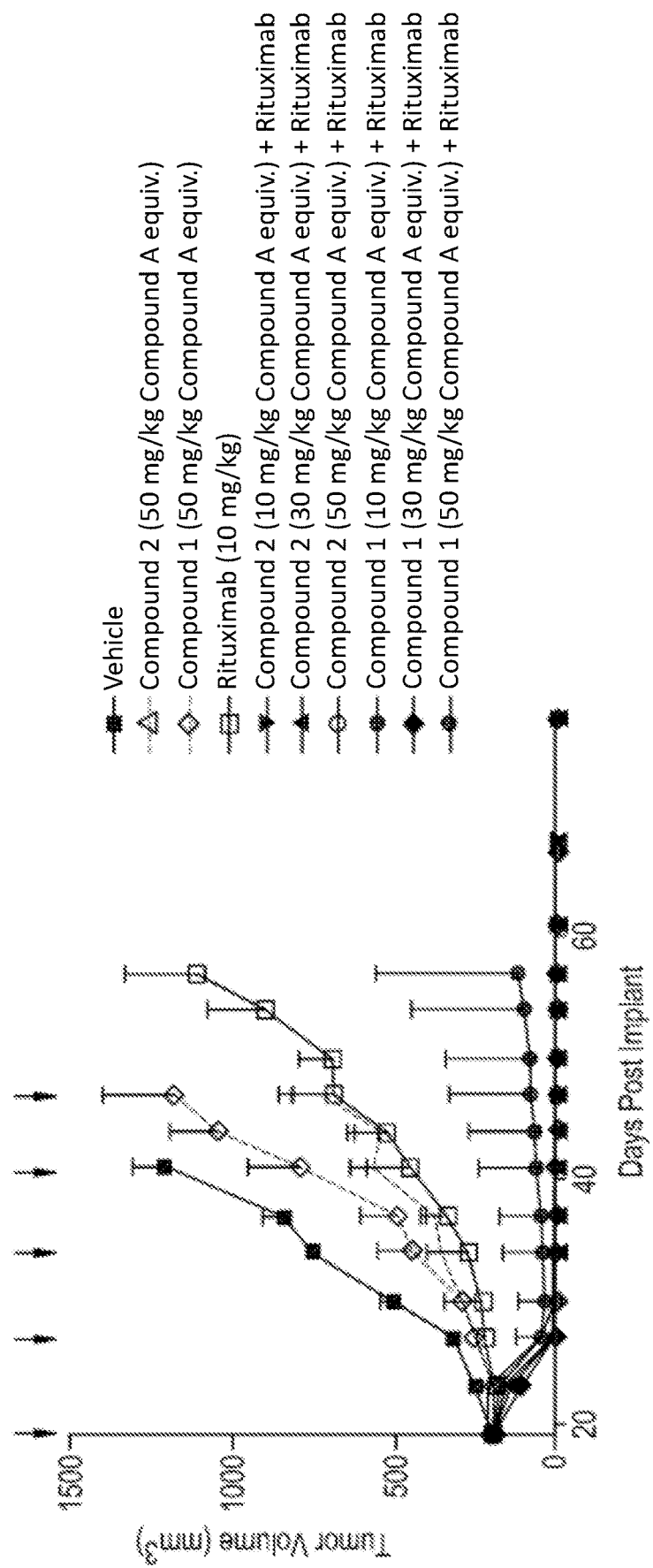
FIG. 8 displays a SuDHL-4 Xenograft Model in SCID mice for the vehicle (phosphate buffer saline, PBS), Compound 2 in PBS (equivalent to 50 mg/kg Compound A), Compound 1 in PBS (equivalent to 50 mg/kg Compound A), rituximab (10 mg/kg), a combination of Compound 2 (10 mg/kg, 30 mg/kg and 50 mg/kg Compound A equivalent) with rituximab (10 mg/kg), and a combination of Compound 1 (10 mg/kg, 30 mg/kg and 50 mg/kg Compound A equivalent) with rituximab (10 mg/kg). See Example 18.

The results are shown in FIG. 8. Compound 1 and 2 at 50 mg/kg Compound A equivalent (185 and 195 mg/kg dendrimer, respectively) significantly inhibited tumor growth as compared to vehicle control with Compound 2 being slightly more efficacious as a monotherapy than Compound 1 at 50 mg/kg Compound A. Table 5 summarizes the tumor growth inhibition (TIC) and tumor growth delay (T-C) values calculated as % Inhibition & % Regression. The calculation is based on the geometric mean of RTV in each group.

On specific day, for each treated group, calculate Inhibition value by formula: Inhibition %=(CG-TG)*100/(CG-1), in which "CG" means the geometric mean of rtv of the control group and "TG" means the Geometric Mean of Relative Tumor Volume (rtv) of the treated group. "CG" should use the corresponding control group of the treated group when calculated. If Inhibition >100%, then it's necessary to calculate the Regression by formula:

Regression=1−TG

The TIC value is 63.5% for 50 mg/kg Compound A equivalent (195 mg/kg Compound 2), 40.44% for 50 mg/kg Compound A equivalent (185 mg/kg Compound 1) and 75.27% for 10 mg/kg rituximab. Thus, Compounds 1 and 2 dosed at 50 mg/kg Compound A equivalent are significantly active in this model. More significantly, a combination of Compounds 1 and 2 at 10, 30, and 50 mg/kg Compound A equivalent with rituximab (10 mg/kg) resulted in tumor regression. Additionally, the combination treatment resulted in complete tumor regression in most animals whereas none were seen with the single drug treatments.

TABLE 5

Summary of efficacy data of Compounds 1 and 2 in combination with rituximab

| | Treatment | Efficacy | | | |
| --- | --- | --- | --- | --- | --- |
| | | % Inhibition (TIC) Day(41) | % Regression Day(41) | P-value Day(41) | T − C(Days) |
| 1 | Vehicle | | | | |
| 2 | Compound 2 (50 mg/kg Compound A equivalent, 195 mg/kg Compound 2) | 63.5 | | 0.0002 | |
| 3 | Compound 1 (50 mg/kg Compound A equivalent, 185 mg/kg Compound 1) | 40.44 | | 0.0420 | |
| 4 | rituximab (10 mg/kg) | 75.27 | | 0.0010 | >16 |
| 5 | rituximab (10 mg/kg) plus Compound 2 (10 mg/kg Compound A equivalent, 39 mg/kg Compound 2) | >100 | 97 | 0.0005 | >37 |
| 6 | rituximab (10 mg/kg) plus Comound 2 (30 mg/kg Compound A equivalent, 117 mg/kg Compound 2) | >100 | 100 | <0.0001 | >37 |
| 7 | rituximab (10 mg/kg) plus Compound 2 (50 mg/kg Compound A equivalent, 195 mg/kg Compound 2) | >100 | 100 | <0.0001 | >37 |
| 8 | rituximab (10 mg/kg) plus Compound 1 (10 mg/kg Compound A equivalent, 37 mg/kg Compound 1) | >100 | 69 | 0.0230 | >37 |

TABLE 5-continued

Summary of efficacy data of Compounds 1 and 2 in combination with rituximab

|   | Treatment | % Inhibition (TIC) Day(41) | % Regression Day(41) | P-value Day(41) | T − C(Days) |
|---|---|---|---|---|---|
| 9 | rituximab (10 mg/kg) plus Compound 1 30 mg/kg Compound A equivalent, 111 mg/kg Compound 1) | >100 | 100 | <0.0001 | >37 |
| 10 | rituximab (10 mg/kg) plus Compound 1 (50 mg/kg Compound A equivalent, 185 mg/kg Compound 1) | >100 | 100 | <0.0001 | >37 |

Figure 9:
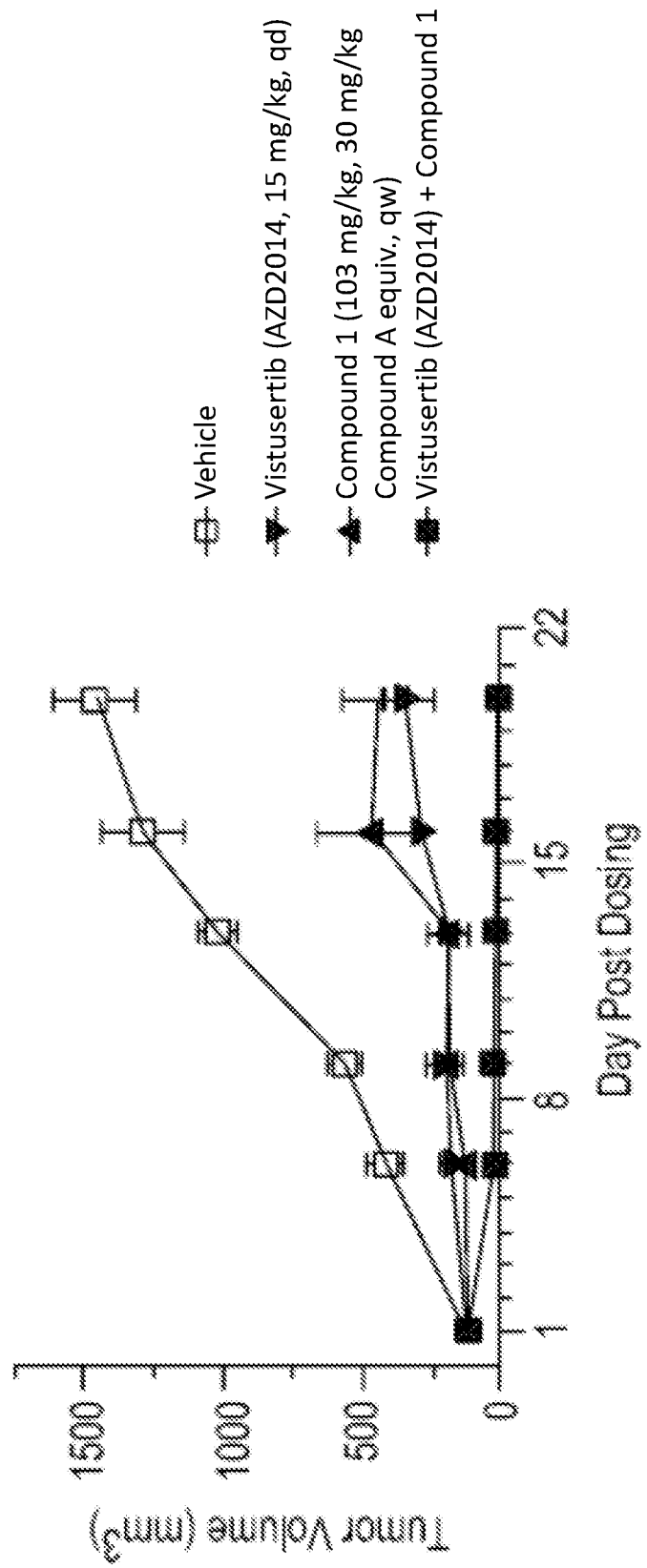
FIG. 9 illustrates the in vivo anti-tumor activity in a human small cell lung cancer tumor model exhibited by Compound 1 in combination with the mTOR inhibitor AZD2014.

Example 5: Single Agent and Combination In Vivo Anti-Tumor Activity in a Human Small Cell Lung Cancer Tumor Model Compound 2 and AZD2014 (vistusertib, an mTOR inhibitor shown below) induced single agent and combination anti-tumor activity in NCI-1H1048 tumor bearing mice (FIG. 9). A weekly (qw) iv administration of Compound 2 at 103 mg/kg (equivalent to 30 mg/kg Compound A) resulted in significant anti-tumor activity of 76% TGI (p<0.05). Administration of the mTOR inhibitor AZD2014 at 15 mg/kg daily (qd) resulted in significant anti-tumor activity of 84% TGI (p<0.05). Combination of Compound 1 with AZD2014 resulted in 91% tumor regression (p<0.05 relative to single agent activity).

Compound 1 was formulated in citrate/phosphate buffer pH 5.0 containing 4.5% w/v glucose and dosed intravenously (iv) in a volume of 5 ml/kg. AZD2014 was formulated in 0.5% hydroxypropyl methylcellulose/0.1% Tween 80 and dosed oral in a volume of 10 ml/kg 5×106 NCI-H1048 tumor cells were injected subcutaneously in the right flank of C.B.-17 SCID female mice in a volume of 0.1 mL containing 50% matrigel. Tumor volume (measured by caliper) was calculated using the formula: length (mm)× width (mm)$^2$×0.52. For efficacy studies, mice were randomized based on tumor volume and growth inhibition was assessed by comparison of the differences in tumor volume between control and treated groups. Dosing began when mean tumor volume reached approximately 124 mm$^3$.

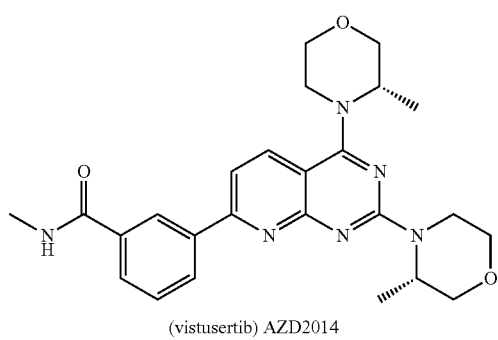 [SMILES: CNC(=O)c1cccc(-c2ccc3c(N4CCOC[C@@H]4C)nc(N4CCOC[C@@H]4C)nc3n2)c1]

(vistusertib) AZD2014

Example 6: Single Agent and Combination In Vivo Anti-Tumor Activity in a Human DLBCL Model 5×10$^6$ OCI-Ly10 tumor cells were injected subcutaneously in the right flank of C.B.-17 SCID female mice in a volume of 0.1 mL containing 50% matrigel. Compound 1 was formulated in citrate/phosphate buffer pH 5.0, diluted 1 to 10 with 5% glucose containing 1% w/v Kolliphor HS15, and dosed as a weekly intravenous (iv) administration at a volume of 5 mL/kg at a dose of 103 mg/kg (30 mg/kg API). Acalabrutinib was formulated in 0.5% hydroxypropyl methyl cellulose/0.2% Tween 80, and dosed twice a day (bid) as an oral (po) administration at a volume of 10 mL/kg at a dose of 12.5 mg/kg. Tumor volumes (measured by caliper), animal body weight, and tumor condition were recorded twice weekly for the duration of the study. The tumor volume was calculated using the formula: length (mm)×width (mm)$^2$×0.52. For efficacy studies, growth inhibition from the start of treatment was assessed by comparison of the differences in tumor volume between control and treated groups. Dosing began when mean tumor size reached approximately 166 mm3.

Figure 10:
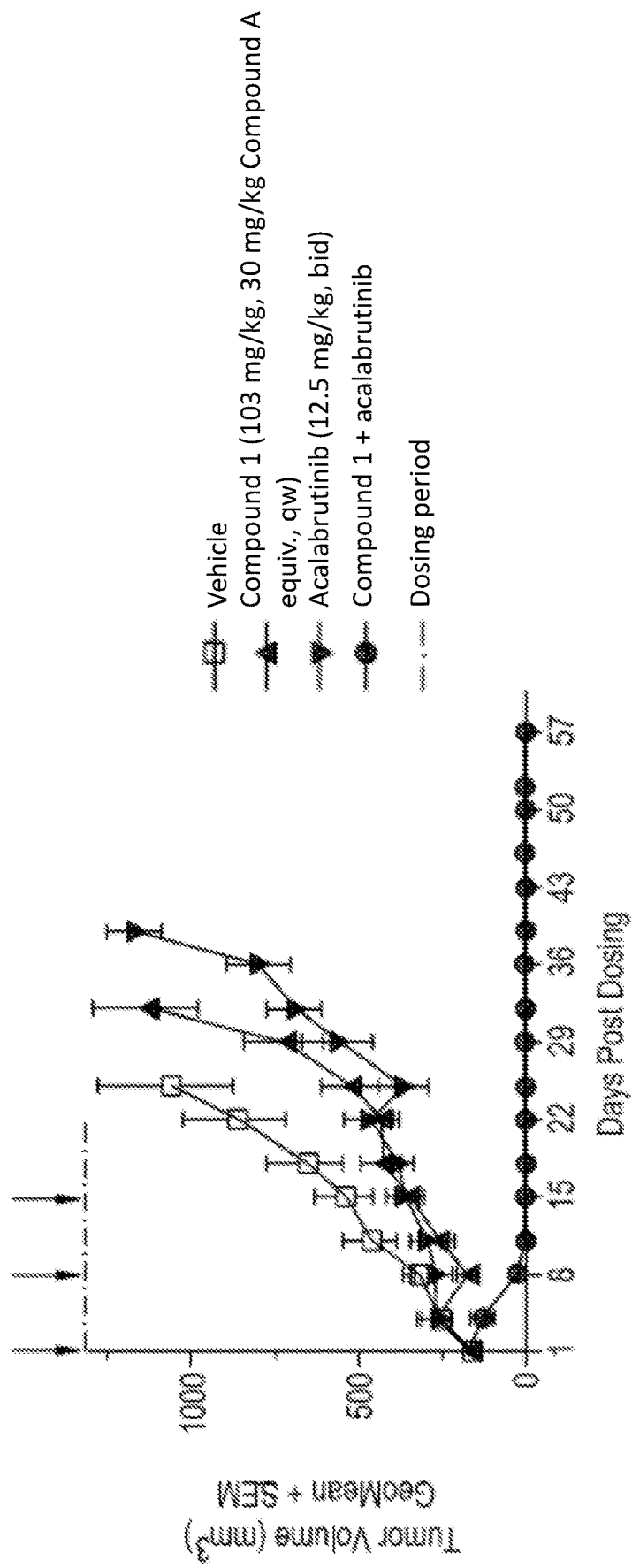
FIG. 10 illustrates the in vivo anti-tumor activity in a human DLBCL tumor model exhibited by Compound 1 in combination with acalabrutinib.

As shown in FIG. 10, combining Compound 1 with acalabrutinib resulted in significant in vivo anti-tumor activity in the OCI-Ly10 DLBCL xenograft model. Weekly iv administration of 103 mg/kg of Compound 1 (30 mg/kg Compound A) in combination with twice a day oral administration of 12.5 mg/kg acalabrutinib resulted in complete regression in 8 out of 8 tumor bearing mice 10 days after treatment initiation. Complete regressions were sustained even after the end of treatment (3 weeks treatment with 35 days follow up). In contrast, single agent Compound 1 or acalabrutinib showed relatively modest single agent activity, reaching approximately 64% and 58% tumor growth inhibition (TGI) respectively.

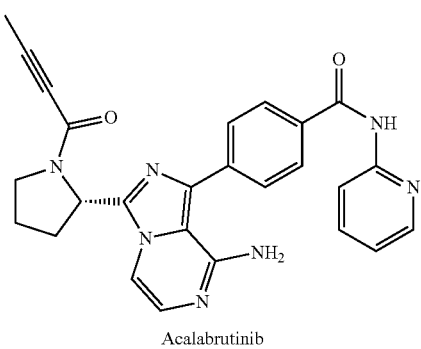 [SMILES: CC#CC(=O)N1CCC[C@H]1c1nc(-c2ccc(C(=O)Nc3ccccn3)cc2)c2c(N)nccn12]

Acalabrutinib

Example 9: Lyophilization Investigations

Compounds 1 and 2 hydrolyze to release the active moiety in the presence of water and therefore steps must be taken to minimize moisture exposure and the rate of hydrolysis by using alternate solvents, controlling temperature and time during manufacture of the lyophile. Several non-aqueous solvents were investigated on paper for use in lyophilization including for example, acetone, acetic acid (glacial), acetonitrile, tert-butyl alcohol, ethanol, n-propanol, n-butanol, isopropanol, ethyl acetate, dimethyl carbonate, dichloromethane, methyl ethyl ketone, methyl isobutyl ketone, 1-pentanol, methyl acetate, methanol, carbon tetrachloride, dimethyl sulfoxide, hexafluoroacetone, chlorobutanol, dimethyl sulfone, acetic acid, cyclohexane and glacial acetic acid.

After initial investigation glacial acetic acid and tert-butyl alcohol were found potentially suitable candidates. These two solvents were further evaluated to determine whether both compounds have sufficient solubility to achieve >100 mg/mL solution concentration by visual observations. In this method approximately 20 mg compound was added in to 200 μL of each solvent and sample was sonicated to aid dissolution.

Both Compounds 1 and 2 rapidly dissolved in glacial acetic acid, but didn't dissolve in tert-butyl alcohol until prolonged sonication. Prolonged sonication resulted in temperature increase which might have also contributed in the dissolution of both compounds in tert-butyl alcohol. Once cooled down to room temperature, precipitation was seen in both Compound 1 and 2 solutions in tert-butyl alcohol indicating that most likely heating effect due to prolonged sonication resulted in supersaturated solution which is not stable at room temperature. Therefore, it was concluded that both Compounds 1 and 2 had acceptable solubility in glacial acetic acid whereas, based on the current dose predictions, the solubility was insufficient in tert-butyl alcohol for lyophilization process.

Various solvents were also evaluated in combination with glacial acetic acid for use in the lyophilization process, including acetone, anisole, 1-butanol, 2-butanol, butyl acetate, tert-butyl methyl ether, DMSO, ethanol, ethyl acetate, ethyl ether, ethyl formate, formic acid heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate. None of these solvents was found suitable for freeze drying in combination with glacial acetic acid. Therefore, only glacial acetic acid was taken forward to develop the lyophilization process for both compounds.

For the lyophilization process evaluation, Compounds 1 and 2 were separately dissolved in glacial acetic acid at approximately 100 mg/mL concentration and filled into 10 mL freeze drying type I glass vials with lyophilization stoppers and frozen to −40° C. These samples were lyophilised using a shelf temperature of around −40° C. to −35° C. and a vacuum pressure of approximately 100 mTorr. Secondary drying was performed by heating to 20° C. over 6 hours and holding at this temperature for 1 hour at around 100 mTorr. The resultant lyophiles had a good appearance by visual inspection and were further tested for physical and chemical stability.

In addition to the chemical stability of lyophile during the lyophilization process, the chemical stability of both Compound 1 and 2 solutions in glacial acetic acid was also tested at ambient and frozen conditions by using reversed phase HPLC with UV detection to determine the concentration of Compound A in the formulations, in accordance with the following parameters, shown for analysis of Compound 1:

| | | | |
|---|---|---|---|
| Mobile Phase A | 0.07% trifluoroacetic acid in water | | |
| Mobile Phase B | 0.07% trifluoroacetic acid in acetonitrile | | |
| Column | Waters X Bridge Phenyl, 2.5 μm 30 × 3.0 mm | | |
| Column temperature | 60° C. | | |
| Flow rate | 1.0 ml/min | | |
| Gradient | Time | % Mobile Phase A | % Mobile Phase B |
| | 0 min | 60 | 40 |
| | 6.0 | 20 | 80 |
| | 6.5 | 20 | 80 |
| | 6.7 | 60 | 40 |
| | 8.0 | 60 | 40 |
| Injection volume | 4 μL | | |
| Run time | 8.0 min | | |
| Detector mode/wavelength | UV at 332 nm | | |
| Rt Compound A | Approximately 2.5 min | | |
| Rt Compound 1 | Approximately 5.0 min | | |

Compound A was used to quantify the free amount of Compound A in the lyophilized formulations of Compound 1. To prepare the standard solution containing Compound A at 30 μg/mL, approximately 15 mg of Compound A was accurately weighed into a 50 mL volumetric flask with dilution to volume with dimethylacetamide. An amount of 5 mL of the resulting all calibaration solution was added to a 50-mL volumetric flask and diluted to volume with dimethylacetamide. To prepare the samples of Compounds 2, approximately 20 mg of Compound 1 were accurately weighted as a dry powder into a 20-mL volumetric flask, followed by dilution to volume with dimethylacetamide. Calculation of % Free Compound A:

$$\text{Compound } A \text{ assay (mg/mL)} = \\ \frac{\text{Compound } A \text{ peak area sample}}{\text{Avg peak Compound } A \text{ in calibration standard}} \times \\ \frac{\text{Weight (mg) Compound } A \text{ in } \textit{calidbration} \text{ standard}}{\text{Volume (mL) Compound } A \text{ in } \textit{calidbration} \text{ standard}} \times \\ \frac{\text{Purity Compound } A \text{ reference standard}}{100}$$

$$\% \text{ free Compound } A = \\ \frac{\text{Compound } A \text{ assay (mg/mL)}}{\left(\text{Compound 1 sample concentration (mg/mL)} \times \frac{\text{Amt Compound } A \text{ on Compound 1}}{100}\right)} \times 100$$

The results were compared with Compound A (% w/w) in Compounds 1 and 2, as shown in Table 6.

TABLE 6

Percent Free Compound A by HPLC

| Sample ID | Compound | Free Compound A (%) |
|---|---|---|
| Drug Substance | 1 | 0.19 |
| | 2 | 0.07 |
| Lyophilized samples | 1 | 1.243 |
| | 2 | 0.261 |
| Frozen sample solution in glacial acetic acid | 1 | 1.166 |
| | 2 | 0.196 |
| Ambient sample solution in glacial acetic acid | 1 | 4.621 |
| | 2 | 0.635 |

Table 6 illustrates that in the samples of Compound 1 there was significant degradation during the lyophilization process, as the % free Compound A increased to ~1.2%. This increase was equivalent to the frozen solution, which indicates that the degradation primarily occurred in the solution preparation process. The degradation in the Compound 1 solution in glacial acetic acid stored at ambient conditions was much higher than frozen conditions. However, there was no significant degradation in the lyophile and frozen solutions of Compound 2, whereas, the Compound 2 solution in glacial acetic acid stored at ambient conditions also exhibited significant degradation.

Therefore, it was concluded that both Compound 1 and 2 solutions in glacial acetic acid were stable during lyophilization process and storage at frozen conditions (-20° C.).

A second small-scale lyophilization procedure was performed on Compounds 1 and 2. Solutions of Compound 1 and 2 were prepared by dissolving 134.8 mg of Compound 1 in 1.348 mL acetic acid, and 143.2 mg Compound 2 in 1.432 mL of acetic acid. 200 µL of each solution was taken for ambient solution stability studies and for frozen solution stability studies. The remainder of the solutions were freeze dried in accordance with the procedure below in 10 mL clear vials:

1. Cool to -40° C. over 2 hours
2. Hold at -40° C. for 30 mins
3. Vacuum at 300 mTorr at -40° C. for 1440 mins (1 day)
4. Ramp shelf to -35° C. over 1 day
5. Heat to 20° C. over one day reducing pressure to 100 mTorr
6. Hold at 20° C. at 100 mTorr for 2 hours
7. Return to ambient using $N_2$ bleed and close vials within freeze dryer.
8. Unload and seal, store in freezer.

It was concluded that both Compound 1 and 2 solutions in glacial acetic acid were stable during lyophilization process and storage at frozen conditions (-20° C.).

Objective

Only Compound 1 was taken forward for further product development. The scope of the studies included the formulation of a bulk solution comprising Compound 1, the control of critical process parameters, material compatibility, and lyophilization. Three full scale laboratory batches of approximately 160 vials/1.77 kg per batch were manufactured. Compound 1 was formulated as a 50 mg/mL solution in glacial acetic acid and filled at a nominal target volume of 10.0 mL in a 50 mL Type I clear glass vial for freeze drying to manufacture drug product containing 500 mg of Compound 1 in a 50-mL vial, with no other excipients.

Materials

Table 7 lists the materials used in the studies. All materials were within their assigned expiration dates.

TABLE 7

Materials List

| Materials | Dimensions | Vendors |
|---|---|---|
| Compound 1 | 5 bottles (80 g each) 1 bottle (50 g) | N/A |
| Acetic acid anhydrous | 1 L bottles | Rath burn |
| Platinum cured silicon tube | 0.125" ID | Saint-Gobain Performance Plastics |
| Platinum cured silicon tube | 0.25" ID | Saint-Gobain Performance Plastics |
| Platinum cured silicon gasket | 3/4" ID | Precision Polymer Products |
| Ultrapure nitrogen | UN1066 | Air-Gas |
| 316L SS Filler Nozzle | 1/8" ID | Cole-Parmer (Overlook Industries) |
| Millipak 20 PVDF | 0.22 µm pore size | Millipore |
| 1L TK8, BPV 2D Holding bag | A-Flex 20", 1/4" × 1/4" × 1/8" Luer | ATMI/Pall Life Sciences |

Equipment

Equipment listed in Table 8 were used in the studies from development to full scall technical batches. Weighing, mixing and compounding were conducted in an isolator purged with nitrogen to reduce moisture in the atmosphere and inhibit hydrolysis of Compound A from Compound 1. The compound vessel was controlled at 18° C.±1° C. to minimize hydrolysis of Compound A from Compound 1 in acetic acid during compounding. This temperature could not be set too low because of the risk the acetic acid would freeze. Filtering and fill were performed on the laboratory bench top at ambient temperature.

TABLE 8

Equipment List
Equipment

2 L & 3 L Glass jacketed vessel (Chemglass)
Teflon coated Stir Bars, 2" $ 3" ID
VWR Magnetic Stirrer with digital display
VWR Chiller unit
Fisher Termometer
Sampling Isolator
Top Loader Balance
Analytical Balance
Watson Marlow, Peristaltic Filter Pump
Watson Marlow, Flexicon, Peristaltic Fill Pump
Lyo Star III, Development Freeze Dryer Container Closures Vials were hand washed, rinsed with distilled water and dried in the oven at 130° C. for 6 hours. These were equilibrated at ambient temperature before subjected to filling. Stoppers and seals were used as-is without additional treatment (Table 9).

TABLE 9

Primary Container Closures Components 50 mL vial, 20 mm crown, non-sterile, clear glass, type-I vial, Schott, p/n 1097603
20 mm Flurotec lyo stopper, West, ready for sterilization, p/n 19700033 or 19700041
20 mm Flip-Off Matte Top Seal, West, White, p/n 54202047

Final Batch Manufacturing Process

The formulation comprising Compound 1 was compounded at 50 mg/mL concentration in glacial acetic acid according to the master formula in Table 10.

Calculation

The final weight of Compound 1 was corrected for purity (98.9%) from the certificate of analysis (CoA). The corrected weight is calculated as follows:
 (a) Calculate Compound 1 weight required for the batch according to the master formula in Table 10.
 (b) For a 100 mL solution, Compound 1 weight=100 mL (4.75/100)=4.75 g
 (c) Correcting for purity, Compound 1 weight=4.75+ (98.9/100)=4.8028 g.

TABLE 10

Master Formula Dispensing

| Ingredient | Concentration (mg/mL) | % w/w[1] |
|---|---|---|
| Compound 1 | 50 mg/mL | 4.75 |
| Glacial acetic acid[2] | Qs to 1 mL | Qs to 100% |

[1]Formulation density = 1.0531 g/mL @ 25° C.
[2]Density = 1.05 g/mL

Equipment Set Up
 (a) All equipment (balance, vessel, mixer) was placed inside the isolator. A silicone tube from the nitrogen tank was connected to the isolator inlet. The nitrogen valve was turned on and adjusted the regulator to maintain nitrogen flow at approximately 200 SCFH (standard cubic feet per hour).
 (b) The isolator was purged with pure nitrogen gas for not less than 10 minutes, and preferably for at least 30 minutes and a steady flow of nitrogen was maintained for the compounding duration.
 (c) The glass jacketed compounding vessel and mixer was set up and connected to the chiller unit to the vessel.
 (d) The chiller temperature was set to 18° C. and the filler reached 18° C. before proceeding.

Compounding
 (a) A 90% of batch weight quantity of anhydrous glacial acetic acid was dispensed into the glass vessel.
 (b) A slow mixing between 200 to 300 rpm was initiated.
 (c) The acetic acid solution was cooled to 18° C. temperature and the solution was maintained at that temperature for a minimum of 5 minutes.
 (d) The corrected pre-weighed quantity of Compound 1 was dispensed into the vessel with continuous mixing. This point was set as time zero and the total target time for a batch from addition of Compound 1 to acetic acid to placement of the trays into the freeze dryer was up to 7 hours maximum, to minimize generation of released free Compound A.
 (e) The mixing speed was increased as needed to achieve complete dissolution of Compound 1.
 (f) Glacial acetic acid was added to batch weight and the solution was mixed for an additional 10 min.
 (g) At this stage time zero sample (2×10 mL) was taken to analyze for appearance, density, osmolality, assay and impurities testing. The sample was diluted to 1 mg/mL concentration in dimethylacetiamide (DMA) as per HPLC method described above. All samples were stoppered and stored at −20° C.

Filtering
 (a) The solution was filtered immediately after preparation.
 (b) The 0.25" ID silicon tube was connected from the vessel to 2 Millipak 20 filters connected in tandem. The silicon tube was routed through the peristaltic pump head and connect the tube outlet to a (TK8) holding bag or glass pyrex bottle.
 (c) The solution comprising Compound 1 was slowly pump filtered into the receiving container discarding the initial 10 to 20 mL volume.
 (d) A post-filter sample was taken for assay and impurity tests. The sample was diluted to 1 mg/mL concentration in dimethylacetamide (DMA) as per HPLC method described above. The sample was stoppered and stored at −20° C.

Product Fill
 (a) The product fill precision was determined at ambient temperature using the peristaltic pump.
 (b) The solution density was measured at ambient temperature and set the fill weight based on nominal 10 mL/vial.
 (c) The vials were filled at the target fill weight. Each vial was partially stoppered and immediately loaded onto the freeze dryer once the tray is filled.
 (d) Two 10 mL sample vials were taken at the end of the fill for assay and impurities. The sample were quenced immediately with DMA (1 mg/mL) and stored at −20° C.

Freeze Drying

The final freeze drying process in Table 11 applied to three technical batches. The product vials were loaded at 5° C. shelf temperature. Freezing was conducted at a slower ramp rate of 0.2° C./min. The frozen acetic acid was sublimed using a ramp from −30° C. to −20° C. over 30 hours then static at −20° C. for 55 hours during primary drying at 100 mTorr vacuum pressure.

Any remaining solvent was removed through desorption at 25° C. and 20 mTorr reduced pressure during 12 hours secondary drying. All vials were back filled with nitrogen before stoppering at a vacuum pressure of 700 Torr and stored at the recommended storage temperature of −20° C. The back fill pressure (700 Torr) was maintained at near atmospheric level (760 Torr) to maintain a slight vacuum pressure inside the vial in order to ensure container closure integrity of the stoppered vial. The vacuum pressure setting (20 mTorr) before back fill in Table 11 refers to the running vacuum pressure before the start of the back fill process, which corresponds to the secondary drying vacuum pressure of 20 mTorr.

TABLE 11

| Freeze Drying Process | | | | |
|---|---|---|---|---|
| Product Load Phase | | Shelf Set Point | 5° C. | |
| Thermal Treatment Phase | | | | |
| Step | Step Control Mode | Temperature S.P. (° C.) | Ramp Time (Min) | Soak Time (Min) |
| 1 | Normal | −30 | 175 | 90 |
| 2 | Normal | −5 | 50 | 240 |
| 3 | Normal | −30 | 125 | 90 |
| Freeze Condenser | Condenser SP | −50 | N/A | N/A |
| Evacuate | | Evacuate SP at 100 mT | | |

| Step | Step Control Mode | Temperature S.P. (° C.) | Ramp Time (Min) | Soak Time (Min) | Vac. Cont. SP (mT) |
|---|---|---|---|---|---|
| Primary Dry Phase | | | | | |
| 1 | Normal | −30 | 0 | 60 | 100 |
| 2 | Normal | −20 | 1800 | 3320 | 100 |
| | Pressure Rise Test | | | N/A | No |
| Secondary Dry Phase | | | | | |
| 1 | Normal | 25 | 520 | 720 | 20 |
| | Pressure Rise Test | | | N/A | No |

| Stoppering Phase | | |
|---|---|---|
| Shelf Set Point | −20 | ° C. |
| Vacuum Before Back Fill | 20 | mT |
| Back Fill before Stoppering | Yes | |
| Stoppering Mode | Manual | |

The final lyophilized product was analysed for, appearance, assay, impurities, water content, residual solvent (acetic acid), reconstitution (time, appearance, pH, particle count and particle size).

Results:
Technical Batch 1

The total batch size, including acetic acid and Compound 1 was 1.770 kg. A five hour hold at 18° C. was conducted before the solution was filtered, filled and loaded into the lyophilizer to mimic the expected processing time of the GMP batch size (~23 kg). The total process time from beginning of addition of Compound 1 to the acetic acid was six hours and 38 minutes. Compound 1 dissolved completely within 12 minutes. The lyo cake appearance was a smooth, compact and off-white. Tables 12-17 provide the characterization of Technical Batch 1.

Technical Batch 1 was reconstituted in a 50 mM citrate buffer (pH 5) in 5% (w/w) dextrose (3.68 mg/mL citric acid monohydrate, 9.56 mg/mL sodium citrate dihydrate and 50 mg/mL dextrose anhydrous). An alternative diluent or solvent is a 100 mM acetate buffer (pH 5) in 2.5% (w/w) dextrose (1.76 mg/mL acetic acid, 5.78 sodium acetate anhydrous, 25 mg/mL dextrose anhydrous).

TABLE 12

Technical Batch 1 Reconstitution Data

| Vial No. | Appearance | Volume (mL) | Time to complete dissolution (min) | pH |
|---|---|---|---|---|
| 1 | Clear solution, faint yellow color, free of visible particles | 20 | 5.41 | 5.04 |
| 2 | Clear solution, faint yellow color, free of visible particles | 20 | 5.23 | 5.04 |

TABLE 13

Tech Batch 1 Impurities (% area)

| Sample | % Free Comp A | Assay Comp A (% label) | % Total Imp. | % Imp. RRT-0.17 | % Imp. RRT-0.42 | % Imp. (Comp A) RRT-0.53[2] | % Imp RRT-0.58 | % Imp RRT-0.82 | % Imp RRT-0.89 |
|---|---|---|---|---|---|---|---|---|---|
| T = 30 (pre-filter) | ND | 99.21 | 0.31 | | | | | 0.31 | |
| Post-filter | 0.24 | 99.86 | 0.59 | | 0.10 | 0.21 | | 0.28 | |
| End of fill (6 h, 14 min) | 0.22 | 99.67 | 0.53 | | 0.06 | 0.19 | | 0.82 | |
| Lyo Vial-1 | 0.28 | 106.29 | 0.62 | | 0.09 | 0.25 | | 0.28 | |
| Lyo Vial-2 | 0.28 | 99.59 | 0.65 | | 0.11 | 0.25 | | 0.29 | |

TABLE 14

Residual Moisture in Technical Batch 1

| Sample | Cake weight (g) | % Water (w/w) (KF) | Average % Water (w/w) |
|---|---|---|---|
| 1 | 0.5230 | 0.0040 | 0.0031 |
| 2 | 0.5011 | 0.0021 | |

TABLE 15

Residual Solvent in Technical Batch 1

| Sample | % Acetic Acid (w/w) (HPLC) | Average % Acetic Acid (w/w) |
|---|---|---|
| End of primary drying-vial 1 | 7.81 | 8.17 |
| End of primary drying-vial 2 | 8.52 | |
| Secondary drying-vial 1 | 0.05 | 0.05 |
| Secondary drying-vial 2 | 0.04 | |
| Lyo-vial 1 | 0.01 | 0.01 |
| Lyo-vial 2 | 0.01 | |

TABLE 16

Technical Batch 1 Particle Counts (USP <788>)[1]

| USP Specification (particles/container) | Cumulative Average particles in 5 mL (n = 3) | Number of particles/mL | Number of particles/vial |
|---|---|---|---|
| 6000 particles ≥ 10 μm | 156.33 | 31.3 | 322 |
| 600 particles ≥ 25 μm | 0.67 | 0.1 | 1 |

[1]2 vials pooled, 40 mL total

TABLE 17

Technical Batch 1 Particle Size (Malvern ZetaSizer Nano-ZS90) at 25° C.

| Sample | Z-Average d · nm | PDI |
|---|---|---|
| Top Tray | 18.87 | 0.281 |
| | 18.77 | 0.279 |
| | 18.57 | 0.280 |
| Bottom Tray | 18.20 | 0.234 |
| | 17.85 | 0.228 |
| | 18.57 | 0.280 |

Technical Batch 2

A 1.681 L (1.77 kg) batch of Compound 1 and acetic acid was compounded, filtered, filled an lyophilized using the same process and timings as outlined above for Technical Batch 1. The total process time from dispensing of Compound 1 to start of lyophilization was six hours and 53 minutes. Time to complete dissolution of Compound 1 was within 15 minutes. The target fill for the batch was 10.3 mL/vial (10.85 g/vial, density 1.0531). The lyo cake appearance was a smooth, compact, off-white and consistent with the appearance of Technical Batch 1 and specifications. Table 18 summarizes the impurities found in Technical Batch 2.

TABLE 18

Technical Batch 2 Impurities (% area)

| Sample | Assay Comp 1 (mg/mL) | Assay Comp 1 (% label) | % Free Comp A | Total Imp. (%) | % Imp. RRT-0.42 | % Imp. RRT-054 | % Imp RRT-0.83 |
|---|---|---|---|---|---|---|---|
| T = 30 (Pre-filter) | 49.5 | 99.1 | ND | 0.26 | | | 0.26 |
| Post Filter | 50.2 | 100.5 | 0.09 | 0.39 | 0.05 | 0.09 | 0.25 |
| End of Fill | 50.5 | 101.4 | 0.12 | 0.42 | 0.06 | 0.11 | 0.25 |

Technical Batch 3

A 1.681 L (1.77 kg) batch size of Compound 1 and acetic acid was compounded, filtered, filled and lyophilized using the same process and timing as outlined above for Technical Batch 1 and 2. The total process time from dispensing Compound 1 to start of lyophilization was 6 hours and 47 minutes. Time to complete dissolution of Compound 1 was within 15 minutes. The target fill for the batch was 10.3 mL/vial (10.85 g/vial, density 1.0531 g/mL). Results were near 100% for assay of all samples with total impurities below 0.5%. The lyo cake appearance for Technical Batch 3 was a smooth, compact, off-while cake consistent with the appearance of Technical Batches 1 and 2. Table 19 summarizes the impurities of Technical Batch 3.

TABLE 19
| | Technical Batch 3 Impurities (% area) | | | | | | |
|---|---|---|---|---|---|---|---|
| Sample | Assay Comp 1 (mg/mL) | Assay Comp 1 (% label) | Assay Comp A (mg/mL) | % Free Comp A | Total Imp. (%) | % Imp. RRT-0.42 | % Imp. RRT-054 | % Imp RRT-0.83 |
| T = 30 (Pre-filter) | 49.9 | 99.8 | ND | ND | 0.27 | | | 0.27 |
| Post Filter | 49.9 | 99.8 | 0.02 | 0.15 | 0.46 | 0.07 | 0.13 | 0.26 |
| End of Fill | 50.0 | 100.1 | 0.02 | 0.15 | 0.47 | 0.08 | 0.13 | 0.26 |
The invention claimed is:
1. A pharmaceutical composition comprising a lyophilized dendrimer of formula (IV):
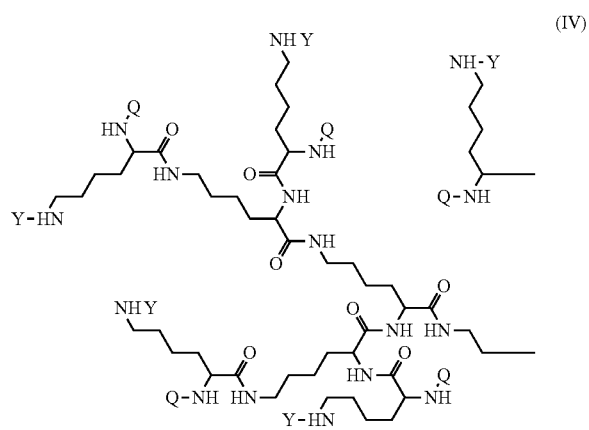
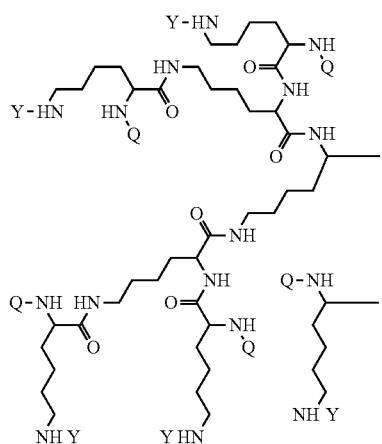

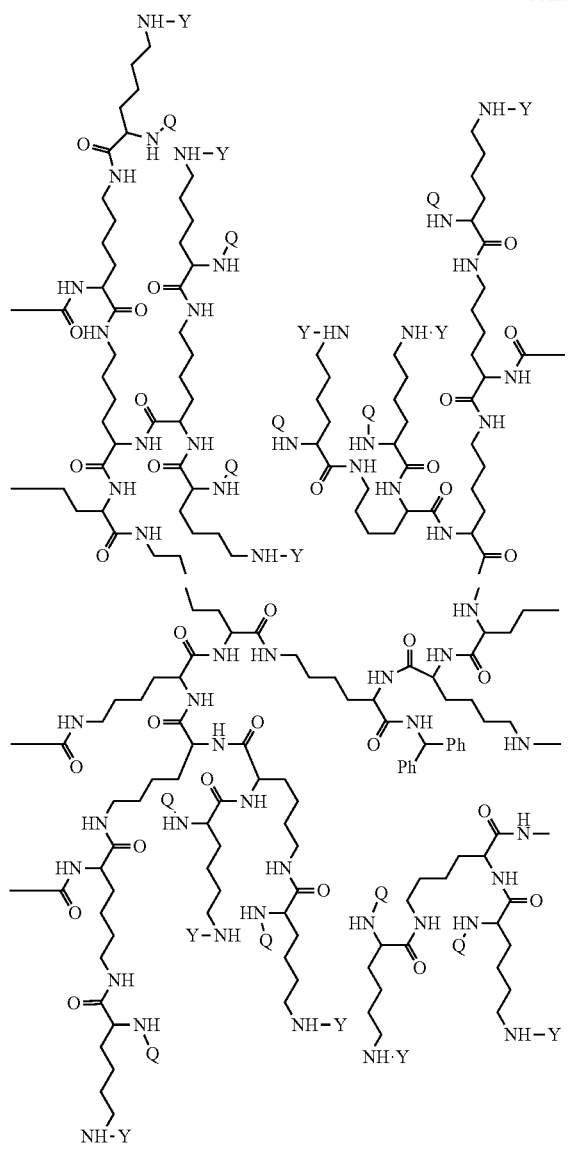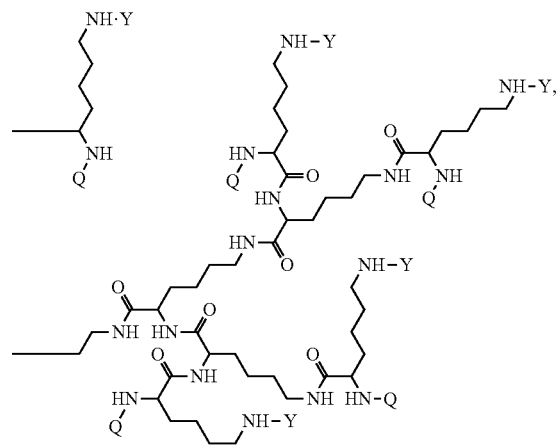

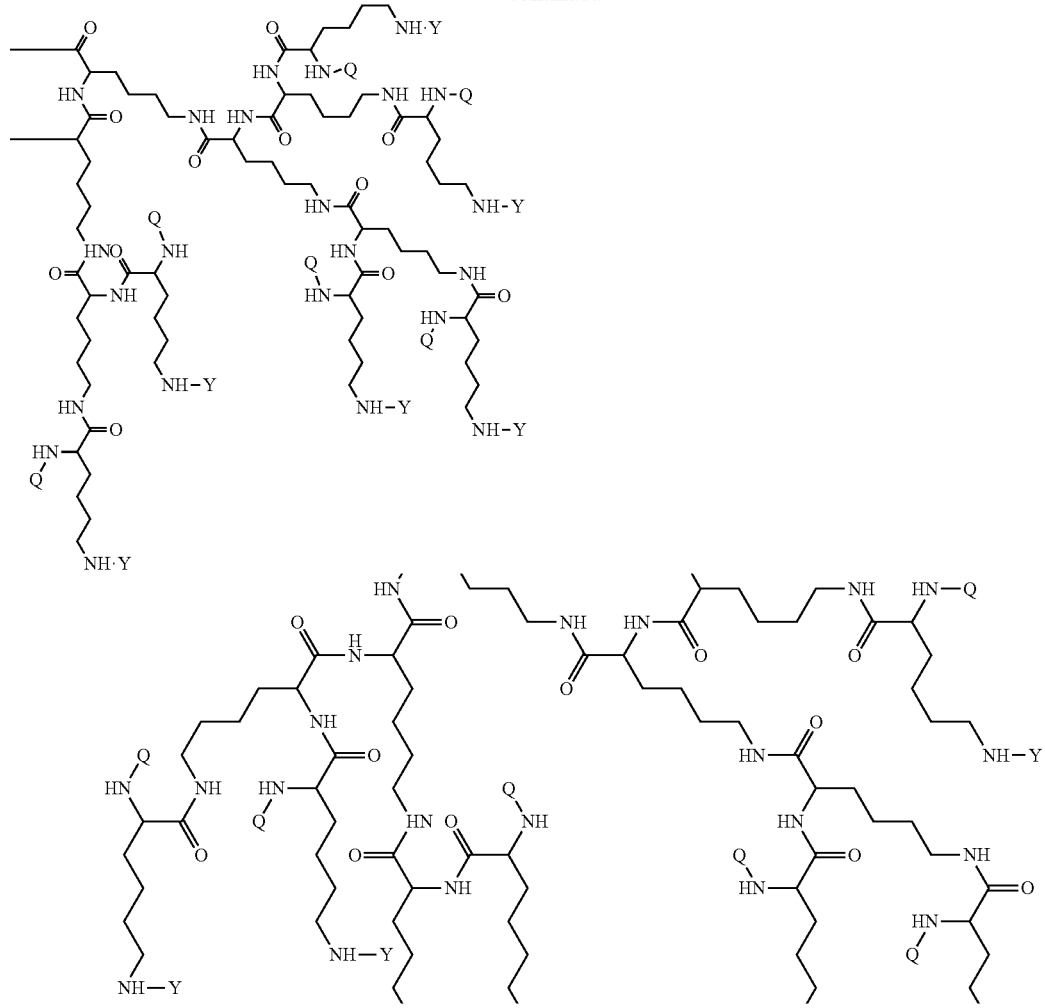
or a pharmaceutically acceptable salt thereof, wherein Y is $PEG_{1800-2400}$ or H; Q is H or L-AA, in which L-AA has the structure:
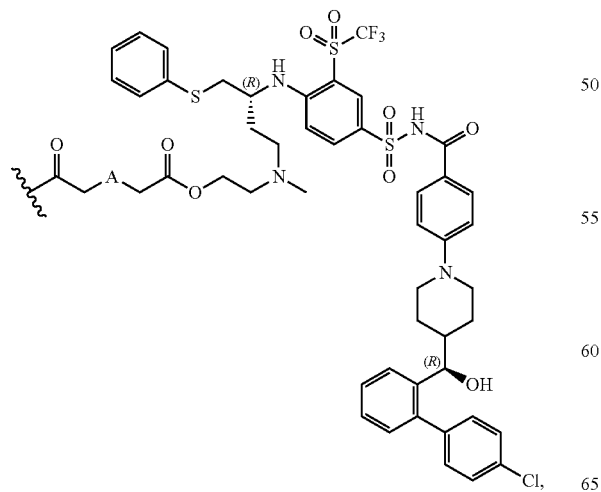

A is —N(CH$_3$), provided that if the sum of PEG$_{1800-2400}$ and L-AA is less than 64, the remaining Q and Y moieties are H, and provided that at least one Q is L-AA.
2. The pharmaceutical composition of claim 1, wherein the lyophilized dendrimer of formula (IV) is a dendrimer of formula (V):
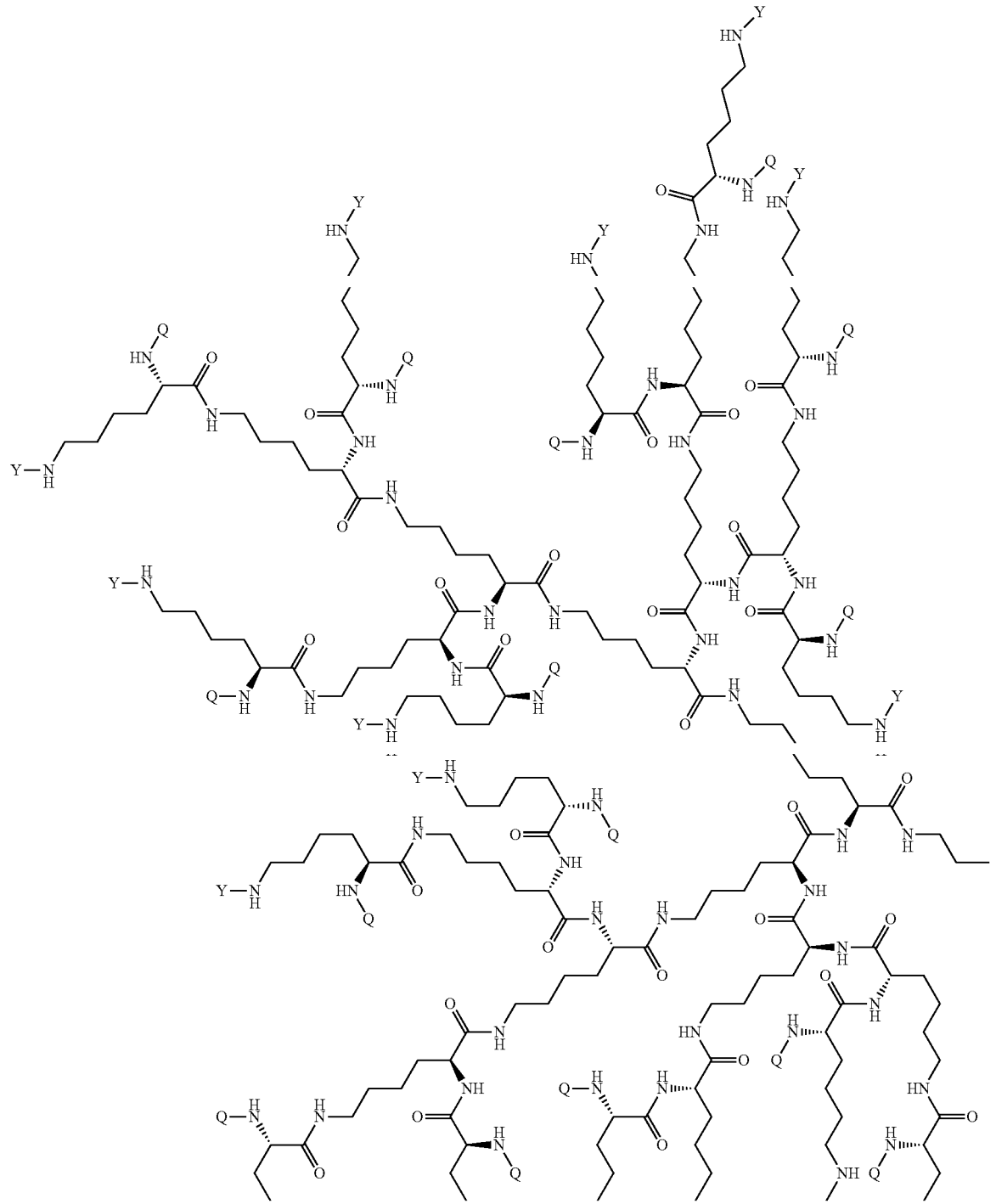

137 138
-continued
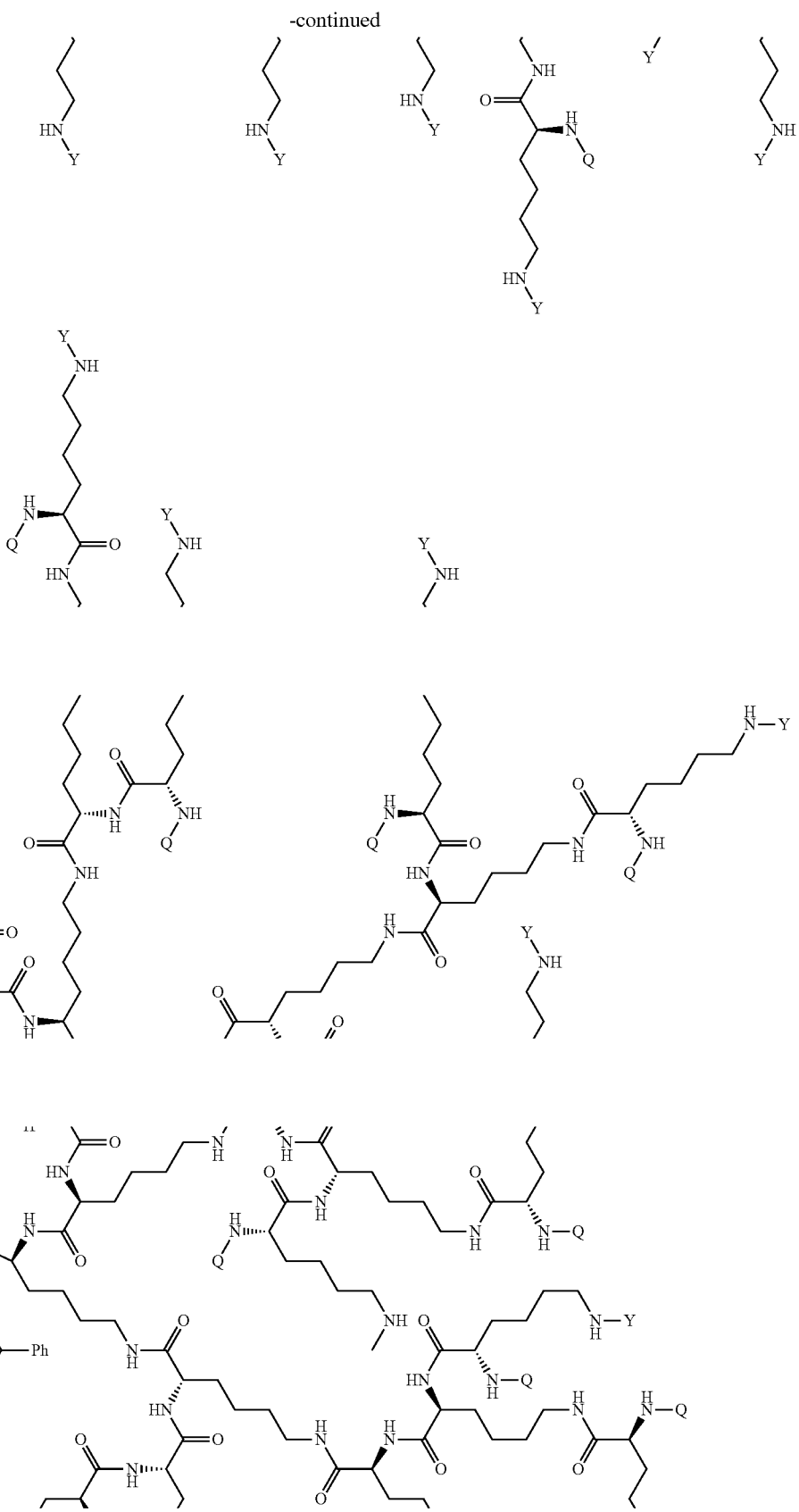

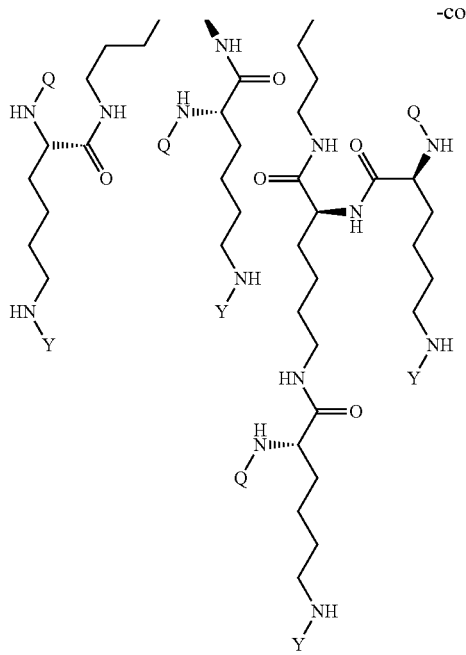
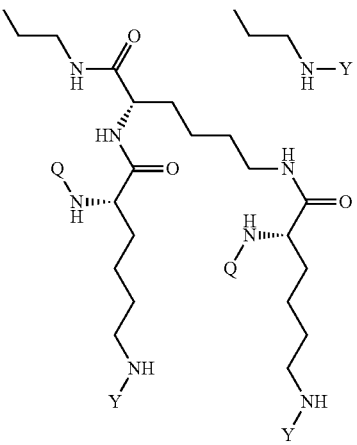

or a pharmaceutically acceptable salt thereof, wherein

Y is $PEG_{1800-2400}$ or H;

Q is H or L-AA, wherein L-AA has the structure:

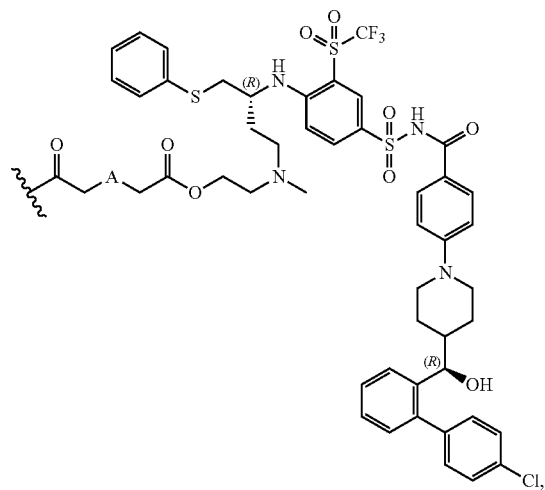

A is —$N(CH_3)$, provided that if the sum of $PEG_{1800-2400}$ and L-AA is less than 64, the remaining Q and Y moieties are H, and provided that at least one Q is L-AA.

3. The pharmaceutical composition of claim 1, wherein the sum of $PEG_{1800-2400}$ and L-AA is an integer between 50 and 64.

4. The pharmaceutical composition of claim 1, wherein the dendrimer has between 25 and 32 $PEG_{1800-2400}$.

5. The pharmaceutical composition of claim 1, wherein the dendrimer has between 25 and 32 L-AA.

6. The pharmaceutical composition of claim 1, wherein the dendrimer has between 0 and 14 hydrogens at the Q and/or Y positions.

7. The pharmaceutical composition of claim 1, wherein the PEG has an average molecular weight of between about 2000 and 2200 Da.

8. The pharmaceutical composition of claim 1, wherein the PEG has a PDI of between about 1.00 and 1.10.

9. The pharmaceutical composition of claim 1, wherein the dendrimer has a molecular weight of between about 90 and 120 kDa.

10. The pharmaceutical composition of claim 1, wherein the pH of the pharmaceutical composition is between about 4.0 and about 6.0.

11. The pharmaceutical composition of claim 1, wherein the pharmaceutical composition comprises between about 90-110% of the dendrimer of formula (IV) when assayed against a reference standard of known purity.

12. The pharmaceutical composition of claim 1, wherein the purity of the pharmaceutical composition is not less than 85% as measured by SEC-UV.

13. The pharmaceutical composition of claim 1, wherein the pharmaceutical composition comprises less than about 3% w/w total impurities.

14. The pharmaceutical composition of claim 13, wherein the pharmaceutical composition comprises ≤1.0% w/w free Compound A.

15. The pharmaceutical composition of claim 13, wherein the pharmaceutical composition comprises ≤0.5% w/w any single unspecified impurity.

16. The pharmaceutical composition of claim 13, wherein the pharmaceutical composition comprises ≤1.2% w/w total free impurities.

17. The pharmaceutical composition of claim 1, wherein the pharmaceutical composition comprises not more than 1.5% w/w acetic acid.

18. The pharmaceutical composition of claim 1, wherein the pharmaceutical composition has an average particle size determined by DLS of between about 15 and about 25 d.nm.

19. The pharmaceutical composition of claim 1, wherein the pharmaceutical composition has an a PDI as determined by DLS of between about 0.20 and about 0.30.

20. The pharmaceutical composition of claim 1, wherein the pharmaceutical composition comprises not more than about 6000 particulates of greater than or equal to about 10 µm per 50 mL container upon reconstitution in a pharmaceutically acceptable diluent or solvent.

21. The pharmaceutical composition of claim 1, wherein the pharmaceutical composition comprises not more than about 600 particulates of greater than or equal to about 25 µm per 50 mL container upon reconstitution in a pharmaceutically acceptable diluent or solvent.

22. The pharmaceutical composition of claim 1, wherein the osmolality of the pharmaceutical composition is between about 200 and about 400 mOsmol/kg upon reconstitution in a pharmaceutically acceptable diluent or solvent.

23. The pharmaceutical composition of claim 1, wherein the pharmaceutical composition comprises no more than about 0.06 EU/mg.

24. The pharmaceutical composition of claim 1, prepared by the process comprising the steps of dissolving the compound of formula (IV) in glacial acetic acid to form a solution, freeze drying the solution and subliming the acetic acid at reduced pressure.

25. The pharmaceutical composition of claim 1, wherein the pharmaceutical composition comprises not more than 5% acetic acid.

26. The pharmaceutical composition of claim 25, wherein the acetic acid comprises less than about 200 ppm water.

27. A method of treating cancer comprising intravenously administering to a subject in need thereof the pharmaceutical composition of claim 1, and a pharmaceutically acceptable diluent or solvent.

* * * * *